US010912264B2

(12) United States Patent
Chan et al.

(10) Patent No.: US 10,912,264 B2
(45) Date of Patent: Feb. 9, 2021

(54) GENERATION OF HAPLOID PLANTS AND IMPROVED PLANT BREEDING

(71) Applicant: The Regents of the University of California, Oakland, CA (US)

(72) Inventors: Simon Chan; Ravi Maruthachalam, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 111 days.

(21) Appl. No.: 16/385,982

(22) Filed: Apr. 16, 2019

(65) Prior Publication Data
US 2019/0343060 A1 Nov. 14, 2019

Related U.S. Application Data

(63) Continuation of application No. 14/939,181, filed on Nov. 12, 2015, now Pat. No. 10,306,848, which is a continuation of application No. 14/088,065, filed on Nov. 22, 2013, now Pat. No. 9,215,849, which is a continuation of application No. 12/898,216, filed on Oct. 5, 2010, now Pat. No. 8,618,354.

(60) Provisional application No. 61/248,996, filed on Oct. 6, 2009.

(51) Int. Cl.
*A01H 1/08* (2006.01)
*C07K 14/415* (2006.01)
*C12N 15/82* (2006.01)
*A01H 1/02* (2006.01)

(52) U.S. Cl.
CPC ............... *A01H 1/08* (2013.01); *A01H 1/02* (2013.01); *C07K 14/415* (2013.01); *C12N 15/8241* (2013.01); *C12N 15/8261* (2013.01); *C12N 15/8287* (2013.01); *Y02A 40/146* (2018.01)

(58) Field of Classification Search
CPC .............................. A01H 1/08; C12N 15/8241
See application file for complete search history.

(56) References Cited

U.S. PATENT DOCUMENTS

| 5,749,169 A | 5/1998 | Briggs et al. |
| 8,618,354 B2 | 12/2013 | Chan et al. |
| 2009/0144849 A1 | 6/2009 | Lutfiyya |
| 2010/0017908 A1 | 1/2010 | Zhao et al. |

FOREIGN PATENT DOCUMENTS

| WO | 2010/079432 A1 | 7/2010 |
| WO | 2012/075195 A1 | 6/2012 |

OTHER PUBLICATIONS

Maheshwari, S. et al., PLOS Genetics (published Jan. 26, 2015) vol. 11, No. 2; pp. 1-20. (Year: 2015).*
Supplementary European Search Report from EP 10822533.5, dated Aug. 20, 2013.
The International Search Report from PCT/2010/051483, dated Jan. 6, 2011.
Black et al.; "Structural determinants for generating centromeric chromatin"; *Nature*; 430:578-582 (2004).
Chen et al.; "The N Terminus of the centromere H3-like protein Cse4p performs an essential function distinct from that of the histone fold domain"; *Mol. Cell Biol.*; 20(18):7037-7048 (Sep. 2000).
d'Erfurth et al.; "Turning Meiosis into Mitosis"; *PLoS Biol.*; Jun. 2009; 7(6):e1000124 (10 pages) ePub Jun. 9, 2009. doi: 10.1371/journal.pbio.1000124.
Forster et al.; "The resurgence of haploids in higher plants"; *Trends in Plant Sci.*; 12(8):368-375 (2007).
Keith et al.; "Analysis of Primary Structural Determinants That Distinguish the Centromere-Specific Function of Histone Variant Cse4p from Histone H3"; *Mol. Cell. Biol.*; 19(9):6130-6139 (Sep. 1999).
Konev et al.; "The CHD1 motor protein is required for depositoin of histone variant H3.3 into chromatin in vivo"; *Science*; 317(5841):1087-1090 (2007).
Lermontova, Inna et al.; "Loading of *Arabidopsis* Centromeric Histone CENH3 Occurs Mainly during G2 and Requires the Presence of the Histone Fold Domain"; 2006, *The Plant Cell*, vol. 18, pp. 2443-2451.
Li, Xuexian et al.; "Fused sister kinetochores initiate the reductional division in meiosis I"; 2009, *Nature Cell Biology*, vol. 11, pp. 1103-1108.
Marimuthu et al., "Synthetic Clonal Reproduction Through Seeds"; 2011, Science; vol. 331, pp. 876.
Nagaki, Kiyotaka et al.; "Sequencing of a rice centromere uncovers active genes"; 2004, *Nature Genetics*, vol. 36, No. 2, pp. 138-145.
Ravi et al.; "Haploid plants produced by centromere-mediated genome elimination"; *Nature*; 464(7288):615-620 (Mar. 2010).
Ravi et al.; "The rapidly evolving centromere-specific histone has stringent functional requirements in *Arabidopsis thaliana*"; *Genetics*; 186(2):461-471 (Oct. 2010). ePub Jul. 13, 2010.
Régnier et al.; "CENP-A is required for accurate chromosome segregation and sustained kinetochore association of BubR1"; *Mol. Cell Biol.*; 25(10):3967-3981 (2005).
Strepp et al. "Plant nuclear gene knockout reveals a role in plastid division for the homolog of the bacterial cell division protein FtsZ, an ancestral tubulin"; *Proc. Natl. Acad. Sci. USA*; 95:4368-4373 (1998).
Uniprot reference: A4PIF4_LEPVR, May 15, 2007; retrived from the internet: <URL: http://www.genome.jp/dbget-bin/www_bget?uniprot:A4PIF4_LEPVR>, SEQ ID No. 436, 1 page.
Wang et al.; "Non-homologous chromosome pairing and crossover formation in haploid rice meiosis"; *Chromosoma*; 120:353-365 (Feb. 2011; ePub Aug. 13, 2010).

(Continued)

*Primary Examiner* — Russell Kallis
(74) *Attorney, Agent, or Firm* — Kilpatrick Townsend and Stockton LLP

(57) ABSTRACT

Methods and compositions for generating haploid organisms are described.

13 Claims, 1 Drawing Sheet
Specification includes a Sequence Listing.

(56) References Cited

OTHER PUBLICATIONS

Yu, HengXiu et al.; "Generating of rice OsCENH3-GFP transgenic plants and their genetic applications"; 2008, *Chinese Science Bulletin*, vol. 53, No. 19, pp. 2981-2988.
Kasha, K.J., et al.; "High Frequency Haploid Production in Barley (*Hordeum vulgare* L.)", Feb. 28, 1970, Nature, vol. 225, pp. 874-876.
Cooper, J. et al., "Adaptive Evolution of the Histone Fold Domain in Centromeric Histones," Molecular Biology and Evolution, 2004, vol. 21, No. 9, pp. 1712-1718.
Sanei, M., et al., "Loss of Centromeric Histone H3 (CENH3) from Centromeres Precedes Uniparental Chromosome Elimination in Interspecific Barley Hybrids," Aug. 16, 2011, PNAS, vol. 108, No. 33, pp. 1-15.

\* cited by examiner

```
A. thaliana H3.3  MAR--TKQSARKSHGG--------------------KAPTKQ------------- 20
Human H3.3        MAR--TKQTARKSTGG--------------------KAPRKQ------------- 20
C. albicans       MARLSGQSSGRQTGQGTSAEAIRQQREELRRQRELRLQQQQAERQQQRQQYRTEQSPIV 60
Human             MGP--RRRSRKPEAP---------------------RRRSPSPT----------- 21
A. thaliana       MARTKHRVTRSQPRNQT-------------------DAAGASSSQA--------- 27
Poplar            MARTKHPVARKRARSPK-------------------RSD-ASPSTP--------- 26
Rice              MARTKHPAVRKSKAEPK-------------------KKLQFERS----------- 25
                  *  .

A. thaliana H3.3  ----------------------LATKAARKSAPTTG-----------GVKK--- 38
Human H3.3        ----------------------LATKAARKSAPSTG-----------GVKK--- 38
C. albicans       PAATSSSRYSQFGIYRNQPGDVVDTLASSLPRRTTTTRP---------EVNRTVP 106
Human             ----------------------PTPGPSRRGPSLG-------------ASSH-- 38
A. thaliana       ----------------------AGPTTTPTRRGGEGGDNTQQTNPTTSPATGTRRGAK 63
Poplar            ----------------------RTPTSSRTRPQANG----QQ----GSSTQR-- 48
Rice              ----------------------PRPSKAQRAGGGTGTSATTRSAAGTS-ASGTPRQQT 60
                    .:                                             :

A. thaliana H3.3  -----------PHRFRPGTVALREIRKYQKSTELLNRKLPFQRLVREIAQDFK---TD 82
Human H3.3        -----------PHRYRPGTVALREIRRYQKSTELLIRKLPFQRLVREIAQDFK---TD 82
C. albicans       R----------VKKRYRPGTKALREIRQYQKSTDLLIRKLPFARLVREISLDFVGPSYG 155
Human             -----------QHSRRRQGWLKEIRKLQKSTHLLIRKLPFSRLAREICVKFTRG-VD 83
A. thaliana       RSRQAMPRGSQKKSYRYRPGTVALKEIRHFQKQTNLLIPAASFIREVRSITHMLAPP-QI 122
Poplar            -----------QRKKHRFRSGTVALREIRQYQKTWRPLIPAASFIRCVRMITQEFSR-EV 96
Rice              K----------QRKPHRFRPGTVALREIRKFQKTTELLIPFAPFSRLVREITDFYSK-DV 109
                    .*    *:***: **     *  .* *.* *

A. thaliana H3.3  LRFQSHAVLALQEAAEAYLVGLFEDTNLCAIHAKRVTIMPKDVQLARRIRAERA---- 136
Human H3.3        LRFQSAAIGALQEASEAYLVGLFEDTNLCAIHAKRVTIMPKDIQLARRIRGERA---- 136
C. albicans       LRWQSNAILALQEASESFLIHLLEDTNLCAIHAKRVTIMQKDIQLARRIRGQSWIL- 211
Human             FNWQAQALLALQEAAEAFLVHLFEDAYLLTLHAGRVTLFPKDVQLARRIRGLEEGLG 140
A. thaliana       NRWTAEALVALQEAAEDYLVGLFSDSMLCAIHARRVTLMRKDFELARRLGGKGRPW- 178
Poplar            NRWTAEALVAIQEAAEDFLVHLFEDGMLCAIHAKRVTLMKKDFELARRLGGKGRPW- 152
Rice              SRWTLEALLALQEAAEYHLVDIFEVSNLCAIHAKRVTIMQKDMQLARRIGGR-RPW- 164
                    .:  *:  *:****.* .*: ::.   *  :: **  ***::  **.****:  .
```

GENERATION OF HAPLOID PLANTS AND IMPROVED PLANT BREEDING

CROSS-REFERENCE TO RELATED PATENT APPLICATIONS

The present application is a continuation of U.S. patent application Ser. No. 14/939,181, filed Nov. 12, 2015, which is a continuation of U.S. patent application Ser. No. 14/088,065, filed Nov. 22, 2013, now U.S. Pat. No. 9,215,849, which is a continuation of U.S. patent application Ser. No. 12/898,216, filed Oct. 5, 2010, now U.S. Pat. No. 8,618,354, which claims benefit of priority to U.S. Provisional Patent Application No. 61/248,996, filed Oct. 6, 2009, each of which is incorporated by reference.

REFERENCE TO A SEQUENCE LISTING SUBMITTED AS AN ASCII TEXT FILE

The Sequence Listing written in file 081906-1135935.txt, created on Apr. 16, 2019, (147,116 bytes, machine format IBM-PC, MS-Windows operating system), in accordance with 37 C.F.R. §§ 1.821 to 1.825 is hereby incorporated by reference in its entirety for all purposes. No new matter was added.

BACKGROUND OF THE INVENTION

Although plant breeding programs worldwide have made considerable progress developing new cultivars with improved disease resistances, yields and other, useful traits, breeding as a whole relies on screening numerous plants to identify novel, desirable characteristics. Very large numbers of progeny from crosses often must be grown and evaluated over several years in order to select one or a few plants with a desired combination of traits.

Standard breeding of diploid plants often requires screening and back-crossing of a large number of plants to achieve the desired genotype. One solution to the problem of screening large numbers of progeny has been to produce haploid plants, the chromosomes of which can be doubled using colchicine or other means to achieve instantly homozygous, doubled-haploid plants.

Thus, marked improvements in the economics of breeding can be achieved via doubled haploid production, since selection and other procedural efficiencies can be markedly improved by using true-breeding (homozygous) progenies. With doubled haploid production systems, homozygosity is achieved in one generation. Thus, the breeder can eliminate the numerous cycles of inbreeding necessary by conventional methods to achieve practical levels of homozygosity. Indeed, true homozygosity for all traits is not even achievable by conventional breeding methods.

BRIEF SUMMARY OF THE INVENTION

The present invention provides for new ways for producing haploid organisms.

In some embodiments, the invention provides a transgenic plant comprising a heterologous transgene expression cassette, the expression cassette comprising a promoter operably linked to a polynucleotide encoding a recombinantly altered CENH3, CENPC, MIS12, NDC80 or NUF2 polypeptide, wherein in the event the recombinantly altered polypeptide is expressed in a first plant having a corresponding inactivated endogenous CENH3, CENPC, MIS12, NDC80 or NUF2 gene and the first plant is crossed to a wildtype plant, at least 0.1% of resulting progeny are haploid.

In some embodiments, one or two alleles of the endogenous CENH3, CENPC, MIS12, NDC80 or NUF2 genomic coding sequence of the plant is inactivated or knocked out. In some embodiments, all alleles of the endogenous CENH3, CENPC, MIS12, NDC80 or NUF2 genomic coding sequence of the plant is inactivated or knocked out. In some embodiments, the plant, when crossed with a wildtype plant, generates at least 0.1% (or, e.g., 0.5, 1, 2, 5, 10, 20% or more) haploid progeny.

In some embodiments, the polypeptide is a recombinantly altered CENH3 polypeptide. In some embodiments, the polypeptide comprises a heterologous amino acid sequence of at least 5 amino acids linked to a protein comprising a CENH3 histone-fold domain, wherein the amino acid sequence is heterologous to the CENH3 histone-fold domain. In some embodiments, the heterologous amino acid sequence is linked directly to the CENH3 histone-fold domain and the polypeptide lacks a CENH3 tail domain. In some embodiments, the heterologous amino acid sequence is linked to the CENH3 histone-fold domain via an intervening protein sequence. In some embodiments, the intervening protein sequence comprises a non-CENH3 histone H3 tail domain. In some embodiments, the non-CENH3 histone H3 tail domain comprises an amino acid sequence at least 70% identical to SEQ ID NO:95, or a fragment thereof at least 20 amino acids long.

In some embodiments, the intervening protein sequence comprises a CENH3 tail domain. In some embodiments, the intervening protein sequence comprises a histone H3 tail domain and a heterologous histone CENH3 tail domain. In some embodiments, the CENH3 tail domain is heterologous to the CENH3 histone-fold domain.

In some embodiments, the heterologous amino acid sequence is at least 10 amino acids long. In some embodiments, the intervening protein sequence comprises a histone H3 tail domain and a heterologous histone CENH3 tail domain. the heterologous amino acid sequence comprises green fluorescent protein. In some embodiments, the heterologous amino acid sequence disrupts centromeres. In some embodiments, the CENH3 histone-fold domain is selected from the group consisting of SEQ ID NOs: 49-94.

In some embodiments, the polypeptide comprises a non-CENH3 tail domain linked to a CENH3 histone-fold domain.

In some embodiments, the polypeptide comprises a CENH3 histone-fold domain and a truncated CENH3 tail domain, wherein the amino terminus of the tail domain is truncated relative to the plant's endogenous tail domain. In some embodiments, the truncated CENH3 tail domain lacks three or more amino terminal amino acids of the endogenous tail domain. In some embodiments, a heterologous amino acid sequence is linked to the amino terminus of the truncated tail domain. In some embodiments, the heterologous amino acid sequence is at least 10 amino acids long. In some embodiments, the heterologous amino acid sequence comprises green fluorescent protein. In some embodiments, the heterologous amino acid sequence disrupts centromeres. In some embodiments, the CENH3 histone-fold domain is selected from the group consisting of SEQ ID NOs: 49-94.

In some embodiments, the polypeptide is a recombinantly altered CENPC, MIS12, NDC80 and NUF2 polypeptide.

The present invention also provides for an isolated nucleic acid comprising a polynucleotide encoding a polypeptide, wherein the polypeptide comprises:

a non-CENH3 tail domain linked to a CENH3 histone-fold domain; or
a truncated CENH3 tail domain linked to a CENH3 histone-fold domain, wherein the amino terminus of the tail domain is truncated.

The present invention also provides for a plant comprising a silenced CENH3 or one or two copies of an allele of a knocked out, inactivated, or mutated endogenous CENH3 gene.

The present invention also provides for method of generating a haploid plant, the method comprising,
crossing a plant expressing an endogenous CENH3 protein to a transgenic plant comprising a heterologous transgene expression cassette, the expression cassette comprising a promoter operably linked to a polynucleotide encoding a recombinantly altered CENH3, CENPC, MIS12, NDC80 or NUF2 polypeptide, wherein in the event the recombinantly altered polypeptide is expressed in a first plant having a corresponding inactivated endogenous CENH3, CENPC, MIS12, NDC80 or NUF2 gene and the first plant is crossed to a wildtype plant, at least 0.1% of resulting progeny are haploid; and
selecting F1 haploid progeny generated from the crossing step.

In some embodiments, the plant expressing an endogenous CENH3 protein is the pollen parent of the cross.

In some embodiments, the plant expressing an endogenous CENH3 protein is the ovule parent of the cross.

In some embodiments, the method further comprises converting at least one selected haploid plant into a doubled haploid plant.

A method of making a transgenic plant comprising a heterologous transgene expression cassette, the expression cassette comprising a promoter operably linked to a polynucleotide encoding a recombinantly altered CENH3, CENPC, MIS12, NDC80 or NUF2 polypeptide, wherein in the event the recombinantly altered polypeptide is expressed in a first plant having a corresponding inactivated endogenous CENH3, CENPC, MIS12, NDC80 or NUF2 gene and the first plant is crossed to a wildtype plant, at least 0.1% of resulting progeny are haploid, the method comprising,
transforming plant cells with a nucleic acid comprising the expression cassette; and
selecting transformants comprising the nucleic acid, thereby making the plant.

In some embodiments, the present invention provides an isolated polynucleotide encoding a polypeptide, wherein the polypeptide comprises:
an amino acid sequence of at least 5 amino acids linked to a protein comprising a CENH3 histone-fold domain, wherein the amino acid sequence is heterologous to the CENH3 histone-fold domain; or
a protein comprising a CENH3 histone-fold domain and a truncated CENH3 tail domain, wherein the amino terminus of the tail domain is truncated.

In some embodiments, the heterologous amino acid sequence is linked directly to the CENH3 histone-fold domain. In some embodiments, the polypeptide lacks a CENH3 tail domain.

In some embodiments, the heterologous amino acid sequence is linked to the CENH3 histone-fold domain via an intervening protein sequence. In some embodiments, the intervening protein sequence comprises a non-CENH3 histone H3 tail domain. In some embodiments, the intervening protein sequence comprises a CENH3 tail domain. In some embodiments, the CENH3 tail domain is heterologous to the CENH3 histone-fold domain. In some embodiments, the non-CENH3 histone H3 tail domain comprises an amino acid sequence at least 70% identical to SEQ ID NO:95, or a fragment thereof at least 20 amino acids long. In some embodiments, the intervening protein sequence comprises a histone H3 tail domain and a heterologous histone CENH3 tail domain.

In some embodiments, the heterologous amino acid sequence is at least 3, 5, 10, 15, 20, 30, or 50 amino acids long, optionally lacking a fixed secondary structure.

In some embodiments, the heterologous amino acid sequence comprises green fluorescent protein.

In some embodiments, the heterologous amino acid sequence disrupts centromeres.

In some embodiments, the CENH3 histone-fold domain is selected from the group consisting of SEQ ID NOs: 49-94.

In some embodiments, the polypeptide comprises a protein comprising a CENH3 histone-fold domain and a truncated CENH3 tail domain, wherein the amino terminus of the tail domain is truncated.

In some embodiments, the truncated CENH3 tail domain lacks at least 1, 2, 3, 4, 5, 6, 10, 15, or 20 amino terminal amino acids of the endogenous tail domain. In some embodiments, a heterologous amino acid sequence is linked to the amino terminus of the truncated tail domain. In some embodiments, the heterologous amino acid sequence is at least at least 3, 5, 10, 15, 20, 30, or 50 amino acids long. In some embodiments, the heterologous amino acid sequence comprises green fluorescent protein. In some embodiments, the heterologous amino acid sequence disrupts centromeres.

In some embodiments, the CENH3 histone-fold domain is selected from the group consisting of SEQ ID NOs: 49-94.

The present invention also provides an expression cassette comprising any of the above-listed the polynucleotides, wherein the expression cassette comprises a promoter operably linked to the polynucleotide encoding a polypeptide. In some embodiments, the invention provides for a vector comprising the expression cassette.

In some embodiments, the invention provides for a plant comprising the expression cassette.

In some embodiments, the heterologous histone tail domain comprises a histone H3 tail domain or a heterologous histone CENH3 tail domain.

In some embodiments, the polypeptide comprises a histone H3 tail domain and a histone CENH3 tail domain.

In some embodiments, the plant comprises a silenced CENH3 or one or two copies of an allele of a knocked out or mutated endogenous CENH3 gene.

In some embodiments, the expression cassette is integrated into the chromosome of the plant.

The present invention also provides for a plant comprising a silenced CENH3 or one or two copies of an allele of a knocked out or mutated endogenous CENH3 gene.

The present invention also provides for a method of generating a haploid plant. In some embodiments, the method comprises, crossing a plant expressing an endogenous CENH3 protein to the plant as described herein (e.g., expressing a tailswap protein); and
selecting F1 haploid progeny generated from the crossing step.

In some embodiments, the plant expressing an endogenous CENH3 protein is the pollen parent of the cross.

In some embodiments, the plant expressing an endogenous CENH3 protein is the ovule parent of the cross.

In some embodiments, the method further comprises converting at least one selected haploid plant into a doubled haploid plant.

Other aspects of the invention will be clear from the remainder of the text herein.

Definitions

An "endogenous" gene or protein sequence refers to a non-recombinant sequence of an organism as the sequence occurs in the organism before human-induced mutation of the sequence. A "mutated" sequence refers to a human-altered sequence. Examples of human-induced mutation include exposure of an organism to a high dose of chemical, radiological, or insertional mutagen for the purposes of selecting mutants, as well as recombinant alteration of a sequence. Examples of human-induced recombinant alterations can include, e.g., fusions, insertions, deletions, and/or changes to the sequence.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. A plant promoter can be, but does not have to be, a nucleic acid sequence originally isolated from a plant.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide or polypeptide sequence is "heterologous to" an organism or a second sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). In another example, a CENH3 tail domain from a first species is heterologous to a CENH3 histone-fold domain from a second species.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology, Volumes* 1-3, John Wiley & Sons, Inc. (1994-1998)). In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A "transgene" is used as the term is understood in the art and refers to a heterologous nucleic acid introduced into a cell by human molecular manipulation of the cell's genome (e.g., by molecular transformation). Thus a "transgenic plant" is a plant comprising a transgene, i.e., is a genetically-modified plant. The transgenic plant can be the initial plant into which the transgene was introduced as well as progeny thereof whose genome contain the transgene.

The term "corresponding" as used herein is used to mean "respective." For example, where it is said that a plant contains a recombinantly altered copy of a protein selected from A, B, and C, and the plant also contains a "corresponding" mutated endogenous copy of the gene selected from a gene encoding A, B, or C, if the plant contains a recombinantly altered protein A, the corresponding mutated endogenous copy would also be A. Alternatively, if the plant contains a recombinantly altered protein B, the corresponding mutated endogenous copy would also be B, etc.

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase, and/or formation of double-stranded duplexes, and do not significantly alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The phrase "host cell" refers to a cell from any organism. Exemplary host cells are derived from plants, bacteria, yeast, fungi, insects or other animals. Methods for introducing polynucleotide sequences into various types of host cells are well known in the art.

An "expression cassette" refers to a nucleic acid construct, which when introduced into a host cell (e.g., a plant cell), results in transcription and/or translation of a RNA or polypeptide, respectively. An expression cassette can result in transcription without translation, for example, when an siRNA or other non-protein encoding RNA is transcribed.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Examples of algorithms that are suitable for determining percent sequence identity and sequence similarity are the BLAST and BLAST 2.0 algorithms, which are described in Altschul et al., *Nuc. Acids Res.* 25:3389-3402 (1977), and Altschul et al., *J. Mol. Biol.* 215:403-410 (1990), respectively. Software for performing BLAST analyses is publicly available on the Web through the National Center for Biotechnology Information (at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity to a designated reference sequence. Alternatively, percent identity can be any integer from 25% to 100%, for example, at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Percent identity of polypeptides can be any integer from 40% to 100%, for example, at least 40%, 45%, 50%, 55%, 60%, 65%, 70%, 75%, 80%, 85%, 90%, 95%, or 99%. In some embodiments, polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

BRIEF DESCRIPTION OF THE DRAWINGS

FIG. 1 illustrates a sequence alignment of various CENH3 proteins (*A. thaliana* H3.3=SEQ ID NO:1; Human H3.3=SEQ ID NO:2; *C. albicans*=SEQ ID NO:106; Human=SEQ ID NO107; *A. thaliana*=SEQ ID NO:10; Poplar=SEQ ID NO:11; Rice=SEQ ID NO:108).

DETAILED DESCRIPTION

I. Introduction

The present invention is based, in part, on the surprising discovery that elimination of an endogenous CENH3 in combination with expression of a heterologous protein comprising an altered CENH3 results in a plant that has useful properties for breeding. For example, when a plant that lacks an endogenous CENH3 protein, and expresses a protein comprising (listed from amino terminus to carboxyl terminus) a GFP tag, a non-CENH3 tail domain and a CENH3 histone fold domain, is crossed to a plant having an endogenous CENH3 protein, a portion of the resulting progeny lack all chromosomes derived from the parent plant that expresses an altered version of CENH3. Thus, the invention allows for the production of haploid progeny. Haploid plants are useful, for example, for improving and speeding breeding.

CENH3 is a member of the kinetochore complex, the protein structure on chromosomes where spindle fibers attach during cell division. Without intending to limit the scope of the invention, it is believed that the observed results are due in part to generation of a kinetochore protein that acts more weakly than wildtype, thereby resulting in functional kinetochore complexes (for example, in mitosis), but which result in relatively poorly segregating chromosomes during meiosis relative to chromosomes also containing wildtype kinetochore complexes from the other parent. This results in functional kinetochore complexes when the altered protein is the only isoform in the cell, but relatively poorly segregating chromosomes during mitosis when the parent with altered kinetochores is crossed to a parent with wildtype kinetochore complexes. In addition to CENH3, other kinetochore proteins include, e.g., CENPC, MCM21, MIS12, NDC80, and NUF2. Accordingly, the present invention provides for plants, fungi, or animals (or cells thereof) that express a recombinant mutated kinetochore protein (including but not limited to CENH3, CENPC, MCM21, MIS12, NDC80, and NUF2) that disrupts the centromere, and/or plants, fungi, or animals (or cells thereof) in which at least one or both copies of an allele of the endogenous CENH3 gene has been knocked out, mutated to reduce or eliminate its function, or silenced. As explained in more detail below, the mutated kinetochore protein can be mutated in many different ways, including but not limited to, as a "tailswap" protein, comprising a CENH3 histone-fold domain and a heterologous amino terminal sequence. The present invention also provides for methods of generating a haploid plant by crossing a plant expressing a mutated kinetochore protein (including but not limited to a tailswap CENH3 protein), and not expressing an endogenous CENH3 protein, to a plant that expresses an endogenous CENH3 protein.

II. Kinetochore Proteins

A. CENH3 Proteins

CENH3 proteins are a well characterized class of proteins that are variants of H3 histone proteins and that are specialized proteins associated with the centromere. CENH3 proteins are characterized by a variable tail domain, which does not form a rigid secondary structure, and a conserved histone fold domain made up of three α-helical regions connected by loop sections. Additional structural and functional features of CENH3 proteins can be found in, e.g., Cooper et al., *Mol Biol Evol.* 21(9):1712-8 (2004); Malik et al., *Nat Struct Biol.* 10(11):882-91 (2003); Black et al., *Curr Opin Cell Biol.* 20(1):91-100 (2008). CENH3 proteins are one of the proteins that form the kinetochore complex.

A wide variety of CENH3 proteins have been identified. See, e.g., SEQ ID NOs:1-48. It will be appreciated that the above list is not intended to be exhaustive and that additional CENH3 sequences are available from genomic studies or can be identified from genomic databases or by well-known laboratory techniques. For example, where a particular plant or other organism species CENH3 is not readily available from a database, one can identify and clone the organism's CENH3 gene sequence using primers, which are optionally degenerate, based on conserved regions of other known CENH3 proteins.

The practice of the present invention will generally employ conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

i. CENH3 Histone Fold Domain

As noted above, the CENH3 histone fold domain is conserved between CENH3 proteins from different species. The CENH3 histone fold domain can be distinguished by three α-helical regions connected by loop sections. While it will be appreciated that the exact location of the histone fold domain will vary in CENH3 proteins from other species, it will be found at the carboxyl terminus of an endogenous (wildtype) CENH3 protein. Thus, in some embodiments, a CENH3 protein can be identified in an endogenous protein as having a carboxyl terminal domain substantially similar (e.g., at least 30%, 40%, 50%, 60%, 70%, 85%, 90%, 95% or more identity) to any of SEQ ID NOs: 49-94. An alignment of a selection of CENH3 proteins is provided in FIG. 1 and illustrates areas of conservation in the histone fold domain.

The border between the tail domain and the histone fold domain of CENH3 proteins is at, within, or near (i.e., within 5, 10, 15, 20, or 25 amino acids from the "P" of) the conserved PGTVAL (SEQ ID NO:114) sequence. The PGTVAL (SEQ ID NO:114) sequence is approximately 81 amino acids from the N terminus of the *Arabidopsis* CENH3 protein, though the distance from the N terminus of different endogenous CENH3 proteins varies. See, for example, the sequence listing. Thus, in some embodiments, the histone fold region of CENH3 employed in the tailswap proteins includes all of the C-terminal amino acids of an endogenous CENH3 protein (or a protein substantially similar to the endogenous sequence) up to and including the PGTVAL (SEQ ID NO:114). SEQ ID NOS:49-94 reflect this option. In other embodiments, the tailswap proteins of the invention can comprise more or less of the CENH3 sequence. For example, in some embodiments, the tailswap will comprise the C-terminal sequence of a CENH3 protein, but only up to an amino acid 5, 10, 15, 20, or 25 amino acids in the C-terminal direction from the "P" of the conserved PGTVAL (SEQ ID NO:114) sequence. In some embodiments, the tailswap will comprise the C-terminal sequence of a CENH3 protein, but only up to an amino acid 5, 10, 15, 20, or 25 amino acids in the N-terminal direction from the "P" of the conserved PGTVAL (SEQ ID NO:114) sequence.

ii. CENH3 Histone Tail Domain

Although the histone-fold domain of CENH3 evolves more rapidly than that of conventional H3, CENH3 and H3 histone-fold domains can still be aligned. In contrast, N-terminal tail domains of CENH3 are highly variable even between closely related species. Histone tail domains (including CENH3 tail domains) are flexible and unstructured, as shown by their lack of strong electron density in the structure of the nucleosome determined by X-ray crystallography (Luger et al., *Nature* 389(6648):251-60 (1997)).

iii. Mutated CENH3 Proteins

Any number of mutations of CENH3 can be introduced into a CENH3 protein to generate a mutated (including but not limited to a recombinantly altered) CENH3 protein capable of generating haploid plants when expressed in a plant lacking, or having suppressed expression of, an endogenous CENH3 protein, and where the resulting transgenic plant is crossed to a plant expressing a wildtype CENH3 protein. Active mutated CENH3 proteins can be identified, for example, by random mutagenesis, by single or multiple amino acid targeted mutagenesis, by generation of complete or partial protein domain deletions, by fusion with heterologous amino acid sequences, or by combinations thereof. "Active" mutant CENH3 proteins refer to proteins, which when expressed in a plant in which CENH3 is knocked out or inactivated, results in viable plants, which viable plants when crossed to a wildtype plant, produce haploid progeny at a more than normal frequency (e.g., at least 0.1, 0.5, 1, 5, 10, 20% or more). Mutated CENH3 proteins can be readily tested by recombinant expression of the mutated CENH3 protein in a plant lacking endogenous CENH3 protein, crossing the transgenic plant (as a male or female, depending on fertility) to a plant expression wildtype CENH3 protein, and then screening for the production of haploid progeny.

In some embodiments, the mutated CENH3 protein is identical to an endogenous CENH3 protein but for 1, 2, 3, 4, 5, 6, 7, 8, or more (e.g., 1-2, 1-4, 1-7) amino acids. For example, in some embodiments, the endogenous wildtype protein from the plant is identical or substantially identical to any of SEQ ID NOs: 1-48 and the mutated CENH3 protein differs from the endogenous CENH3 protein by 1, 2, 3, 4, 5, 6, 7, 8, or more (e.g., 1-2, 1-4, 1-7) amino acids.

In some embodiments, the mutated CENH3 protein contains a CENH3 histone-fold domain identical to the CENH3 histone-fold domain of an endogenous CENH3 protein but for 1, 2, 3, 4, 5, 6, 7, 8, or more (e.g., 1-2, 1-4, 1-7) amino acids. For example, in some embodiments, the endogenous wildtype CENH3 histone-fold domain from the plant is identical or substantially identical to any of SEQ ID NOs: 49-94 and the mutated CENH3 protein contains a CENH3 histone-fold domain that differs from the endogenous CENH3 protein histone-fold domain by 1, 2, 3, 4, 5, 6, 7, 8, or more (e.g., 1-2, 1-4, 1-7) amino acids.

It is believed that active CENH3 mutants include, for example, proteins comprising:

a heterologous amino acid sequence (including but not limited to GFP) linked to a CENH3 truncated or complete tail domain or non-CENH3 tail domain, either of which is linked to a CENH3 histone fold domain; or a CENH3 truncated tail domain, a heterologous CENH3 tail domain, or non-CENH3 tail domain, either of which is linked to a CENH3 histone fold domain.

In some embodiments, the mutated CENH3 protein comprises a fusion of an amino-terminal heterologous amino acid sequence to the histone-fold domain of a CENH3 protein. Generally, the histone fold domain will be identical or at least substantially identical to the CENH3 protein endogenous to the organism in which the mutated CENH3 protein will be expressed. In some embodiments, the mutated CENH3 protein will include a histone tail domain, which can be, for example, a non-CENH3 tail domain, or a CENH3 tail domain.

It is believed that a large number of different amino acid sequences, when linked to a protein comprising a CENH3 histone-fold domain and a sequence that can function as or replace a histone tail domain, can be used according to the present invention. In some embodiments, the heterologous sequence is linked directly to the CENH3 histone-fold domain. In some embodiments, the heterologous sequence is linked is an intervening amino acid sequence to the CENH3 histone-fold domain. In some embodiments, the intervening amino acid sequence is an intact or truncated CENH3 tail domain. In some embodiments, the heterologous amino acid sequence, in combination with the histone-fold domain, will be sufficient to prevent the lethality associated with loss of endogenous CENH3, but will sufficiently disrupt centromeres to allow for production of haploid progeny, as discussed herein. Thus, in some embodiments, the heterologous amino acid sequence will comprise a portion that is, or mimics the function of, a histone tail domain and optionally can also comprise a bulky amino acid sequence that disrupts centromere function. In some embodiments, at least a portion of the heterologous amino acid sequence of the mutated CENH3 protein comprises any amino acid sequence of at least 10, 20, 30, 40, 50, e.g., 10-30, 10-50, 20-50, 30-60 amino acids, optionally lacking a stable secondary structure (e.g., lacking coils, helices, or beta-sheets). In some embodiments, the tail domain has less than 90, 80, or 70% identity with the tail domain (e.g., the N-terminal 135 amino acids) of the CENH3 protein endogenous to the organism in which the mutated CENH3 protein will be expressed. In some embodiments, the tail domain of the mutated CENH3 protein comprises the tail domain of a non-CENH3 histone protein, including but not limited to an H3 histone protein. In some embodiments, the tail domain of the mutated CENH3 protein comprises the tail domain of a non-CENH3 histone protein endogenous to the organism in which the mutated CENH3 protein will be expressed. In some embodiments, the tail domain of the mutated CENH3 protein comprises the tail domain of a homologous or orthologous (from a different plant species) CENH3 tail. For example, it has been found that GFP fused to a maize CENH3 tail domain linked to an *Arabidopsis* CENH3 histone-fold domain is active.

As noted above, in some embodiments, the tail domain of an H3 histone (not to be confused with a CENH3 histone) is used as the tail domain portion of the mutated CENH3 protein (these embodiments are sometimes referred to as "tailswap" proteins). Plant H3 tail domains are well conserved in various organisms. For example, a common H3 tail domain from plants is SEQ ID NO:95. Thus, in some embodiments, the heterologous tail portion of the tailswap protein will comprise an amino acid sequence substantially identical (e.g., at least 70, 80, 90, 95, or 100% identical) to SEQ ID NO:95, or a fragment thereof at least 15, 20, 25, 30, 35, or 40 amino acids long.

In some embodiments, the mutated CENH3 proteins of the invention will lack at least a portion (e.g., at least 5, 10, 15, 20, 25, 30, or more amino acids) of the endogenous CENH3 N-terminal region, and thus, in some embodiments, will have a truncated CENH3 tail domain compared to a wildtype endogenous CENH3 protein. Mutated CENH3 proteins may, or may not, be linked to a heterologous sequence.

Optionally, the heterologous amino acid sequence can comprise, or further comprise, one or more amino acid sequences at the amino and/or carboxyl terminus and/or linking the tail and histone fold domains. For example, in some embodiments, the mutated CENH3 protein (e.g., a tailswap or other CENH3 mutated protein) comprises a heterologous amino acid sequence linked to the amino end of the tail domain. In some embodiments, the heterologous sequence is linked to the amino terminus of an otherwise wildtype CENH3 protein, wherein the heterologous sequence interferes with centromere function. For example, it has been found, for example, that green fluorescent protein, when linked to wildtype CENH3, sufficiently disrupts centromeres to allow for production of haploid progeny. It is believed that the heterologous sequence can be any sequence that disrupts the CENH3 protein's ability to maintain centromere function. Thus, in some embodiments, the heterologous sequence comprises a an amino acid sequence of at least 5, 10, 15, 20, 25, 30, 50, or more kD.

In some embodiments, the mutated CENH3 protein will comprise a protein domain that acts as a detectable or selectable marker. For example, an exemplary selectable marker protein is fluorescent or an antibiotic or herbicide resistance gene product. Selectable or detectable protein domains are useful for monitoring the presence or absence of the mutated CENH3 protein in an organism.

B. Non-CENH3 Kinetochore Proteins

It is believed that other proteins that make up the kinetochore complex can also be mutated and expressed in a plant that otherwise does not express the corresponding endogenous kinetochore complex protein to result in a viable plant which, when crossed to a wildtype plant having a wildtype kinetochore complex, generates haploid progeny at a certain frequency (e.g., at least 0.1, 0.5, 1, 5, 10, 20,%, or more). Exemplary non-CENH3 members of the kinetochore complex include, e.g., CENPC, MCM21, MIS12, NDC80, and NUF2.

Active mutated non-CENH3 kinetochore complex proteins (e.g., CENPC, MCM21, MIS12, NDC80, or NUF2) can be identified, for example, by random mutagenesis, single or multiple amino acid targeted mutagenesis, by generation or complete or partial protein domain deletions, by fusion with heterologous amino acid sequences, or combinations thereof. "Active" mutant non-CENH3 kinetochore complex proteins refer to proteins, which when expressed in a plant in which the corresponding non-CENH3 kinetochore complex protein is knocked out or inactivated, results in viable plants, which when crossed to a wildtype plant, produce haploid progeny at a more than normal frequency (e.g., at least 1, 5, 10, 20% or more). In some embodiments, active mutated CENPC, MCM21, MIS12, NDC80, or NUF2 polypeptides are substantially identical to SEQ ID NOs: 96, 97, 98, 99, or 100, respectively. Mutated non-CENH3 kinetochore complex proteins (e.g., CENPC, MCM21, MIS12, NDC80, or NUF2) can be readily tested by recombinant expression of the mutated non-CENH3 kinetochore complex protein in a plant lacking endogenous non-CENH3 kinetochore complex protein, crossing the transgenic plant (as a male or female, depending on fertility) to a plant expressing a wildtype non-CENH3 kinetochore complex protein, and then screening for the production of haploid progeny.

In some embodiments, the mutated non-CENH3 kinetochore complex protein is identical to an endogenous non-CENH3 kinetochore complex protein but for 1, 2, 3, 4, 5, 6, 7, 8, or more (e.g., 1-2, 1-4, 1-7) amino acids. For example, in some embodiments, the endogenous wildtype protein from the plant is identical or substantially identical to any of SEQ ID NOs: 96, 97, 98, 99, or 100 and the mutated non-CENH3 kinetochore complex protein differs from the endogenous non-CENH3 kinetochore complex protein by 1, 2, 3, 4, 5, 6, 7, 8, or more (e.g., 1-2, 1-4, 1-7) amino acids.

Optionally, the heterologous amino acid sequence can comprise one or more amino acid sequences at the amino and/or carboxyl terminus and/or linking the tail and histone fold domains. For example, in some embodiments, the mutated non-CENH3 kinetochore complex protein comprises a heterologous amino acid sequence linked to an amino end of the non-CENH3 kinetochore complex protein. The heterologous sequence can be any sequence. In some embodiments, the heterologous sequence is linked to the amino terminus of an otherwise wildtype non-CENH3 kinetochore complex protein, wherein the heterologous sequence interferes with centromere function. In some embodiments, the heterologous sequence comprises a an amino acid sequence of at least 5, 10, 15, 20, 25, 30, 50, or more kD.

In some embodiments, the mutated non-CENH3 kinetochore complex protein will comprise a protein domain that acts as a detectable or selectable marker. For example, an exemplary selectable marker protein is fluorescent or an antibiotic or herbicide resistance gene product. Selectable or detectable protein domains are useful for monitoring the presence or absence of the mutated non-CENH3 kinetochore complex protein in an organism.

III. Generation of Organisms of the Invention

The present invention provides for organisms that do not express, or express at reduced levels (e.g., less than 90, 80, 70, 60, 50, 40, 30, 20, or 10% of wildtype levels), an endogenous CENH3 protein or non-CENH3 kinetochore complex protein and optionally that express a corresponding mutated CENH3 protein or non-CENH3 kinetochore complex protein. Generally, lack of a kinetochore complex protein is lethal, unless at least partially complemented by a mutated kinetochore complex protein as described herein. Without intending to limit the scope of the invention, it is believed that there are several ways to make an organism that lacks, or has reduced expression of, an endogenous kinetochore complex protein but that expresses a mutated version of that protein.

In some embodiments, one can generate a CENH3 mutation in an endogenous CENH3 (or non-CENH3 kinetochore complex protein) gene that reduces or eliminates CENH3 activity or expression, or generate a kinetochore complex protein (e.g., CENH3, CENPC, MCM21, MIS12, NDC80, or NUF2) gene knockout. In these embodiments, one can generate an organism heterozygous for the gene knockout or mutation and introduce an expression cassette for expression of the heterologous corresponding mutated kinetochore complex protein into the organism. Progeny from the heterozygote can then be selected that are homozygous for the mutation or knockout but that comprise the recombinantly expressed heterologous mutated kinetochore complex protein. Accordingly, the invention provides plants, plant cells or other organisms in which one or both CENH3 alleles are knocked out or mutated to significantly or essentially completely lack CENH3 activity, i.e., sufficient to induce embryo lethality without a complementary expression of a mutated kinetochore complex protein as described herein (e.g., a tailswap protein). The invention also provides plants, plant cells or other organisms in which one or both alleles of a non-CENH3 kinetochore complex gene are knocked out or mutated to significantly or essentially completely lack the corresponding non-CENH3 kinetochore complex protein activity, i.e., sufficient to induce embryo lethality without a complementary expression of a mutated kinetochore complex protein as described herein. In plants having more than a diploid set of chromosomes (e.g. tetraploids), all alleles can be inactivated, mutated, or knocked out.

Alternatively, one can introduce the expression cassette encoding a mutated kinetochore complex protein (e.g., including but not limited to, a tailswap protein) into an organism with an intact set of kinetochore complex protein (e.g., CENH3, CENPC, MCM21, MIS12, NDC80, or NUF2) alleles and then silence the endogenous kinetochore complex protein (e.g., CENH3, CENPC, MCM21, MIS12, NDC80, or NUF2) gene by any way known in the art. As an example, an siRNA or microRNA can be introduced or expressed in the organism that reduces or eliminates expression of the endogenous kinetochore complex protein (e.g., CENH3, CENPC, MCM21, MIS12, NDC80, or NUF2) protein.

Ideally, the silencing siRNA or other silencing agent is selected to silence the endogenous kinetochore complex protein (e.g., CENH3, CENPC, MCM21, MIS12, NDC80, or NUF2) gene but does not substantially interfere with expression of the mutated kinetochore complex protein (e.g., a tailswap protein). In situations where endogenous CENH3 is to be inactivated, this can be achieved, for example, by targeting the siRNA to the N-terminal tail coding section, or untranslated portions, or the CENH3 mRNA, depending on the structure of the mutated kinetochore complex protein. Alternatively, the mutated kinetochore complex protein transgene can be designed with novel codon usage, such that it lacks sequence homology with the endogenous kinetochore complex protein gene and with the silencing siRNA.

IV. Reduction or Elimination of Endogenous Kinetochore Complex Protein Expression A number of methods can be used to inhibit, mutate, or inactivate expression of a kinetochore complex protein (e.g., CENH3, CENPC, MCM21, MIS12, NDC80, or NUF2) in plants. For instance, antisense technology can be conveniently used to inactivate gene expression. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the polypeptide of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of a kinetochore complex protein (e.g., CENH3, CENPC, MCM21, MIS12, NDC80, or NUF2), or a portion of the kinetochore complex protein (e.g., CENH3, CENPC, MCM21, MIS12, NDC80, or NUF2) mRNA (including but not limited to untranslated portions of the mRNA) can be useful for producing a plant in which kinetochore complex protein expression is suppressed. The vectors of the present invention are optionally designed such that the inhibitory effect applies only to a kinetochore complex protein (e.g., CENH3, CENPC, MCM21, MIS12, NDC80, or NUF2) and does not affect expression of other genes. In situations where endogenous CENH3 is to be inactivated, one method for achieving this goal is to target the antisense sequence to CENH3 sequences (e.g., tail or untranslated mRNA sequences) not found in other proteins within a family of genes exhibiting homology or substantial homology to the CENH3 gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. For example, a sequence of between about 30 or 40 nucleotides can be used, and in some embodiments, about full length nucleotides should be used, though a sequence of at least about 20, 50, 100, 200, or 500 nucleotides can be used.

Catalytic RNA molecules or ribozymes can also be used to inhibit expression of a kinetochore complex protein (e.g., CENH3, CENPC, MCM21, MIS12, NDC80, or NUF2) genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65% to the target a kinetochore complex protein (e.g., CENH3, CENPC, MCM21, MIS12, NDC80, or NUF2) sequence, but a higher identity can exert a more effective repression of expression of the endogenous sequences. In some embodiments, sequences with substantially greater identity are used, e.g., at least about 80, at least about 95%, or 100% identity are used. As with antisense regulation, the effect can be designed and tested so as to not significantly affect expression of other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct. Genom.* 5: 240-244 (2004); Lu, et al., *Nucleic Acids Research* 32(21):e171 (2004)). For example, to achieve suppression of the expression of a kinetochore complex protein (e.g., CENH3, CENPC, MCM21, MIS12, NDC80, or NUF2) using RNAi, a double-stranded RNA having the sequence of an mRNA encoding the kinetochore complex protein (e.g., CENH3, CENPC, MCM21, MIS12, NDC80, or NUF2), or a substantially similar sequence thereof (including those engineered not to translate the protein) or fragment thereof, is introduced into a plant or other organism of interest. The resulting plants/organisms can then be screened for a phenotype associated with the target protein (optionally in the presence of expression of a tailswap protein to avoid lethality) and/or by monitoring steady-state RNA levels for transcripts encoding the protein. Although the genes used for RNAi need not be completely identical to the target gene, they may be at least 70%, 80%, 90%, 95% or more identical to the target (e.g., CENH3 sequences as described herein) gene sequence. See, e.g., U.S., Patent Publication No. 2004/0029283 for an example of a non-identical siRNA sequence used to suppress gene expression. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides can encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 10, 15, 20, 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

One of skill in the art will recognize that sense (including but not limited to siRNA) or antisense transcript should be targeted to sequences with the most variance between family members where the goal is to target only one (e.g., CENH3, CENPC, MCM21, MIS12, NDC80, or NUF2) histone family member.

Yet another way to suppress expression of an endogenous plant gene is by recombinant expression of a microRNA that suppresses a target (e.g., a CENH3, CENPC, MCM21, MIS12, NDC80, or NUF2 gene). Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Methods for introducing genetic mutations into plant genes and selecting plants with desired traits are well known and can be used to introduce mutations or to knock out a kinetochore complex protein (e.g., CENH3, CENPC, MCM21, MIS12, NDC80, or NUF2). For instance, seeds or other plant material can be treated with a mutagenic insertional polynucleotide (e.g., transposon, T-DNA, etc.) or chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used. Plants having mutated a kinetochore complex protein (e.g., CENH3, CENPC, MCM21, MIS12, NDC80, or NUF2) can then be identified, for example, by phenotype or by molecular techniques.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al., *Meth. Enzymol.*, 194:302-318 (1991)). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications or knockouts by specifically targeting the a kinetochore complex protein gene (e.g., CENH3, CENPC, MCM21, MIS12, NDC80, or NUF2) gene in vivo (see, generally, Grewal and Klar, *Genetics,* 146: 1221-1238 (1997) and Xu et al., *Genes Dev.,* 10:2411-2422 (1996)). Homologous recombination has been demonstrated in plants (Puchta et al., *Experientia,* 50:277-284 (1994); Swoboda et al., *EMBO J.,* 13:484-489 (1994); Offringa et al., *Proc. Natl. Acad. Sci. USA,* 90:7346-7350 (1993); and Kempin et al., *Nature,* 389:802-803 (1997)).

In applying homologous recombination technology to the genes of the invention, mutations in selected portions of an kinetochore complex protein gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA,* 91:4303-4307 (1994); and Vaulont et al., *Transgenic Res.,* 4:247-255 (1995) are conveniently used to increase the efficiency of selecting for altered CENH3 gene expression in transgenic plants. The mutated gene will interact with the target wild-type gene in such a way that homologous recombination and targeted replacement of the wild-type gene will occur in transgenic plant cells, resulting in suppression of kinetochore complex protein activity.

V. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature, e.g., Weising et al., *Ann. Rev. Genet.* 22:421-477 (1988). A DNA sequence coding for the desired polypeptide, for example the tailswap protein fusions as described herein and/or siRNA, antisense, or other silencing constructs, will be combined with transcriptional and translational initiation regulatory sequences which will direct the transcription of the sequence from the gene in the intended tissues of the transformed plant.

For example, a plant promoter fragment may be employed which will direct expression of the gene in all tissues of a regenerated plant. Alternatively, the plant promoter may direct expression of the polynucleotide of the invention in a specific tissue (tissue-specific promoters), organ (organ-specific promoters) or may be otherwise under more precise environmental control (inducible promoters). Examples of tissue-specific promoters under developmental control include promoters that initiate transcription only in certain tissues, such as fruit, seeds, flowers, pistils, or anthers. Suitable promoters include those from genes encoding storage proteins or the lipid body membrane protein, oleosin.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can also comprise, for example, a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Constitutive Promoters

A promoter, or an active fragment thereof, can be employed which will direct expression of a nucleic acid encoding a fusion protein of the invention, in all transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191 (1997)); the 1'- or 2'-promoter derived from T-DNA of *Agrobacterium tumefaciens* (see, e.g., Mengiste supra (1997); O'Grady, *Plant Mol. Biol.* 29:99-108) (1995)); the promoter of the tobacco mosaic virus; the promoter of Figwort mosaic virus (see, e.g., Maiti, *Transgenic Res.* 6:143-156) (1997)); actin promoters, such as the *Arabidopsis* actin gene promoter (see, e.g., Huang, *Plant Mol. Biol.* 33:125-139 (1997)); alcohol dehydrogenase (Adh) gene promoters (see, e.g., Millar, *Plant Mol. Biol.* 31:897-904 (1996)); ACT11 from *Arabidopsis* (Huang et al., *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al., *Plant Physiol.* 104:1167-1176 (1994)), GPc1 from maize (GenBank No. X15596, Martinez et al., *J. Mol. Biol.* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf, "Comparison of different constitutive and inducible promoters for the overexpression of transgenes in *Arabidopsis thaliana,*" *Plant Mol. Biol.* 29:637-646 (1995). Additional constitutive promoters include, e.g., the polyubiquitin gene promoters from *Arabidopsis thaliana*, UBQ3 and UBQ10, (Norris et al., *Plant Mol. Biol.* 21:895 (1993)), are also useful for directing gene expression.

Inducible Promoters

One can optionally use an inducible promoter to control (1) expression of an artificial micro RNA, siRNA, or other silencing polynucleotide, (2) and simultaneously turn on expression of the transgenic mutated (e.g., tailswap) protein, or (3) both (1) and (2). This would have the advantage of having a normal plant (e.g. one that might have higher fertility) until induction, which would then create gametes ready for inducing haploids.

Tissue-Specific Promoters

An alternative is to down-regulate the endogenous protein (e.g. by gene silencing) in a specific tissue (e.g., at least in the mature gametophytes (either pollen or embryo sac)) and to replace it only in this tissue with a specific promoter that drives expression of a tailswap protein. In some embodiments, the same tissue-specific promoter is used to drive an artificial micro RNA, siRNA, or other silencing polynucleotide and the rescuing tailswap-encoding transgene.

VI. Production of Transgenic Plants or Plant Cells

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci. USA* 82:5824 (1985). Biolistic transformation techniques are described in Klein et al., *Nature* 327:70-73 (1987).

*Agrobacterium tumefaciens*-mediated transformation techniques, including disarming and use of binary vectors, are well described in the scientific literature. See, for example Horsch et al., *Science* 233:496-498 (1984), and Fraley et al., *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased disease resistance compared to a control plant that was not transformed or transformed with an empty vector. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev. of Plant Phys.* 38:467-486 (1987).

The nucleic acids and encoded polypeptides of the invention can be used to confer the characteristics described herein, including the ability to generate haploid progeny, as described herein, on essentially any plant. Thus, the invention has use over a broad range of plants, including dicots or monocots, including e.g., species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panicum, Pennisetum, Persea, Pisum, Pyrus, Prunus, Raphanus, Secale, Senecio, Sinapis, Solanum, Sorghum, Trigonella, Triticum, Vitis, Vigna, and, Zea.

VII. Methods of Improved Breeding

Crossing plants that lack an endogenous kinetochore complex protein and express an active mutated kinetochore complex protein as described herein (e.g., a tailswap or other mutated CENH3 or non-CENH3 kinetochore complex protein) either as a pollen or ovule parent to a plant that expresses an endogenous kinetochore complex protein (e.g., CENH3, CENPC, MCM21, MIS12, NDC80, or NUF2 protein) will result in at least some progeny (e.g., at least 0.1%, 0.5%, 1%, 5%, 10%, 20% or more) that are haploid and comprise only chromosomes from the plant that expresses the kinetochore complex protein. Thus, the present invention allows for the generation of haploid plants having all of its chromosomes from a plant of interest by crossing the plant of interest with a plant transgenically expressing the mutated kinetochore complex protein and collecting the resulting haploid seed.

As noted above, the plant expressing an endogenous wildtype CENH3 protein can be crossed as either the male or female parent. One unique aspect of the present invention is that it allows for generation of a plant (or other organism) having only a male parent's nuclear chromosomes and a female parent's cytoplasm with associated mitochondria and plastids, when the tailswap parent is the male parent.

While plants lacking an endogenous CENH3 gene and expressing a mutated CENH3 protein made up of GFP-histone H3 tail-CENH3 histone-fold domain have limited male fertility, it has been found that plants lacking an endogenous CENH3 gene and expressing both a mutated CENH3 protein made up of GFP-histone H3 tail-CENH3 histone-fold domain and GFP-wildtype CENH3 results in plants with higher male fertility making them convenient for use as a male, as well as female, parent in crossing. In general, the invention provides for expression of two or more different mutated kinetochore complex proteins in a plant (e.g., a plant lacking expression of the corresponding endogenous kinetochore complex protein(s).

Once generated, haploid plants can be used for a variety of useful endeavors, including but not limited to the generation of doubled haploid plants, which comprise an exact duplicate copy of chromosomes. Such doubled haploid plants are of particular use to speed plant breeding, for example. A wide variety of methods are known for generating doubled haploid organisms from haploid organisms.

Somatic haploid cells, haploid embryos, haploid seeds, or haploid plants produced from haploid seeds can be treated with a chromosome doubling agent. Homozygous double haploid plants can be regenerated from haploid cells by contacting the haploid cells, including but not limited to haploid callus, with chromosome doubling agents, such as colchicine, anti-microtubule herbicides, or nitrous oxide to create homozygous doubled haploid cells.

Methods of chromosome doubling are disclosed in, for example, U.S. Pat. Nos. 5,770,788; 7,135,615, and US Patent Publication No. 2004/0210959 and 2005/0289673; Antoine-Michard, S. et al., *Plant Cell, Tissue Organ Cult.*, Cordrecht, the Netherlands, Kluwer Academic Publishers 48(3):203-207 (1997); Kato, A., Maize Genetics Cooperation Newsletter 1997, 36-37; and Wan, Y. et al., *Trends Genetics* 77: 889-892 (1989). Wan, Y. et al., *Trends Genetics* 81: 205-211 (1991), the disclosures of which are incorporated herein by reference. Methods can involve, for example, contacting the haploid cell with nitrous oxide, anti-microtubule herbicides, or colchicine. Optionally, the haploids can be transformed with a heterologous gene of interest, if desired.

Double haploid plants can be further crossed to other plants to generate F1, F2, or subsequent generations of plants with desired traits.

VIII. Non Plant Organisms

It is believed that the invention is also functional in non-plant organisms that do not have unmatched sex chromosomes. Those of skill in the art can thus generate a mutated kinetochore complex protein (including but not limited to a tailswap protein) based on a particular organism's kinetochore complex protein (e.g., CENH3, CENPC, MCM21, MIS12, NDC80, or NUF2) protein sequence and knockout the corresponding endogenous kinetochore complex protein gene as appropriate for that organisms. Exemplary non-plant organisms for which the invention is believed to be applicable include, but is not limited to, yeast and other fungi, as well as to animals that lack unmatched (e.g., XY) sex or other chromosomes for whom haploids are not viable.

EXAMPLES

The following examples are offered to illustrate, but not to limit the claimed invention.

Production of haploid plants that inherit chromosomes from only one parent can greatly accelerate plant breeding (Dunwell, J. M., *Plant Biotechnol J* in press; Forster, B. P. et al., *Trends Plant Sci* 12:368-75 (2007); Forster, B. P. & Thomas, W. T. B. in *Plant Breeding Reviews* (ed. Janick, J.) 57-88 (John Wiley & Sons, Inc., 2005)). Haploids generated from a heterozygous individual and converted to diploid create instant homozygous lines, bypassing generations of inbreeding. Two methods are generally used to produce haploids: First, cultured gametophyte cells may be regenerated into haploid plants (Guha, S. & Maheshwari, S. C., *Nature* 204:497 (1964)), but many species and genotypes are recalcitrant to this process (Forster, B. P. et al., *Trends Plant Sci* 12:368-75 (2007); Wedzony, M. et al. in *Advances in Haploid Production in Higher Plants* (eds. Touraev, A., Forster, B. P. & Jain, S. M.) 1-33 (Springer, 2009)). Second, haploids can be induced from rare interspecific crosses, in which one parental genome is eliminated after fertilization (Bains, G. S. & Howard, H. W., *Nature* 166:795 (1950); Barclay, I. R., *Nature* 256:410-411 (1975); Burk, L. G. et al., *Science* 206:585 (1979); Clausen, R. E. & Mann, M. C., *Proc Natl Acad Sci USA* 10:121-124 (1924); Hougas, H. W. & Peloquin, S. J., *Nature* 180:1209-1210 (1957); Kasha, K. J. & Kao, K. N., *Nature* 225:874-6 (1970)). The molecular basis for genome elimination is not understood, but one theory posits that centromeres from the two parent species interact unequally with the mitotic spindle, causing selective chromosome loss (Bennett, M. D. et al., *Chromosoma* 54:175-200 (1976); Finch, R. A., *Chromosoma* 88:386-393 (1983); Laurie, D. A. & Bennett, M. D., *Genome* 32:953-961 (1989)). Here it is shown that haploid *Arabidopsis thaliana* can be easily generated through seeds by manipulating a single centromere protein, the centromere-specific histone CENH3/CENP-A. When cenh3 null mutants expressing altered CENH3 proteins are crossed to wild type, chromosomes from the mutant are eliminated, producing haploid progeny. Haploids are spontaneously converted into fertile diploids through meiotic non-reduction, allowing their genotype to be perpetuated. Maternal and paternal haploids can be generated through reciprocal crosses. Centromere-mediated genome elimination has also been exploited to convert a natural tetraploid *Arabidopsis* into a diploid, reducing its ploidy to simplify breeding. As CENH3 is universal in eukaryotes, our method can be extended to produce haploids in any plant species.

Centromeres are the chromosomal loci that attach to spindle microtubules to mediate faithful inheritance of the genome during cell division. They are epigenetically specified by incorporation of CENH3 (CENP-A in humans, HTR12 in *A. thaliana* (Talbert, P. B. et al., *Plant Cell* 14:1053-66 (2002))), a histone H3 variant that replaces conventional H3 in centromeric nucleosomes (Henikoff, S. & Dalal, Y., *Curr Opin Genet Dev* 15:177-84 (2005))). Cenh3-1, an embryo-lethal null mutant in *A. thaliana* that allows us to completely replace native CENH3 with modified variants, was isolated. cenh3-1 plants complemented by transgenic green fluorescent protein-tagged CENH3 (GFP-CENH3) have a wild-type phenotype. cenh3-1 can also be rescued by "GFP-tailswap", a transgene in which the hyper-variable N-terminal tail domain of CENH3 was replaced with the tail of conventional H3, using the H3.3 variant (encoded by At1g13370). GFP-tailswap was tagged at its N-terminus with GF and contained the N-terminal tail of H3 fused to the histone fold domain of CENH3 as follows: H3 tail: MARTKQSARKSHGGKAPTKQLAT-KAARKSAPTTGGVKKPHRFR (SEQ ID NO:95) joined to the CENH3 histone fold domain:

(SEQ ID NO: 109)
PGTVALKEIRHFQKQTNLLIPAASFIREVRSITHMLAPPQINRWTAEALV

ALQEAAEDYLVGLFSDSMLCAIHARRVTLMRKDFELARRLGGKGRPW.

"GFP-tailswap" plants (cenh3-1 rescued by a GFP-tailswap transgene) showed accurate mitosis, as aneuploidy in somatic cells was not detected. However, GFP-tailswap plants were sterile upon flowering, indicating that they may have a specific defect in meiosis. GFP-tailswap was mostly male sterile, although it could be used as a pollen donor if many anthers were pooled. When crossed as the female to a wild type male, GFP-tailswap plants were 60-70% as fertile as wild type.

When GFP-tailswap was pollinated by wild type, several unusual phenotypes in F1 progeny were observed. First, 80-95% of fertilized ovules aborted early in development, yielding inviable seeds (Table 1).

TABLE 1

Haploid plants contain only the nuclear genome of their wild type parent.

| Cross | seeds/ silique | % normal seed | total plants analyzed | haploids (%) | diploids (%) | aneuploids (%) |
|---|---|---|---|---|---|---|
| WT Col-0 × WT Col-0 | 52 ± 6 (n = 23) | 99.5 | 224 | 0 (0) | 224 (100) | 0 (0) |
| GFP-tailswap × GFP-tailswap | 0.6 (n = 1206) | 80 | 213 | 0 (0) | 197 (92) | 16 (8) |
| GFP-tailswap × WT Col-0 | 32 ± 9 (n = 40) | 12 | 67 | 23 (34) | 23 (34) | 21 (32) |
| WT Col-0 × GFP-tailswap | nd | nd | 116 | 5 (4) | 99 (85) | 12 (11) |
| GFP-tailswap × WT Ler | 30 ± 4 (n = 22) | 23 | 127 | 32* (25) | 32 (25) | 63 (50) |
| GFP-tailswap × WT Ws-0 | 23 ± 5 (n = 14) | 8 | 22 | 10* (45) | 7 (32) | 5 (28) |
| GFP-tailswap × WT C24/Ler | 28 ± 5 (n = 13) | 30 | 117 | 34† (29) | 39 (33) | 44 (38) |
| C24/Ler male-sterile × GFP-tailswap | 22 ± 14 (n = 18) | 63 | 226 | 12† (5) | 206 (91) | 8 (4) |
| GFP-CENH3 × GFP-CENH3 | 53 ± 4 (n = 21) | 99 | 209 | 0 (0) | 209 (100) | 0 (0) |
| GFP-CENH3 × WT | 54 ± 7 (n = 18) | 67 | 164 | 8 (5) | 109 (66) | 47 (29) |
| WT × GFP-CENH3 | 48 ± 6 (n = 13) | 96 | 112 | 0 (0) | 108 (96) | 4 (4) |
| | | | | diploids (%) | triploids (%) | aneuploids (%) |
| GFP-tailswap × Wa-1 (tetraploid) | 21 ± 6 (n = 96) | 1.8 | 41 | 11 (27) | 0 | 30 (73) |

Second, while viable offspring were expected to be diploids heterozygous for cenh3-1 and hemizygous for the GFP-tailswap transgene, 10 out of 16 plants had only wild-type CENH3 and lacked GFP-tailswap. Each of these plants was sterile despite having a wild-type genotype. Furthermore, crossing GFP-tailswap to a quartet mutant male also yielded sterile F1 offspring (3/5 plants) that showed the quartet mutant phenotype of fused pollen, despite the fact that quartet is recessive and the GFP-tailswap parent was expected to transmit a wild-type QUARTET allele. These striking observations suggested that sterile progeny had lost chromosomes from their GFP-tailswap mother, and thus had fewer chromosomes than diploid A. thaliana (2n=10). The karyotype of these plants was examined and found them to be haploids containing only five chromosomes.

As centromeres control chromosome inheritance, it was reasoned that chromosomes that entered the zygote containing the GFP-tailswap variant of CENH3 would be missegregated and lost, creating haploid plants with chromosomes only from their wild type parent. To confirm this, GFP-tailswap plants (in the Col-0 accession) were crossed to several polymorphic accessions and genotyped F1 haploids for markers on all five A. thaliana chromosomes (Table 1). Regardless of the wild-type parent used, haploid plants invariably contained only wild-type chromosomes (paternal haploids), indicating that the GFP-tailswap genome was eliminated (a total of 42 haploids were genotyped). Further, our results show that the process of inducing haploids by centromere-mediated genome elimination is independent of the genotype of the wild-type parent.

Genome elimination induced by CENH3 alterations is not specific to the GFP-tailswap transgene. Crossing cenh3-1 mutants complemented by GFP-CENH3 to wild type also yielded haploid plants, but at a lower frequency than GFP-tailswap (Table 1). Haploid progeny from self-fertilized GFP-tailswap or GFP-CENH3 plants were not observed (Table 1). Our results suggest that general perturbations in centromere structure are sufficient to impede chromosome segregation during zygotic mitosis, creating a haploid embryo when chromosomes containing mutant CENH3 compete with wild type on the same spindle.

Haploids are efficiently generated from a GFP-tailswap x wild type cross, comprising 25-45% of viable offspring (Table 1). Remaining progeny were either diploid hybrids, or aneuploid hybrids showing the developmental phenotypes typical of A. thaliana plants with more than 10 chromosomes (Henry, I. M. et al., Genetics 170:1979-88 (2005)) (Table 1). Aneuploidy might also account for the high level of seed abortion in a GFP-tailswap x wild type cross, as some embryos with unbalanced karyotypes may be inviable.

Uniparental haploids may contain the genome of either their female or male parent. Haploids were also obtained by crossing a wild-type female to GFP-tailswap as the pollen donor (Table 1). In this case, haploid progeny are purely maternal in origin. Genotyping of the plastid genome showed that both maternal and paternal haploids contained the cytoplasm of their maternal parent. Either maternal or paternal haploids were made by using GFP-tailswap plants as the male or female parent respectively in a cross to wild type. The proportion of haploids and aneuploids was much lower if a wild-type female was crossed to a GFP-tailswap male (Table 1). It is hypothesized that if CENH3 is expressed earlier in development from the maternal (wild type) genome, wild-type CENH3 could be incorporated into paternal chromosomes derived from GFP-tailswap, preventing genome elimination in a wild type x GFP-tailswap cross.

Haploid A. thaliana plants are morphologically similar to diploids, but are comparatively smaller in size. Early in vegetative development, haploids have narrower rosette leaves. After bolting, haploids produce more leaves from secondary meristems. Haploid flowers are smaller than diploid flowers, following the general trend that flower size increases with ploidy in A. thaliana. Haploids are generally sterile. They contain a single copy of each chromosome and cannot undergo homologue pairing in meiosis, resulting in gametes that do not contain a full complement of chromosomes. Maternal and paternal haploid plants had similar adult morphology. This is consistent with the fact that all documented imprinting in A. thaliana occurs in the short-lived endosperm, a structure confined to the seed.

To exploit the potential of haploids in crop improvement, their genome should be doubled to generate fertile diploids (doubled haploids) (Forster, B. P., et al. Trends Plant Sci 12:368-75 (2007)). A close inspection of A. thaliana haploids revealed that random siliques had one or two seeds. Each haploid plant yielded a total of 50-2500 seeds depending on the wild-type parental accession (Table S1).

TABLE S1

Number of spontaneous diploid seeds produced by A. thaliana haploids

| Plant | Col-0 | Ler | Ws-0 |
| --- | --- | --- | --- |
| 1 | 54 | 951 | 1662 |
| 2 | 68 | 2115 | 293 |
| 3 | 91 | 352 | 2343 |
| 4 | 214 | 520 | 1532 |
| 5 | 349 | 325 | 2679 |
| 6 | 421 | 101 | 215 |
| 7 | 537 | 219 | 913 |
| 8 | 121 | 1013 | |
| 9 | 134 | 424 | |
| 10 | 85 | 630 | |
| 11 | 99 | 1346 | |
| Mean | 197.5454545 | 726.9090909 | 1376.714286 |
| Standard deviation | 164.1294389 | 594.8035734 | 955.1793399 |

A majority (95%) of these seeds appeared normal and gave rise to fertile diploids. To address how haploids gave rise to diploid seeds, chromosome segregation during haploid male meiosis was analyzed. During prophase I the five chromosomes remained separate as univalents, which aligned properly in metaphase I. In anaphase I, most meiocytes showed unbalanced reductional segregation (4-1, 3-2, etc.). Meiosis II in these cases gave rise to aneuploid tetrads. In a small minority of anaphase I cells, the 5 univalents migrated towards one pole (5-0 segregation). In subsequent meiosis II, sister chromatids segregated equally, giving rise to haploid dyads and viable gametes. Thus, it is assumed that occasional non-reduction during both male and female haploid meiosis yielded doubled haploids through self-fertilization, consistent with previous observations (Chase, S. S., Botanical Review 35:117-167 (1969); Jauhar, P. P. et al., Crop Science 40:1742-1749 (2000)). In rare instances, spontaneous chromosome doubling in somatic tissues of haploid A. thaliana plants was observed; a side branch from the main inflorescence (2 out of 78 plants) or a random silique (6 out of 78 plants) showed a complete seed set. The microtubule polymerization inhibitor colchicine also induces somatic chromosome doubling in haploid A. thaliana, and diploid shoots that regenerate after treatment show complete seed set. Although A. thaliana haploids have been produced through anther culture (Avetisov, V. A., Genetika, 12:17-25

(1976)), spontaneous diploids recovered in these experiments were reportedly sterile (Scholl, R. & Amos, J. A., *Z Pflanzenphysiol* 96:407-414 (1980)), and the method has not been widely adopted. The ease of generating haploids through seed by altering CENH3, and of converting haploids into diploids allows large scale generation of doubled haploids in *A. thaliana*.

Many commercial crops are polyploid (Udall, J. A. & Wendel, J. F., *Crop Sci,* 46:S3-S14 (2006)), but genetic analysis of polyploids is tedious. Reducing the ploidy of these crops will facilitate easy breeding, so it was tested whether centromere-mediated genome elimination could scale down a tetraploid to diploid. *A. thaliana* is predominantly diploid, but tetraploid accessions exist (Henry, I. M. et al., *Genetics* 170:1979-88 (2005)). GFP-tailswap was crossed to the natural tetraploid Warschau-1 (Wa-1), and although over 98% of seed were aborted, viable F1 progeny included synthetic diploid plants containing only Wa-1 chromosomes (Table 1). Therefore, it is possible to extend centromere-mediated genome elimination to halve the ploidy of polyploids.

Centromere incompatibility was previously hypothesized to cause selective genome elimination in interspecies crosses (Bennett, M. D. et al., *Chromosoma* 54:175-200 (1976); Finch, R. A., *Chromosoma* 88:386-393 (1983); Laurie, D. A. & Bennett, M. D., *Genome* 32:953-961 (1989); Heppich, S. et al., *Theor Appl Genet* 61:101-104 (1982); Jin, W. et al., *Plant Cell* 16:571-81 (2004)), but it was not known how centromeres could be manipulated to achieve this. It was established a practical basis for engineering genome elimination by altering CENH3, a protein essential for centromere function in all eukaryotes. The fact that haploids were produced with both GFP-tailswap and GFP-CENH3 transgenes suggests that multiple different alterations to the protein may induce genome elimination in other plants. *A. thaliana* plants that coexpress wild-type and GFP-tailswap or GFP-CENH3 proteins do not act as a haploid inducer. Therefore, our method currently relies on replacing native CENH3 with an altered variant. A cenh3 mutation or a gene silencing method such as RNA interference could be used to reduce or eliminate endogenous CENH3 function in a novel species.

Haploid inducing lines have been described in the grasses (Coe, E. H., *American Naturalist* 93:381-382 (1959); Hagberg, A. & Hagberg, G., *Hereditas* 93:341-343 (1980); Kermicle, J. L., *Science* 166:1422-1424 (1969)), but their genetic basis is not known, except for maize indeterminate gametophyte (ig) (Evans, M. M., *Plant Cell* 19:46-62 (2007)). The effect of ig may be limited to maize, because mutations in the *A. thaliana* ig orthologue AS2 do not phenocopy its effect (Ori, N. et al., *Development* 127:5523-32 (2000)). Our process has key advantages over current methods for producing haploid plants. 1) No tissue culture is needed, removing a major source of genotype dependence. 2) The same inducer produces maternal and paternal haploids. 3) Crossing a cenh3 mutant as the female transfers the nuclear genome of the male parent into a heterologous cytoplasm. This could accelerate production of cytoplasmic male sterile lines for making hybrid seed. 4) Genome elimination occurs between parents that are isogenic except for CENH3 alterations, avoiding fertility barriers inherent to wide crosses.

Genome elimination induced by changes in CENH3 probably occurs during the first few zygotic mitoses, when centromeres from the two parents are loaded with different populations of CENH3 proteins. Expression of both wild-type and mutant CENH3 genes in subsequent cell cycles should rapidly equalize the amount of the two proteins in individual centromeres. Zygotic mitosis is normal in GFP-tailswap and in GFP-CENH3 plants, because haploids from self-fertilized plants were not observed. Furthermore, GFP-CENH3 plants have a completely wild type phenotype. Subtle differences in centromere DNA binding, kinetochore assembly, or coupling to spindle microtubules may be sufficient to slow the segregation of chromosomes containing altered CENH3, resulting in genome elimination. Cell cycle checkpoints in plants must be relaxed enough to allow wild type and mutant chromosomes to segregate differentially, and presumably to permit cytokinesis without complete chromosome segregation. The precise mechanism of genome elimination in our experiments remains unknown.

Centromere DNA sequences and the CENH3 protein both evolve rapidly, and centromere differences have been proposed to create species barriers (Henikoff, S. et al., *Science* 293:1098-102 (2001)). Although our experiments used tagged proteins, they indicate that changes in CENH3 can induce specific chromosome loss in a hybrid zygote.

Methods Summary
Plant Materials.

cenh3-1 is a G-to-A transition at nucleotide 161 relative to ATG=+1, and mutates a conserved splice acceptor in the second intron. GFP-CENH3 and GFP-tailswap transgenes contained an N-terminal GFP, and used the endogenous CENH3 promoter and terminator. The location of the GFP-tailswap transgene was determined by TAIL-PCR, allowing us to determine whether the transgene was homozygous or hemizygous. The C24/Ler male sterile line was a gift from Dr Luca Comai (University of California, Davis). Male sterility was conferred by the A9-barnase transgene. Plants were grown under 16 hrs of light/8 hours of dark at 20 degrees C.

Genomic DNA Preparation and Genotyping.

Genomic DNA preparation and PCR genotyping were performed using standard methods.

Cytogenetic Analysis.

To analyze meiotic progression and to determine ploidy, mitotic and meiotic chromosome spreads from anthers were prepared according to published protocols.

Plant Materials cenh3-1 cenh3-1 was isolated by the TILLING procedure (Comai, L. & Henikoff, S., *Plant J* 45:684-94 (2006)). The TILLING population was created by mutagenizing *Arabidopsis thaliana* in the Col-0 accession with ethylmethanesulfonate, using standard protocols. Cenh3-1 was isolated by TILLING using the CEL1 heteroduplex cleavage assay, with PCR primers specific for the CENH3/HTR12 gene.

cenh3-1 is predicted to disrupt normal splicing of CENH3, because it mutates a conserved splice acceptor site at the beginning of the second coding exon. Translation of an mRNA containing the first coding exon spliced to an incorrect location within CENH3 is predicted to yield only 18 correct amino acids. As the histone-fold domain of CENH3 begins at amino acid residue 82, it is believed that cenh3-1 is a null allele (this is supported by its embryo-lethal phenotype).

Cloning of the GFP-CENH3 and GFP-tailswap transgenes, and construction of the complemented cenh3-1 GFP-CENH3 and cenh3-1 GFP-tailswap lines are described elsewhere (Ravi, Comai, Sundaresan, Chan et al, manuscript in preparation). Primer sequences and full details are available on request.

To cross wild type as the female to GFP-tailswap as the male, a dissecting microscope was used to directly observe pollen deposition on the stigma (GFP-tailswap is mostly male-sterile). The amount of viable pollen in individual flowers of GFP-tailswap varies. Flowers that clearly showed higher amounts of pollen were selected, and pollinated with more than 60 anthers (10 GFP-tailswap flowers) per wild type stigma to achieve the seed set reported in Table 1. Using an optivisor (magnifying lens) and approximately 12 anthers (2 GFP-tailswap flowers) per wild type stigma, a much lower seed set per silique was obtained.

The percentage of normal seeds was determined by visual inspection using a dissecting microscope.

Seed from GFP-tailswap x wild type crosses were sown on 1×MS plates containing 1% sucrose to maximize germination efficiency, particularly of seed that had an abnormal appearance. Late germinating seeds were frequently haploid.

The quartet mutant used was qrt1-2 (Francis, K. E. et al., *Plant Physiol* 142:1004-13 (2006)).

Male sterility in the C24/Ler line was conferred by the A9-barnase transgene (Bushell, C. et al., *Plant Cell* 15:1430-42 (2003); Paul, W. et al., *Plant Mol Biol* 19:611-22 (1992)).

In the GFP-tailswap x Wa-1 experiment, progeny from the GFP-tailswap x Wa-1 cross that contained only Wa-1 chromosomes were confirmed as diploid using chromosome spreads. Plants that were heterozygous for some chromosomes (Col-0 and Wa-1 markers) and homozygous for other chromosomes (Wa-1 markers only) were scored as aneuploid. Triploid offspring (heterozygous for markers on all chromosomes) were not found. A subset of plants were further karyotyped by means of chromosome spreads to confirm aneuploidy.

Cytogenetic Analysis.

Mitotic and meiotic chromosome spreads from anthers were prepared according to published protocols (Ross, K. J. et al., *Chromosome Res* 4:507-16 (1996)).

Colchicine Treatment

Colchicine treatment of developing haploid plants used a previously published protocol with minor modifications (Josefsson, C. et al., *Curr Biol* 16:1322-8 (2006)). A solution of 0.25% colchicine, 0.2% Silwet was prepared, and a 20 µL drop was placed on the meristem prior to bolting. Plants became transiently sick after colchicine treatment. Upon recovery, fertile inflorescences appeared from secondary meristems indicating successful chromosome doubling. Haploid plants can also be treated after bolting, although the rate of success is considerably lower.

Example 2

GFP-Maizetailswap Creates F1 Haploids in a Cross to Wild Type

A chimera was created in which the *A. thaliana* CENH3 tail from CENH3 is replaced with the CENH3 tail domain (SEQ ID NO:102) from maize (*Zea mays*), thereby generating a fusion of the maize CENH3 tail and *A. thaliana* CENH3 histone-fold domain, and transformed the fusion into cenh3-1 heterozygotes. As expected, this GFP-maize-tailswap protein was targeted to kinetochores and rescued the embryo-lethal phenotype of cenh3-1. Complemented plants were more sterile than GFP-tailswap complemented plants, but had limited fertility when used as the female. When cenh3-1 GFP-maizetailswap females were crossed to wild-type males, 2 haploids, 3 diploids and 5 aneuploids were found among a total of 10 F1 progeny.

mCherry-Tailswap Creates F1 Haploids in a Cross to Wild Type

A transgene was created in which the GFP tag in GFP-tailswap was replaced with an N-terminal mCherry tag (mCherry (SEQ ID NO:105) is a monomeric version of the red fluorescent protein DsRed). From N-terminus to C-terminus, this protein contains mCherry, the tail domain of *Arabidopsis thaliana* H3.3, and the histone fold domain of *Arabidopsis thaliana* CENH3. mCherry-tailswap transgenes were transformed into cenh3-1 heterozygotes. When complemented cenh3-1 mCherry-tailswap plants were crossed as female to wild-type male, 1 haploid, 6 aneuploids and 4 diploids were observed from 11 F1 progeny.

The mCherry-tailswap construct was made as a CP 169 vector pCAMBIA 1300 with an HTR promoter. The insert included a Mlu I site followed by the N terminal mcherry Sal I XbaI followed by HTR12 terminator. The H3 Tailswap fragment was synthesized by overlapping PCR and digested with SalI+Xba I and cloned into CP169 to make the mcherrytailswap construct.

A Tailswap Transgene with No GFP Tag Complements a Cenh3-1 Mutation. Complemented Plants Create F1 Haploids in a Cross to Wild Type A transgene was created in which the GFP tag in GFP-tailswap was removed. From N-terminus to C-terminus, this protein contains the tail domain of *Arabidopsis thaliana* H3.3, and the histone fold domain of *Arabidopsis thaliana* CENH3. tailswap transgenes were transformed into cenh3-1 heterozygotes. When complemented cenh3-1 tailswap plants were crossed as female to wild-type male, 4 haploids, 27 aneuploids and 67 diploids were observed from 95 F1 progeny.

Co-Expression of Different CENH3 Variants Creates Desirable Properties in a Genome Elimination Strain.

The previously described GFP-tailswap plant (cenh3-1 mutant plants rescued by a GFP-tailswap transgene) is a very efficient haploid inducer, but is difficult to cross as the pollen donor because it is mostly male sterile. GFP-CENH3 (cenh3-1 mutant plants rescued by a GFP-CENH3 transgene) is a weaker haploid inducer but is much more fertile. It was found that co-expression of GFP-CENH3 and GFP-tailswap in cenh3-1 plants would produce more viable pollen than GFP-tailswap, yet still induce genome elimination when these plants were crossed to wild-type diploid or tetraploids. Indeed, cenh3-1 carrying both GFP-CENH3 and GFP-tailswap transgenes (GEM; Genome Elimination caused by a Mix of cenh3 variants) plants produced ample pollen for crosses, although pollen viability was still lower than wild-type.

Crossing GEM females to wild-type males yielded 2 F1 haploids from 50 progeny. When wild-type females were crossed to GEM males, one haploid was found from 104 progeny.

GEM plants are a major improvement over GFP-tailswap or GFP-CENH3 when the wild-type parent is a tetraploid that has diploid gametes. When GEM plants were crossed as male or female to tetraploid wild-type, chromosomes from the GEM parent were eliminated in a subset of F1 progeny (Table 3). GEM is fertile as either male or female, and shows efficient genome elimination when crossed to a tetraploid parent with diploid gametes.

TABLE 2

Crosses between GEM and diploid wild-type plants produce genome elimination.

| cross (♀ × ♂) | Total plant analysed | Triploid | Aneuploid | Uniparental* diploid plants |
|---|---|---|---|---|
| Wild type 4n × GEM | 85 | 53 | 27 | 5 |
| GEM × Wild type 4n | 84 | 12 | 57 | 15 |

TABLE 3

Crosses between GEM and tetraploid wild-type plants produce genome elimination.

| cross (♀ × ♂) | Total plant analysed | Diploid | Aneuploid | Uniparental* haploid plants |
|---|---|---|---|---|
| Wild type 2n × GEM | 104 | 62 | 18 | 1 |
| GEM × Wild type 2n | 50 | 36 | 12 | 2 |

Methods for GFP-Maizetailswap Construction

Maize tailswap CENH3 transgene was constructed by fusing in frame the Maize CENH3 N-terminal tail (corresponding to 1-61aa) and *Arabidopsis* CENH3 histone fold domain (corresponding to 82-179 aa) by overlapping PCR. The maize N terminal tail domain (206 bp) was amplified from maize cDNA using the primer combinations CP 384 (5'-NNNNgtcgacATGGCTCGAACCAAGCACCA-3' (SEQ ID NO:110), SalI site is italiziced) and CP 572 (5'-CAACGGTTCCTGGCCTCCAGCGGTGGC-3' (SEQ ID NO:111)). The *Arabidopsis* HFD (950 bp) was amplified from genomic DNA using primer combinations CP 571 (5'-GCCACCGCTGGAGGCCAGGAACCGTTG-3' (SEQ ID NO:112)) and CP 375 (5'-NNNNtctagaTCAC-CATGGTCTGCCTTTTCCTCC-3' (SEQ ID NO:113), XbaI site is italiziced). The resultant fragments were gel purified and used as a template to fuse them in an overlapping PCR using primer combinations CP 384 and CP 375. The resultant 1.15 kb fragment is cloned as a SalI-XbaI fragment in a binary vector CP 93 (derived from pCAMBIA 1300). The vector CP 93 contains GFP coding sequence upstream in frame with SalI-XbaI site and its expression is controlled by the 5' and 3' regulatory sequences of *Arabidopsis* CENH3 gene.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A transgenic plant comprising a heterologous transgene expression cassette, the expression cassette comprising a promoter operably linked to a polynucleotide encoding a polypeptide comprising a CENH3 tail domain linked to a heterologous CENH3 histone-fold domain, wherein the CENH3 tail domain and the CENH3 histone-fold domain are from different species.

2. The transgenic plant of claim 1, wherein one or two alleles of the endogenous CENH3 genomic coding sequence of the plant is inactivated or knocked out.

3. The transgenic plant of claim 1, wherein all alleles of the endogenous CENH3, genomic coding sequence of the plant are inactivated or knocked out.

4. The transgenic plant of claim 3, wherein the plant, when crossed with a wildtype diploid plant, generates at least 0.1% haploid progeny.

5. The transgenic plant of claim 1, wherein the polypeptide further comprises a further heterologous amino acid sequence of at least 5 amino acids at an amino terminus of the polypeptide.

6. The transgenic plant of claim 1, wherein the CENH3 histone-fold domain is at least 95% identical to at least one of SEQ ID NOs: 49-94.

7. The transgenic plant of claim 1, wherein the CENH3 histone-fold domain is from the same species as the transgenic plant.

8. An isolated polynucleotide encoding the polypeptide of claim 1.

9. A method of generating an F1 progeny plant having half the ploidy of a parent plant expressing an endogenous CENH3 protein, the method comprising,
   crossing the parent plant to the plant of claim 3; and
   selecting F1 progeny generated from the crossing step having half the ploidy of the parent plant.

10. The method of claim 8, wherein the parent plant is the pollen parent.

11. The method of claim 8, wherein the parent plant is the ovule parent.

12. The method of claim 8, wherein the parent plant is diploid and the selected F1 progeny is haploid and the method further comprises converting at least one selected haploid plant into a doubled haploid plant.

13. A method of making the transgenic plant of claim 1, comprising, transforming plant cells with a nucleic acid comprising the expression cassette; and selecting transformants comprising the nucleic acid, thereby making the transgenic plant.

* * * * *

SEQUENCE LISTING

```
<160> NUMBER OF SEQ ID NOS: 114

<210> SEQ ID NO 1
<211> LENGTH: 136
<212> TYPE: PRT
<213> ORGANISM: Arabidopsis thaliana
<220> FEATURE:
<223> OTHER INFORMATION: thale cress histone 3.3 (H3.3), histone 3-like
      1

<400> SEQUENCE: 1

Met Ala Arg Thr Lys Gln Ser Ala Arg Lys Ser His Gly Gly Lys Ala
1               5                   10                  15

Pro Thr Lys Gln Leu Ala Thr Lys Ala Ala Arg Lys Ser Ala Pro Thr
                20                  25                  30

Thr Gly Gly Val Lys Lys Pro His Arg Phe Arg Pro Gly Thr Val Ala
            35                  40                  45

Leu Arg Glu Ile Arg Lys Tyr Gln Lys Ser Thr Glu Leu Leu Asn Arg
        50                  55                  60

Lys Leu Pro Phe Gln Arg Leu Val Arg Glu Ile Ala Gln Asp Phe Lys
65                  70                  75                  80

Thr Asp Leu Arg Phe Gln Ser His Ala Val Leu Ala Leu Gln Glu Ala
                85                  90                  95

Ala Glu Ala Tyr Leu Val Gly Leu Phe Glu Asp Thr Asn Leu Cys Ala
                100                 105                 110

Ile His Ala Lys Arg Val Thr Ile Met Pro Lys Asp Val Gln Leu Ala
            115                 120                 125

Arg Arg Ile Arg Ala Glu Arg Ala
        130                 135

<210> SEQ ID NO 2
<211> LENGTH: 136
<212> TYPE: PRT
```

<213> ORGANISM: Homo sapiens
<220> FEATURE:
<223> OTHER INFORMATION: human histone 3.3 (H3.3), H3 histone, family 3A
      (H3F3A), H3 histone, family 3B (H3F3B)

<400> SEQUENCE: 2

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 3
<211> LENGTH: 125
<212> TYPE: PRT
<213> ORGANISM: Physcomitrella patens
<220> FEATURE:
<223> OTHER INFORMATION: moss histone H3

<400> SEQUENCE: 3

Met Ala Arg Arg Lys Thr Thr Pro Val His Gly Asn His Arg Ala Ser
1               5                   10                  15

Thr Ser Ser Val Gly Gly Ala Ala Val Arg Pro Arg Lys Pro His Arg
            20                  25                  30

Trp Arg Pro Gly Thr Lys Ala Leu Gln Glu Ile Arg His Tyr Gln Lys
        35                  40                  45

Thr Cys Asp Leu Leu Ile Pro Arg Leu Pro Phe Ala Arg Tyr Val Lys
    50                  55                  60

Glu Ile Thr Met Met Tyr Ala Ser Asp Val Ser Arg Trp Thr Ala Glu
65                  70                  75                  80

Ala Leu Thr Ala Leu Gln Glu Ala Thr Glu Asp Tyr Met Cys His Leu
                85                  90                  95

Phe Glu Asp Thr Asn Leu Cys Ala Ile His Ala Lys Arg Val Thr Ile
            100                 105                 110

Met Pro Lys Asp Leu Gln Leu Ala Arg Arg Leu Arg Gly
        115                 120                 125

<210> SEQ ID NO 4
<211> LENGTH: 164
<212> TYPE: PRT
<213> ORGANISM: Pinus taeda
<220> FEATURE:
<223> OTHER INFORMATION: loblolly pine histone H3

<400> SEQUENCE: 4

Met Val Arg Arg Lys Thr Val Pro Pro Arg Lys Lys Ser Gly Ser Gly

```
            1               5                  10                 15
          Asn Ala Ala Ser Thr Ser Gly Val Gly Val Ser Thr Pro Gly Ser Ala
                      20                  25                 30

Gly Glu Arg Gly Glu Arg Arg Gly Ser Ala Arg Leu Ala Ser Thr Pro
                      35                  40                 45

Gly Ser Asp Ala Ser Pro Ser Ala Pro Ser Gly Arg Lys Pro His Arg
                      50                  55                 60

Phe Arg Pro Gly Thr Val Ala Leu Arg Glu Ile Lys Arg Tyr Gln Lys
           65                  70                  75                 80

Ser Phe Glu Leu Leu Ile Pro Ser Leu Pro Phe Ala Arg Ile Val Arg
                            85                  90                 95

Glu Leu Thr Met Tyr Tyr Ser Gln Val Val Ser Arg Trp Ala Ala Glu
                           100                 105                110

Ala Leu Val Ala Leu Gln Glu Ala Ala Glu Asp Tyr Ile Val His Leu
                           115                 120                125

Phe Glu Asp Thr Asn Leu Cys Ala Ile His Ala Lys Arg Val Thr Ile
                           130                 135                140

Met Pro Arg Asp Leu Arg Leu Ala Arg Arg Leu Arg Gly Gly Gly Leu
          145                 150                 155                160

Asp Arg Pro Trp

<210> SEQ ID NO 5
          <211> LENGTH: 177
          <212> TYPE: PRT
          <213> ORGANISM: Boechera holboellii
          <220> FEATURE:
          <223> OTHER INFORMATION: Holboell's rockcress CENH3

<400> SEQUENCE: 5

Met Ala Arg Thr Lys His Leu Ala Thr Arg Ser Arg Pro Arg Asn Gln
          1               5                  10                 15

Thr Asp Ala Thr Ala Ser Ser Ser Gln Ala Ala Gly Pro Ser Thr Asn
                      20                  25                 30

Pro Thr Thr Arg Gly Ser Glu Gly Glu Asp Ala Ala Gln Glu Thr Thr
                      35                  40                 45

Pro Thr Thr Ser Pro Ala Thr Gly Arg Lys Lys Gly Ala Lys Arg Ala
                      50                  55                 60

Arg Tyr Ala Arg Pro Gln Gly Ser Gln Lys Lys Pro Tyr Arg Tyr Lys
           65                  70                  75                 80

Pro Gly Thr Val Ala Leu Arg Glu Ile Arg Tyr Phe Gln Lys Ser Ile
                            85                  90                 95

Asn Leu Leu Ile Pro Ala Ala Ser Phe Ile Arg Gln Val Arg Ser Ile
                           100                 105                110

Thr His Ala Leu Ala Pro Pro Gln Ile Thr Arg Trp Thr Ala Glu Ala
                           115                 120                125

Leu Val Ala Leu Gln Glu Ala Ala Glu Asp Tyr Leu Val Gly Leu Phe
                           130                 135                140

Ser Asp Ser Met Leu Cys Ala Ile His Ala Arg Arg Val Thr Leu Met
          145                 150                 155                160

Arg Lys Asp Phe Glu Leu Ala Arg Arg Leu Gly Gly Lys Gly Arg Pro
                           165                 170                175

Trp

<210> SEQ ID NO 6
          <211> LENGTH: 177
```

```
<212> TYPE: PRT
<213> ORGANISM: Boechera stricta
<220> FEATURE:
<223> OTHER INFORMATION: Drummond's rockcress CENH3

<400> SEQUENCE: 6
```

Met Ala Arg Thr Lys His Leu Ala Thr Arg Ser Arg Pro Arg Asn Trp
1               5                   10                  15

Thr Asp Ala Thr Ala Ser Ser Ser Gln Ala Ala Gly Pro Thr Thr Asn
                20                  25                  30

Pro Thr Thr Arg Gly Ser Glu Gly Glu Asp Ala Ala Gln Glu Pro Thr
            35                  40                  45

Pro Thr Thr Ser Pro Ala Thr Gly Arg Lys Lys Gly Ala Lys Arg Ala
50                  55                  60

Arg Tyr Ala Arg Pro Gln Gly Ser Gln Lys Lys Pro Tyr Arg Tyr Lys
65                  70                  75                  80

Pro Gly Thr Val Ala Leu Arg Glu Ile Arg His Phe Gln Lys Ser Ile
                85                  90                  95

Asn Leu Leu Ile Pro Ala Ala Ser Phe Ile Arg Gln Val Arg Ser Ile
                100                 105                 110

Thr His Ala Leu Ala Pro Pro Gln Ile Thr Arg Trp Thr Ala Glu Ala
            115                 120                 125

Leu Val Ala Leu Gln Glu Ala Ala Glu Asp Tyr Leu Val Gly Leu Phe
130                 135                 140

Ser Asp Ser Met Leu Cys Ala Ile His Ala Arg Arg Ile Thr Leu Met
145                 150                 155                 160

Arg Lys Asp Phe Glu Leu Ala Arg Arg Leu Gly Gly Lys Gly Arg Pro
                165                 170                 175

Trp

```
<210> SEQ ID NO 7
<211> LENGTH: 180
<212> TYPE: PRT
<213> ORGANISM: Lepidum virginicum
<220> FEATURE:
<223> OTHER INFORMATION: Virginia pepperweed centromeric histone H3-like
      protein (CENH3)

<400> SEQUENCE: 7
```

Met Ala Arg Thr Lys Arg Tyr Ala Ser Arg Pro Gln Arg Pro Arg Asn
1               5                   10                  15

Gln Thr Asp Val Thr Val Pro Ser Ser Pro Ala Ala Gly Pro Ser Thr
                20                  25                  30

Asn Pro Thr Arg Arg Asp Ser Glu Gly Glu Gly Gly Asp Asp Ala Gln
            35                  40                  45

Gln Thr Val Pro Thr Thr Ser Pro Ala Ser Ile Ser Lys Lys Ala Ser
50                  55                  60

Lys Lys Asn Arg Lys Ala Thr Pro Gln Ser Ser Lys Lys Lys Thr Tyr
65                  70                  75                  80

Arg Tyr Lys Pro Gly Thr Val Ala Leu Arg Glu Ile Arg His Phe Gln
                85                  90                  95

Lys Ser Thr His Leu Leu Ile Pro Ala Ala Ala Phe Ile Arg Glu Val
                100                 105                 110

Arg Cys Ile Thr Gln Ala Val Ala Pro Pro Gln Ile Ser Arg Trp Thr
            115                 120                 125

Ala Glu Ala Leu Val Ala Leu Gln Glu Ala Ala Glu Asp Tyr Val Val
130                 135                 140

-continued

```
Gly Leu Leu Ser Asp Ser Met Leu Cys Ala Ile His Ala Arg Arg Val
145                 150                 155                 160

Thr Leu Met Arg Lys Asp Phe Glu Leu Ala Arg Arg Leu Gly Gly Lys
                165                 170                 175

Gly Arg Pro Trp
            180

<210> SEQ ID NO 8
<211> LENGTH: 172
<212> TYPE: PRT
<213> ORGANISM: Cardamine flexuosa
<220> FEATURE:
<223> OTHER INFORMATION: woodland bittercress centromeric histone H3-
      like protein (CENH3)

<400> SEQUENCE: 8

Met Ala Arg Thr Lys His Phe Pro Asn Arg Thr Arg Pro Arg Asn Gln
1               5                   10                  15

Thr Asp Ala Thr Thr Pro Ala Ala Gly Pro Ser Thr Arg Thr Thr Arg
            20                  25                  30

Ala Asn Gln Gly Glu Glu Thr Gln Gln Thr Asn Pro Thr Thr Ser Pro
        35                  40                  45

Ala Thr Ser Lys Lys Lys Gly Ala Lys Arg Thr Arg Arg Asp Met Pro
    50                  55                  60

Gln Gly Ser Gln Lys Lys Pro Tyr Arg Tyr Lys Pro Gly Thr Val Ala
65                  70                  75                  80

Leu Arg Glu Ile Arg His Phe Gln Lys Ser Thr Asn Leu Leu Ile Pro
                85                  90                  95

Ala Ala Ser Phe Ile Arg Gln Val Arg Ser Ile Thr Gln Met Tyr Ala
            100                 105                 110

Pro Pro Gln Ile Asn Arg Trp Thr Ala Glu Ala Leu Val Ala Leu Gln
        115                 120                 125

Glu Ala Ala Glu Asp Tyr Leu Val Gly Leu Phe Ser Asp Ser Met Leu
    130                 135                 140

Cys Ala Ile His Ala Arg Arg Val Thr Leu Met Arg Lys Asp Phe Glu
145                 150                 155                 160

Leu Ala Arg Arg Leu Gly Gly Lys Gly Arg Pro Trp
                165                 170

<210> SEQ ID NO 9
<211> LENGTH: 139
<212> TYPE: PRT
<213> ORGANISM: Hordeum vulgare
<220> FEATURE:
<223> OTHER INFORMATION: barley CENH3

<400> SEQUENCE: 9

Met Ala Arg Thr Lys Lys Thr Val Ala Ala Lys Glu Lys Arg Pro Pro
1               5                   10                  15

Cys Ser Lys Ser Glu Pro Gln Ser Gln Pro Lys Lys Glu Lys Arg
            20                  25                  30

Ala Tyr Arg Phe Arg Pro Gly Thr Val Ala Leu Arg Glu Ile Arg Lys
        35                  40                  45

Tyr Arg Lys Ser Thr Asn Met Leu Ile Pro Phe Ala Pro Phe Val Arg
    50                  55                  60

Leu Val Arg Asp Ile Ala Asp Asn Leu Thr Pro Leu Ser Asn Lys Lys
65                  70                  75                  80
```

```
Glu Ser Lys Pro Thr Pro Trp Thr Pro Leu Ala Leu Leu Ser Leu Gln
                85                  90                  95

Glu Ser Ala Glu Tyr His Leu Val Asp Leu Phe Gly Lys Ala Asn Leu
            100                 105                 110

Cys Ala Ile His Ser His Arg Val Thr Ile Met Leu Lys Asp Met Gln
        115                 120                 125

Leu Ala Arg Arg Ile Gly Thr Arg Ser Leu Trp
    130                 135
```

<210> SEQ ID NO 10
<211> LENGTH: 178
<212> TYPE: PRT
<213> ORGANISM: Arabidopsis thaliana
<220> FEATURE:
<223> OTHER INFORMATION: thale cress histone H3-like centromere protein (CENH3)

<400> SEQUENCE: 10

```
Met Ala Arg Thr Lys His Arg Val Thr Arg Ser Gln Pro Arg Asn Gln
1               5                   10                  15

Thr Asp Ala Ala Gly Ala Ser Ser Gln Ala Ala Gly Pro Thr Thr
            20                  25                  30

Thr Pro Thr Arg Arg Gly Gly Glu Gly Gly Asp Asn Thr Gln Gln Thr
        35                  40                  45

Asn Pro Thr Thr Ser Pro Ala Thr Gly Thr Arg Arg Gly Ala Lys Arg
50                  55                  60

Ser Arg Gln Ala Met Pro Arg Gly Ser Gln Lys Lys Ser Tyr Arg Tyr
65                  70                  75                  80

Arg Pro Gly Thr Val Ala Leu Lys Glu Ile Arg His Phe Gln Lys Gln
                85                  90                  95

Thr Asn Leu Leu Ile Pro Ala Ala Ser Phe Ile Arg Glu Val Arg Ser
            100                 105                 110

Ile Thr His Met Leu Ala Pro Pro Gln Ile Asn Arg Trp Thr Ala Glu
        115                 120                 125

Ala Leu Val Ala Leu Gln Glu Ala Ala Glu Asp Tyr Leu Val Gly Leu
    130                 135                 140

Phe Ser Asp Ser Met Leu Cys Ala Ile His Ala Arg Arg Val Thr Leu
145                 150                 155                 160

Met Arg Lys Asp Phe Glu Leu Ala Arg Arg Leu Gly Gly Lys Gly Arg
                165                 170                 175

Pro Trp
```

<210> SEQ ID NO 11
<211> LENGTH: 152
<212> TYPE: PRT
<213> ORGANISM: Populus trichocarpa
<220> FEATURE:
<223> OTHER INFORMATION: black cottonwood histone H3

<400> SEQUENCE: 11

```
Met Ala Arg Thr Lys His Pro Val Ala Arg Lys Arg Ala Arg Ser Pro
1               5                   10                  15

Lys Arg Ser Asp Ala Ser Pro Ser Thr Pro Arg Thr Pro Thr Ser Ser
            20                  25                  30

Arg Thr Arg Pro Gln Ala Asn Gly Gln Gln Gly Ser Ser Thr Gln Arg
        35                  40                  45

Gln Arg Lys Lys His Arg Phe Arg Ser Gly Thr Val Ala Leu Arg Glu
    50                  55                  60
```

Ile Arg Gln Tyr Gln Lys Thr Trp Arg Pro Leu Ile Pro Ala Ala Ser
65                  70                  75                  80

Phe Ile Arg Cys Val Arg Met Ile Thr Gln Glu Phe Ser Arg Glu Val
                85                  90                  95

Asn Arg Trp Thr Ala Glu Ala Leu Val Ala Ile Gln Glu Ala Ala Glu
            100                 105                 110

Asp Phe Leu Val His Leu Phe Glu Asp Gly Met Leu Cys Ala Ile His
        115                 120                 125

Ala Lys Arg Val Thr Leu Met Lys Lys Asp Phe Glu Leu Ala Arg Arg
130                 135                 140

Leu Gly Gly Lys Gly Arg Pro Trp
145                 150

<210> SEQ ID NO 12
<211> LENGTH: 166
<212> TYPE: PRT
<213> ORGANISM: Triticum aestivum
<220> FEATURE:
<223> OTHER INFORMATION: wheat CENH3

<400> SEQUENCE: 12

Met Ala Arg Thr Lys His Pro Ala Val Arg Lys Thr Lys Ala Leu Pro
1               5                   10                  15

Lys Lys Gln Leu Gly Thr Arg Pro Ser Ala Gly Thr Pro Arg Arg Gln
            20                  25                  30

Glu Thr Asp Gly Ala Gly Thr Ser Ala Thr Pro Arg Arg Ala Gly Arg
        35                  40                  45

Ala Ala Ala Pro Gly Ala Ala Glu Gly Ala Thr Gly Gln Pro Lys Gln
    50                  55                  60

Arg Lys Pro His Arg Phe Arg Pro Gly Thr Val Ala Leu Arg Glu Ile
65                  70                  75                  80

Arg Lys Tyr Gln Lys Ser Val Asp Phe Leu Ile Pro Phe Ala Pro Phe
                85                  90                  95

Val Arg Leu Ile Lys Glu Val Thr Asp Phe Phe Cys Pro Glu Ile Ser
            100                 105                 110

Arg Trp Thr Pro Gln Ala Leu Val Ala Ile Gln Glu Ala Ala Glu Tyr
        115                 120                 125

His Leu Val Asp Val Phe Glu Arg Ala Asn His Cys Ala Ile His Ala
    130                 135                 140

Lys Arg Val Thr Val Met Gln Lys Asp Ile Gln Leu Ala Arg Arg Ile
145                 150                 155                 160

Gly Gly Arg Arg Leu Trp
                165

<210> SEQ ID NO 13
<211> LENGTH: 170
<212> TYPE: PRT
<213> ORGANISM: Oryza sativa
<220> FEATURE:
<223> OTHER INFORMATION: rice centromeric histone 3 (CENH3)

<400> SEQUENCE: 13

Met Ala Arg Thr Lys His Pro Ala Val Arg Lys Ser Lys Ala Glu Pro
1               5                   10                  15

Lys Lys Lys Leu Gln Phe Glu Arg Ser Pro Arg Pro Ser Lys Ala Gln
            20                  25                  30

Arg Ala Gly Gly Gly Thr Gly Thr Ser Ala Thr Thr Arg Ser Ala Ala

```
                35                  40                  45

Gly Thr Ser Ala Ser Gly Thr Pro Arg Gln Gln Thr Lys Gln Arg Lys
        50                  55                  60

Pro His Arg Phe Arg Pro Gly Thr Val Ala Leu Arg Glu Ile Arg Lys
65                  70                  75                  80

Phe Gln Lys Thr Thr Glu Leu Leu Ile Pro Phe Ala Pro Phe Ser Arg
                85                  90                  95

Leu Val Arg Glu Ile Thr Asp Phe Tyr Ser Lys Asp Val Ser Arg Trp
            100                 105                 110

Thr Leu Glu Ala Leu Leu Ala Leu Gln Glu Ala Ala Glu Tyr His Leu
        115                 120                 125

Val Asp Ile Phe Glu Val Ser Asn Leu Cys Ala Ile His Ala Lys Arg
    130                 135                 140

Val Thr Ile Met Gln Lys Asp Met Gln Leu Ala Arg Arg Ile Gly Gly
145                 150                 155                 160

Arg Arg Pro Trp Asn Leu Asn Ser Leu Arg
                165                 170

<210> SEQ ID NO 14
<211> LENGTH: 167
<212> TYPE: PRT
<213> ORGANISM: Luzula nivea
<220> FEATURE:
<223> OTHER INFORMATION: snowy woodrush centromere specific histone H3
      variant (CENH3)

<400> SEQUENCE: 14

Met Ala Arg Thr Lys His Phe Pro Gln Cys Ser Arg His Pro Lys Lys
1               5                   10                  15

Gln Arg Thr Ala Ala Gly Glu Ala Gly Ser Ser Val Ile Ala Lys Gln
            20                  25                  30

Asn Ala Pro Ala Lys Thr Gly Asn Ala Ser Ser Ile Thr Asn Ser Thr
        35                  40                  45

Pro Ala Arg Ser Leu Lys Lys Asn Lys Ala Ser Lys Arg Gly Glu Lys
    50                  55                  60

Thr Gln Ala Lys Gln Arg Lys Met Tyr Arg Tyr Arg Pro Gly Thr Val
65                  70                  75                  80

Ala Leu Arg Glu Ile Arg Lys Leu Gln Lys Thr Thr Asp Leu Leu Val
                85                  90                  95

Pro Lys Ala Ser Phe Ala Arg Leu Val Lys Glu Ile Thr Phe Gln Ser
            100                 105                 110

Ser Lys Glu Val Asn Arg Trp Gln Ala Glu Ala Leu Ile Ala Leu Gln
        115                 120                 125

Glu Ala Ser Glu Cys Phe Leu Val Asn Leu Leu Glu Ser Ala Asn Met
    130                 135                 140

Leu Ala Ile His Ala Arg Arg Val Thr Ile Met Lys Lys Asp Ile Gln
145                 150                 155                 160

Leu Ala Arg Arg Ile Gly Ala
                165

<210> SEQ ID NO 15
<211> LENGTH: 176
<212> TYPE: PRT
<213> ORGANISM: Arabidopsis arenosa
<220> FEATURE:
<223> OTHER INFORMATION: sand rockcress CENH3

<400> SEQUENCE: 15
```

```
Met Ala Arg Thr Lys His Phe Ala Thr Arg Thr Gly Ser Gly Asn Arg
1               5                   10                  15

Thr Asp Ala Asn Ala Ser Ser Gln Ala Ala Gly Pro Thr Thr Thr
            20                  25                  30

Pro Thr Thr Arg Gly Thr Glu Gly Gly Asp Asn Thr Gln Gln Thr Asn
            35                  40                  45

Pro Thr Thr Ser Pro Ala Thr Gly Gly Arg Arg Pro Arg Arg Ala Arg
50                  55                  60

Gln Ala Met Pro Arg Gly Ser Gln Lys Lys Pro Tyr Arg Tyr Lys Pro
65                  70                  75                  80

Gly Thr Val Ala Leu Arg Glu Ile Arg His Phe Gln Lys Gln Thr Asn
                85                  90                  95

Leu Leu Ile Pro Ala Ala Ser Phe Ile Arg Gln Val Arg Ser Ile Thr
                100                 105                 110

His Ala Leu Ala Pro Pro Gln Ile Asn Arg Trp Thr Ala Glu Ala Leu
            115                 120                 125

Val Ala Leu Gln Glu Ala Ala Glu Asp Tyr Leu Ile Gly Leu Phe Ser
            130                 135                 140

Asp Ser Met Leu Cys Ala Ile His Ala Arg Arg Val Thr Leu Met Arg
145                 150                 155                 160

Lys Asp Phe Glu Leu Ala Arg Arg Leu Gly Gly Lys Gly Arg Pro Trp
                165                 170                 175

<210> SEQ ID NO 16
<211> LENGTH: 157
<212> TYPE: PRT
<213> ORGANISM: Zea mays
<220> FEATURE:
<223> OTHER INFORMATION: corn centromeric histone H3 (CENH3)

<400> SEQUENCE: 16

Met Ala Arg Thr Lys His Gln Ala Val Arg Lys Thr Ala Glu Lys Pro
1               5                   10                  15

Lys Lys Lys Leu Gln Phe Glu Arg Ser Gly Gly Ala Ser Thr Ser Ala
            20                  25                  30

Thr Pro Glu Arg Ala Ala Gly Thr Gly Gly Arg Ala Ala Ser Gly Gly
            35                  40                  45

Asp Ser Val Lys Lys Thr Lys Pro Arg His Arg Trp Arg Pro Gly Thr
50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Arg Glu Leu Thr Asn Phe
                85                  90                  95

Val Thr Asn Gly Lys Val Glu Arg Tyr Thr Ala Glu Ala Leu Leu Ala
                100                 105                 110

Leu Gln Glu Ala Ala Glu Phe His Leu Ile Glu Leu Phe Glu Met Ala
            115                 120                 125

Asn Leu Cys Ala Ile His Ala Lys Arg Val Thr Ile Met Gln Lys Asp
130                 135                 140

Ile Gln Leu Ala Arg Arg Ile Gly Gly Arg Arg Trp Ala
145                 150                 155

<210> SEQ ID NO 17
<211> LENGTH: 154
<212> TYPE: PRT
<213> ORGANISM: Sorghum bicolor
```

```
<220> FEATURE:
<223> OTHER INFORMATION: sorghum CENH3

<400> SEQUENCE: 17

Met Ala Arg Thr Lys His Gln Ala Val Arg Lys Leu Pro Gln Lys Pro
1               5                   10                  15

Lys Lys Lys Leu Gln Phe Glu Arg Ala Gly Ala Ser Thr Ser Ala
            20                  25                  30

Thr Pro Arg Arg Asn Ala Gly Thr Gly Gly Ala Ala Ala Arg Gly
        35                  40                  45

Glu Asp Leu Phe Lys Lys His Arg Trp Arg Ala Gly Thr Val Ala Leu
        50                  55                  60

Arg Glu Ile Arg Lys Tyr Gln Lys Ser Thr Glu Pro Leu Ile Pro Phe
65                  70                  75                  80

Ala Pro Phe Val Arg Val Val Lys Glu Leu Thr Ala Phe Ile Thr Asp
                85                  90                  95

Trp Arg Ile Gly Arg Tyr Thr Pro Glu Ala Leu Leu Ala Leu Gln Glu
                100                 105                 110

Ala Ala Glu Phe His Leu Ile Glu Leu Phe Glu Val Ala Asn Leu Cys
            115                 120                 125

Ala Ile His Ala Lys Arg Val Thr Val Met Gln Lys Asp Ile Gln Leu
        130                 135                 140

Ala Arg Arg Ile Gly Gly Arg Arg Trp Ser
145                 150

<210> SEQ ID NO 18
<211> LENGTH: 150
<212> TYPE: PRT
<213> ORGANISM: Cichorium intybus
<220> FEATURE:
<223> OTHER INFORMATION: chicory CENH3

<400> SEQUENCE: 18

Met Ala Arg Thr Lys Gln Pro Ala Lys Arg Ser Trp Gly Asn Arg Lys
1               5                   10                  15

Ser Ser Gln Ser Arg Ala Ser Thr Ser Thr Ser Thr Ser Thr Pro Arg
            20                  25                  30

Lys Ser Pro Arg Lys Asp Pro Gly Arg Thr Gly Glu Arg Arg Gln Gln
        35                  40                  45

Lys Pro His Arg Phe Lys Pro Gly Ala Gln Ala Leu Arg Glu Ile Arg
    50                  55                  60

Arg Leu Gln Lys Thr Val Asn Leu Leu Ile Pro Ala Ala Pro Phe Ile
65                  70                  75                  80

Arg Thr Val Lys Glu Ile Ser Asn Tyr Ile Ala Pro Glu Val Thr Arg
                85                  90                  95

Trp Gln Ala Glu Ala Ile Gln Ala Leu Gln Glu Ala Ala Glu Asp Tyr
                100                 105                 110

Leu Val Gln Leu Phe Glu Asp Ser Met Leu Cys Ser Ile His Ala Lys
            115                 120                 125

Arg Val Thr Leu Met Lys Lys Asp Trp Glu Leu Ala Arg Arg Leu Thr
        130                 135                 140

Lys Lys Gly Gln Pro Trp
145                 150

<210> SEQ ID NO 19
<211> LENGTH: 153
<212> TYPE: PRT
```

-continued

```
<213> ORGANISM: Cycas rumphii
<220> FEATURE:
<223> OTHER INFORMATION: queen sago CENH3

<400> SEQUENCE: 19

Met Ala Arg Lys Lys Ala Ser Thr Pro Arg Lys Lys Thr Gly Thr Ala
1               5                   10                  15

Ala Ser Thr Ser Ala Val Glu Ser Pro Pro Ser Gly Val Asn Gln Thr
                20                  25                  30

Ala Arg Ala Arg Arg Ser Val Gly Gly Val Ala Pro Gly Ala Pro Arg
            35                  40                  45

Thr Pro Gln Ala Ser Thr Asn Val Gly Thr Pro Arg Arg Pro His Arg
    50                  55                  60

Phe Arg Pro Gly Thr Val Ala Leu Arg Glu Ile Arg Arg Tyr Gln Lys
65                  70                  75                  80

Ser Phe Glu Leu Leu Ile Pro Ala Leu Pro Phe Ala Arg Asn Val Arg
                85                  90                  95

Glu Leu Thr Leu His His Ser Arg Glu Val His Arg Trp Thr Ala Glu
            100                 105                 110

Ala Leu Val Ala Leu Gln Glu Ala Ala Glu Asp Tyr Ile Val His Leu
        115                 120                 125

Phe Glu Asp Thr Asn Leu Cys Ala Ile His Lys Arg Val Thr Ile
    130                 135                 140

Met Pro Lys Asp Met His Leu Ala Arg
145                 150

<210> SEQ ID NO 20
<211> LENGTH: 154
<212> TYPE: PRT
<213> ORGANISM: Allium cepa
<220> FEATURE:
<223> OTHER INFORMATION: onion CENH3

<400> SEQUENCE: 20

Met Ala Arg Thr Lys Gln Met Ala His Lys Lys Leu Arg Arg Lys Leu
1               5                   10                  15

Asn Val Asp Glu Ala Gly Pro Ser Thr Pro Val Thr Arg Ser Thr Glu
                20                  25                  30

Val Asn Pro Lys Ser Ser Arg Pro Thr Pro Ile Thr Glu Asp Arg Gly
            35                  40                  45

Thr Gly Ala Arg Lys Lys His Arg Phe Arg Pro Gly Thr Val Ala Leu
    50                  55                  60

Arg Glu Ile Arg Lys Tyr Gln Lys Thr Ala Glu Leu Leu Ile Pro Ala
65                  70                  75                  80

Ala Pro Phe Ile Arg Leu Val Arg Glu Ile Thr Asn Leu Tyr Ser Lys
                85                  90                  95

Glu Val Thr Arg Trp Thr Pro Glu Ala Leu Leu Ala Ile Gln Glu Ala
            100                 105                 110

Ala Glu Phe Phe Ile Ile Asn Leu Leu Glu Glu Ala Asn Leu Cys Ala
        115                 120                 125

Ile His Ala Lys Arg Val Thr Leu Met Gln Lys Asp Ile Gln Leu Ala
    130                 135                 140

Arg Arg Ile Gly Gly Ala Arg His Phe Ser
145                 150

<210> SEQ ID NO 21
<211> LENGTH: 199
```

```
<212> TYPE: PRT
<213> ORGANISM: Malus domestica
<220> FEATURE:
<223> OTHER INFORMATION: apple CENH3

<400> SEQUENCE: 21
```

Met Ala Arg Ile Lys His Thr Ala His Lys Lys Ser Val Ala Arg Lys
1               5                   10                  15

Ser Ser Thr Pro Lys Glu Ala Ala Gly Thr Gly Gly Thr Ser Ala
            20                  25                  30

Ala Ser Pro Ala Lys Gln Pro Glu Pro Ser Ala Pro Trp Arg Arg Ser
        35                  40                  45

Glu Arg Ser Ser Gln Arg Thr Ser Glu Ser Gln Glu Gln Gln Glu Pro
    50                  55                  60

Glu Thr Asn Ala Gln Ala Thr Pro Gln Ser Lys Lys Gln Lys Gln Ser
65              70                  75                  80

Glu Arg Asn Pro Gln Thr Pro Gln Ser Lys Lys Gln Lys Pro Ser Glu
                85                  90                  95

Arg Asn Pro Pro Pro Thr Gln Lys Lys Lys Trp Arg Tyr Arg Pro Gly
                100                 105                 110

Thr Val Ala Leu Arg Glu Ile Arg Tyr Tyr Gln Lys Thr Trp Asn Leu
            115                 120                 125

Ile Ile Pro Ala Ala Pro Phe Ile Arg Thr Val Arg Glu Ile Ser Ile
130                 135                 140

Asn Met Ser Lys Asp Pro Val Arg Trp Thr Pro Glu Ala Leu Gln Ala
145                 150                 155                 160

Ile Gln Glu Ala Ala Glu Asp Phe Leu Val Arg Leu Phe Glu Asp Ser
                165                 170                 175

Met Leu Cys Ala Ile His Ala Arg Arg Val Thr Leu Met Lys Lys Asp
            180                 185                 190

Leu Glu Leu Ala Arg Arg Ile
            195

```
<210> SEQ ID NO 22
<211> LENGTH: 150
<212> TYPE: PRT
<213> ORGANISM: Lactuca sativa
<220> FEATURE:
<223> OTHER INFORMATION: lettuce CENH3

<400> SEQUENCE: 22
```

Met Ala Arg Thr Lys Gln Pro Ala Lys Arg Ser Trp Gly Lys Arg Gln
1               5                   10                  15

Ser Ala Gly Ala Ser Thr Ser Thr Ser Thr Thr Pro Arg Lys Ser
            20                  25                  30

Pro Arg Lys Asp Pro Gly Ser Ser Gly Thr Gly Gln Arg Gln Lys Gln
        35                  40                  45

Lys Pro His Arg Phe Lys Pro Gly Thr Gln Ala Leu Arg Glu Ile Arg
    50                  55                  60

Arg Leu Gln Lys Thr Val Asn Leu Leu Ile Pro Ala Ala Pro Phe Ile
65              70                  75                  80

Arg Thr Val Lys Glu Ile Ser Asn Tyr Ile Ala Pro Glu Val Thr Arg
                85                  90                  95

Trp Gln Ala Glu Ala Leu Gln Ala Leu Gln Glu Ala Ala Glu Asp Tyr
                100                 105                 110

Ile Val Gln Leu Phe Glu Asp Ser Met Leu Cys Ser Ile His Ala Lys
            115                 120                 125

Arg Val Thr Leu Met Lys Lys Asp Met Glu Leu Ala Arg Arg Leu Thr
            130                 135                 140

Lys Lys Gly Gln Pro Trp
145                 150

<210> SEQ ID NO 23
<211> LENGTH: 145
<212> TYPE: PRT
<213> ORGANISM: Carthamus tinctorius
<220> FEATURE:
<223> OTHER INFORMATION: safflower CENH3

<400> SEQUENCE: 23

Met Ala Arg Thr Lys Gln Pro Ala Lys Arg Ser Ser Gly Lys Arg Asp
1               5                   10                  15

Ala Arg Pro Ser Thr Ser Thr Pro Thr Pro Arg Pro Ser Ala Arg Lys
            20                  25                  30

Asn Pro Glu Ser Ser Gly Ala Gly Asp Gly Gln Arg Arg His Arg Tyr
        35                  40                  45

Arg Pro Gly Thr Gln Ala Leu Arg Glu Ile Arg Arg Leu Gln Lys Thr
    50                  55                  60

Val Asn Leu Leu Ile Pro Ala Ala Pro Phe Ile Arg Thr Val Lys Glu
65                  70                  75                  80

Ile Ser Asn Tyr Ile Ala Pro Glu Val Thr Arg Trp Gln Ala Glu Ala
                85                  90                  95

Leu Gln Ala Leu Gln Glu Ala Ala Glu Asp Tyr Leu Ile Gln Leu Phe
            100                 105                 110

Glu Asp Ser Met Leu Cys Ala Ile His Ala Lys Arg Val Thr Leu Met
        115                 120                 125

Lys Lys Asp Trp Glu Leu Ala Arg Arg Leu Gly Lys Lys Gly Gln Pro
    130                 135                 140

Trp
145

<210> SEQ ID NO 24
<211> LENGTH: 142
<212> TYPE: PRT
<213> ORGANISM: Helianthus exilis
<220> FEATURE:
<223> OTHER INFORMATION: serpentine sunflower CENH3

<400> SEQUENCE: 24

Met Ala Arg Thr Lys His Pro Ala Lys Arg Ser Ser Gly Ile Pro Val
1               5                   10                  15

Asp Gly Arg Ser Ser Thr Ser Thr Asn Thr Pro Arg Lys Ser Pro Arg
            20                  25                  30

Lys Asn Arg Gly Gly Glu Asn Arg Lys Pro His Arg Phe Lys Pro Gly
        35                  40                  45

Thr Gln Ala Leu Arg Glu Ile Arg Arg Leu Gln Lys Thr Val Glu Leu
    50                  55                  60

Ile Ile Pro Ala Ala Pro Phe Ile Arg Thr Val Lys Glu Ile Ser Asn
65                  70                  75                  80

Tyr Met Ala Pro Glu Ile Thr Arg Trp Gln Ala Glu Ala Leu Gln Ala
                85                  90                  95

Leu Gln Glu Ala Ala Glu Asp Tyr Leu Ile Gln Leu Phe Glu Asp Ser
            100                 105                 110

Met Leu Cys Ala Ile His Ala Lys Arg Val Thr Leu Met Lys Lys Asp

```
                    115                 120                 125
Trp Glu Leu Ala Arg Arg Ile Gly Lys Lys Gly Gln Pro Trp
    130                 135                 140

<210> SEQ ID NO 25
<211> LENGTH: 152
<212> TYPE: PRT
<213> ORGANISM: Gossypium hirsutum
<220> FEATURE:
<223> OTHER INFORMATION: upland cotton CENH3

<400> SEQUENCE: 25

Met Ser Arg Thr Lys His Thr Ala Ala Lys Lys Pro Arg Arg Lys Pro
1               5                   10                  15

Ser Ala Ala Ala Ala Ser Pro Ala Thr Ala Ser Pro His Thr Arg
            20                  25                  30

Ser Val Thr Ala Lys Lys Thr Gly Gly Pro Ala Thr Pro Thr Pro Gly
        35                  40                  45

Lys Ser Lys Arg Pro His Arg Phe Arg Ala Gly Thr Arg Ala Leu Gln
    50                  55                  60

Glu Ile Arg Lys Tyr Gln Lys Thr Ser Asn Leu Leu Val Pro Ala Ala
65                  70                  75                  80

Ser Phe Ile Arg Glu Val Arg Ala Ile Ser Tyr Arg Phe Ala Pro Asp
                85                  90                  95

Ile Asn Arg Trp Gln Ala Glu Ala Leu Val Ala Ile Gln Glu Ala Glu
            100                 105                 110

Asp Tyr Leu Ile Gln Leu Phe Gly Asp Ala Met Leu Cys Ala Ile His
        115                 120                 125

Ala Lys Arg Val Thr Leu Met Lys Lys Asp Ile Gln Leu Ala Arg Arg
    130                 135                 140

Leu Gly Gly Met Gly Gln Pro Trp
145                 150

<210> SEQ ID NO 26
<211> LENGTH: 155
<212> TYPE: PRT
<213> ORGANISM: Glycine max
<220> FEATURE:
<223> OTHER INFORMATION: soybean CENH3

<400> SEQUENCE: 26

Met Ala Arg Val Lys His Thr Pro Ala Ser Arg Lys Ser Ala Lys Lys
1               5                   10                  15

Gln Ala Pro Arg Ala Ser Thr Ser Thr Gln Pro Pro Gln Ser Gln
            20                  25                  30

Ser Pro Ala Thr Arg Glu Arg Arg Ala Gln Gln Val Glu Pro Gln
        35                  40                  45

Gln Glu Pro Glu Ala Gln Gly Arg Lys Lys Arg Arg Asn Arg Ser Gly
    50                  55                  60

Thr Val Ala Leu Arg Glu Ile Arg His Phe Gln Arg Ser Cys Glu Leu
65                  70                  75                  80

Leu Ile Pro Ala Ala Pro Phe Ile Arg Cys Val Lys Gln Ile Thr Asn
                85                  90                  95

Gln Phe Ser Thr Glu Val Ser Arg Trp Thr Pro Glu Ala Val Val Ala
            100                 105                 110

Leu Gln Glu Ala Ala Glu Glu Tyr Leu Val His Leu Phe Glu Asp Gly
        115                 120                 125
```

```
Met Leu Cys Ala Ile His Ala Arg Arg Ile Thr Leu Met Lys Lys Asp
            130                 135                 140

Ile Glu Leu Ala Arg Arg Leu Gly Gly Ile Gly
145                 150                 155

<210> SEQ ID NO 27
<211> LENGTH: 153
<212> TYPE: PRT
<213> ORGANISM: Cucumis melo
<220> FEATURE:
<223> OTHER INFORMATION: cantaloupe CENH3

<400> SEQUENCE: 27

Met Ala Arg Ala Arg His Pro Val Gln Arg Lys Ser Asn Arg Thr Ser
1               5                   10                  15

Ser Gly Ser Gly Ala Ala Leu Ser Pro Pro Ala Val Pro Ser Thr Pro
            20                  25                  30

Leu Asn Gly Arg Thr Gln Asn Val Arg Lys Ala Gln Ser Pro Pro Ser
        35                  40                  45

Arg Thr Lys Lys Lys Ile Arg Phe Arg Pro Gly Thr Val Ala Leu Arg
    50                  55                  60

Glu Ile Arg Asn Leu Gln Lys Ser Trp Asn Leu Leu Ile Pro Ala Ser
65                  70                  75                  80

Cys Phe Ile Arg Ala Val Lys Glu Val Ser Asn Gln Leu Ala Pro Gln
                85                  90                  95

Ile Thr Arg Trp Gln Ala Glu Ala Leu Val Ala Leu Gln Glu Ala Ala
            100                 105                 110

Glu Asp Phe Leu Val His Leu Phe Glu Asp Thr Met Leu Cys Ala Ile
        115                 120                 125

His Ala Lys Arg Val Thr Ile Met Lys Lys Asp Phe Glu Leu Ala Arg
    130                 135                 140

Arg Leu Gly Gly Lys Gly Arg Pro Trp
145                 150

<210> SEQ ID NO 28
<211> LENGTH: 147
<212> TYPE: PRT
<213> ORGANISM: Solanum chacoense
<220> FEATURE:
<223> OTHER INFORMATION: Chaco potato CENH3

<400> SEQUENCE: 28

Met Ala Arg Thr Lys His Leu Ala Lys Arg Ser Arg Thr Lys Pro Ser
1               5                   10                  15

Val Ala Ala Gly Pro Ser Ala Thr Pro Ser Thr Pro Thr Arg Lys Ser
            20                  25                  30

Pro Arg Ser Ala Pro Ala Thr Ser Val Pro Lys Pro Gln Lys Lys
        35                  40                  45

Arg Tyr Arg Pro Gly Ser Val Ala Leu Arg Glu Ile Arg His Phe Gln
    50                  55                  60

Lys Thr Trp Asn Leu Val Ile Pro Ala Ala Pro Phe Ile Arg Leu Val
65                  70                  75                  80

Arg Glu Ile Ser His Phe Phe Ala Pro Gly Val Thr Trp Gln Ala
                85                  90                  95

Glu Ala Leu Ile Ala Ile Gln Glu Ala Ala Glu Asp Phe Leu Val His
            100                 105                 110

Leu Phe Glu Asp Ala Met Leu Cys Ala Ile His Ala Lys Arg Val Thr
        115                 120                 125
```

```
Leu Met Lys Lys Asp Phe Glu Leu Ala Arg Arg Leu Gly Gly Lys Gly
        130                 135                 140

Gln Pro Trp
145

<210> SEQ ID NO 29
<211> LENGTH: 144
<212> TYPE: PRT
<213> ORGANISM: Solanum lycopersicum
<220> FEATURE:
<223> OTHER INFORMATION: tomato CENH3

<400> SEQUENCE: 29

Met Ala Arg Thr Lys His Leu Ala Lys Arg Ser Arg Thr Thr Ser Ala
1               5                   10                  15

Ala Pro Ser Ala Thr Pro Ser Thr Pro Ser Arg Lys Ser Pro Arg Ser
            20                  25                  30

Ala Pro Ala Thr Ser Val Gln Lys Pro Lys Gln Lys Lys Arg Tyr Arg
        35                  40                  45

Pro Gly Thr Val Ala Leu Arg Glu Ile Arg His Phe Gln Lys Thr Trp
    50                  55                  60

Asp Leu Leu Ile Pro Ala Ala Pro Phe Ile Arg Leu Val Arg Glu Ile
65                  70                  75                  80

Ser His Phe Tyr Ala Pro Gly Val Thr Arg Trp Gln Ala Glu Ala Leu
                85                  90                  95

Ile Ala Ile Gln Glu Ala Ala Glu Asp Phe Leu Val His Leu Phe Glu
            100                 105                 110

Asp Ala Met Leu Cys Ala Ile His Ala Lys Arg Val Thr Leu Met Lys
        115                 120                 125

Lys Asp Phe Glu Leu Ala Arg Arg Leu Gly Gly Lys Gly Gln Pro Trp
    130                 135                 140

<210> SEQ ID NO 30
<211> LENGTH: 156
<212> TYPE: PRT
<213> ORGANISM: Nicotiana tabacum
<220> FEATURE:
<223> OTHER INFORMATION: allotetraploid tobacco centromere specific
      histone H3 variant (CENH3-1)

<400> SEQUENCE: 30

Met Ala Arg Thr Lys His Leu Ala Leu Arg Lys Gln Ser Arg Pro Pro
1               5                   10                  15

Ser Arg Pro Thr Ala Thr Arg Ser Ala Ala Ala Ala Ser Ser Ala
            20                  25                  30

Pro Gln Ser Thr Pro Thr Arg Thr Ser Gln Arg Thr Ala Pro Ser Thr
        35                  40                  45

Pro Gly Arg Thr Gln Lys Lys Lys Thr Arg Tyr Arg Pro Gly Thr Val
    50                  55                  60

Ala Leu Arg Glu Ile Arg Arg Phe Gln Lys Thr Trp Asp Leu Leu Ile
65                  70                  75                  80

Pro Ala Ala Pro Phe Ile Arg Leu Val Lys Glu Ile Ser His Phe Phe
                85                  90                  95

Ala Pro Glu Val Thr Arg Trp Gln Ala Glu Ala Leu Ile Ala Leu Gln
            100                 105                 110

Glu Ala Ala Glu Asp Phe Leu Val His Leu Phe Asp Asp Ser Met Leu
        115                 120                 125
```

```
Cys Ala Ile His Ala Lys Arg Val Thr Leu Met Lys Asp Phe Glu
    130                 135                 140

Leu Ala Arg Arg Leu Gly Gly Lys Ala Arg Pro Trp
145                 150                 155

<210> SEQ ID NO 31
<211> LENGTH: 157
<212> TYPE: PRT
<213> ORGANISM: Nicotiana tabacum
<220> FEATURE:
<223> OTHER INFORMATION: allotetraploid tobacco centromere specific
      histone H3 variant (CENH3-2)

<400> SEQUENCE: 31

Met Ala Arg Thr Lys His Leu Ala Leu Arg Lys Gln Ser Arg Pro Pro
1               5                   10                  15

Ser Arg Pro Thr Ala Thr Arg Ser Ala Ala Ala Ala Ser Ser Ser
            20                  25                  30

Ala Pro Gln Ser Thr Pro Thr Arg Thr Ser Gln Arg Thr Ala Pro Ser
            35                  40                  45

Thr Pro Gly Arg Thr Gln Lys Lys Thr Arg Tyr Arg Pro Gly Thr
        50                  55                  60

Val Ala Leu Arg Glu Ile Arg Arg Phe Gln Lys Thr Trp Asn Leu Leu
65                  70                  75                  80

Ile Pro Ala Ala Pro Phe Ile Arg Leu Val Lys Glu Ile Ser Tyr Phe
                85                  90                  95

Phe Ala Pro Glu Val Thr Arg Trp Gln Ala Glu Ala Leu Ile Ala Leu
                100                 105                 110

Gln Glu Ala Ala Glu Asp Phe Leu Val His Leu Phe Asp Asp Ser Met
            115                 120                 125

Leu Cys Ala Ile His Ala Lys Arg Val Thr Leu Met Lys Lys Asp Phe
        130                 135                 140

Glu Leu Ala Arg Arg Leu Gly Gly Lys Ala Arg Pro Trp
145                 150                 155

<210> SEQ ID NO 32
<211> LENGTH: 156
<212> TYPE: PRT
<213> ORGANISM: Nicotiana tomentosiformis
<220> FEATURE:
<223> OTHER INFORMATION: diploid tobacco centromere specific histone H3
      variant (CENH3)

<400> SEQUENCE: 32

Met Ala Arg Thr Lys His Leu Ala Leu Arg Lys Gln Ser Arg Pro Pro
1               5                   10                  15

Ser Arg Pro Thr Ala Thr Arg Ser Ala Ala Ala Ala Ser Ser Ala
            20                  25                  30

Pro Gln Ser Thr Pro Thr Arg Thr Ser Gln Arg Thr Ala Pro Ser Thr
            35                  40                  45

Pro Gly Arg Thr Gln Lys Lys Thr Arg Tyr Arg Pro Gly Thr Val
        50                  55                  60

Ala Leu Arg Glu Ile Arg Arg Phe Gln Lys Thr Trp Asp Leu Leu Ile
65                  70                  75                  80

Pro Ala Ala Pro Phe Ile Arg Leu Val Lys Glu Ile Ser His Phe Phe
                85                  90                  95

Ala Pro Glu Val Thr Arg Trp Gln Ala Glu Ala Leu Ile Ala Leu Gln
                100                 105                 110
```

-continued

```
Glu Ala Ala Glu Asp Phe Leu Val His Leu Phe Asp Ser Met Leu
            115                 120                 125

Cys Ala Ile His Ala Lys Arg Val Thr Leu Met Lys Lys Asp Phe Glu
130                 135                 140

Leu Ala Arg Arg Leu Gly Gly Lys Ala Arg Pro Trp
145                 150                 155

<210> SEQ ID NO 33
<211> LENGTH: 158
<212> TYPE: PRT
<213> ORGANISM: Vitis vinifera
<220> FEATURE:
<223> OTHER INFORMATION: European wine grape CENH3

<400> SEQUENCE: 33

Met Thr Arg Thr Lys His Leu Ala Arg Lys Ser Arg Asn Arg Arg
1               5                   10                  15

Gln Phe Ala Ala Thr Pro Ala Ser Pro Ala Ser Ala Gly Pro Ser Ser
                20                  25                  30

Ala Pro Pro Arg Arg Pro Thr Arg Thr Ala Thr Asp Ala Ser Pro Ser
            35                  40                  45

Thr Ala Gly Ser Gln Gly Gln Arg Lys Pro Phe Arg Tyr Arg Pro Gly
        50                  55                  60

Thr Val Ala Leu Arg Glu Ile Arg Arg Phe Gln Lys Thr Thr His Leu
65                  70                  75                  80

Leu Ile Pro Ala Ala Pro Phe Ile Arg Thr Val Arg Glu Ile Ser Tyr
                85                  90                  95

Phe Phe Ala Pro Glu Ile Ser Arg Trp Thr Ala Glu Ala Leu Val Ala
                100                 105                 110

Leu Gln Glu Ala Ala Glu Asp Tyr Leu Val His Leu Phe Glu Asp Ala
            115                 120                 125

Met Leu Cys Ala Ile His Ala Lys Arg Val Thr Leu Met Lys Lys Asp
130                 135                 140

Trp Glu Leu Ala Arg Arg Ile Gly Gly Lys Gly Gln Pro Trp
145                 150                 155

<210> SEQ ID NO 34
<211> LENGTH: 157
<212> TYPE: PRT
<213> ORGANISM: Nicotiana sylvestris
<220> FEATURE:
<223> OTHER INFORMATION: woodland tobacco centromere specific histone H3
      variant (CENH3)

<400> SEQUENCE: 34

Met Ala Arg Thr Lys His Leu Ala Leu Arg Lys Gln Ser Arg Pro Pro
1               5                   10                  15

Ser Arg Pro Thr Ala Thr Arg Ser Ala Ala Ala Ala Ser Ser Ser
                20                  25                  30

Ala Pro Gln Ser Thr Pro Thr Ser Gln Arg Thr Ala Pro Ser
            35                  40                  45

Thr Pro Gly Arg Thr Gln Lys Lys Thr Arg Tyr Arg Pro Gly Thr
        50                  55                  60

Val Ala Leu Arg Glu Ile Arg Arg Phe Gln Lys Thr Trp Asn Leu Leu
65                  70                  75                  80

Ile Pro Ala Ala Pro Phe Ile Arg Leu Val Lys Glu Ile Ser Tyr Phe
                85                  90                  95

Phe Ala Pro Glu Val Thr Arg Trp Gln Ala Glu Ala Leu Ile Ala Leu
```

```
                    100                 105                 110
Gln Glu Ala Ala Glu Asp Phe Leu Val His Leu Phe Asp Asp Ser Met
            115                 120                 125

Leu Cys Ala Ile His Ala Lys Arg Val Thr Leu Met Lys Lys Asp Phe
        130                 135                 140

Glu Leu Ala Arg Arg Leu Gly Gly Lys Ala Arg Pro Trp
145                 150                 155

<210> SEQ ID NO 35
<211> LENGTH: 177
<212> TYPE: PRT
<213> ORGANISM: Crucihimalaya himalaica
<220> FEATURE:
<223> OTHER INFORMATION: Himalayan rockcress centromeric histone (CENH3)

<400> SEQUENCE: 35

Met Ala Arg Thr Lys His Phe Ala Thr Arg Ser Arg Pro Arg Asn Gln
1               5                   10                  15

Thr Asp Ala Thr Ala Ser Ala Ser Gln Ala Thr Gly Pro Ser Thr Asn
            20                  25                  30

Pro Thr Thr Arg Gly Ser Glu Gly Glu Asp Ala Ala Arg Gly Thr Asn
        35                  40                  45

Pro Thr Thr Ser Pro Ala Thr Gly Arg Lys Lys Gly Val Lys Arg Ala
    50                  55                  60

Arg His Ala Met Pro Gln Gly Ser Gln Lys Lys Pro Tyr Arg Tyr Lys
65                  70                  75                  80

Ala Gly Thr Val Ala Leu Arg Glu Ile Arg His Phe Gln Lys Asn Thr
                85                  90                  95

Asn Leu Leu Ile Pro Ala Ala Ser Phe Ile Arg Gln Val Lys Ser Ile
            100                 105                 110

Thr Tyr Ala Val Ala Pro Pro Gln Ile Thr Arg Trp Thr Ala Glu Ala
        115                 120                 125

Leu Val Ala Leu Gln Glu Ala Ala Glu Asp Tyr Leu Val Gly Leu Phe
    130                 135                 140

Ser Asp Ser Met Leu Cys Ala Ile His Ala Arg Arg Val Thr Leu Met
145                 150                 155                 160

Arg Lys Asp Phe Glu Leu Ala Arg Arg Leu Gly Gly Lys Gly Arg Pro
                165                 170                 175

Trp

<210> SEQ ID NO 36
<211> LENGTH: 176
<212> TYPE: PRT
<213> ORGANISM: Arabidopsis lyrata
<220> FEATURE:
<223> OTHER INFORMATION: lyre-leaved rockcress centromeric histone
      (CENH3)

<400> SEQUENCE: 36

Met Ala Arg Thr Lys His Phe Ala Thr Lys Ser Arg Ser Gly Asn Arg
1               5                   10                  15

Thr Asp Ala Asn Ala Ser Ser Ser Gln Ala Ala Gly Pro Thr Thr Thr
            20                  25                  30

Pro Thr Thr Arg Gly Thr Glu Gly Gly Asp Asn Thr Gln Gln Thr Asn
        35                  40                  45

Pro Thr Thr Ser Pro Ala Thr Gly Gly Arg Arg Pro Arg Arg Ala Arg
    50                  55                  60
```

```
Gln Ala Met Pro Arg Val Ser Gln Asn Lys Pro Tyr Arg Tyr Lys Pro
 65                  70                  75                  80

Gly Thr Val Ala Leu Arg Glu Ile Arg His Phe Gln Lys Gln Thr Asn
                 85                  90                  95

Leu Leu Ile Pro Ala Ala Ser Phe Ile Arg Gln Val Arg Ser Ile Thr
            100                 105                 110

His Ala Leu Ala Pro Pro Gln Ile Asn Arg Trp Thr Ala Glu Ala Leu
        115                 120                 125

Val Ala Leu Gln Glu Ala Glu Asp Tyr Leu Val Gly Leu Phe Ser
    130                 135                 140

Asp Ser Met Leu Cys Ala Ile His Ala Arg Arg Val Thr Leu Met Arg
145                 150                 155                 160

Lys Asp Phe Glu Leu Ala Arg Arg Leu Gly Gly Lys Gly Arg Pro Trp
                165                 170                 175
```

```
<210> SEQ ID NO 37
<211> LENGTH: 170
<212> TYPE: PRT
<213> ORGANISM: Capsella bursapastoris
<220> FEATURE:
<223> OTHER INFORMATION: shepherd's purse centromeric histone (CENH3)

<400> SEQUENCE: 37
```

```
Met Ala Arg Thr Lys His Phe Ala Thr Arg Ser Gly Pro Arg Thr Pro
 1               5                  10                  15

Ala Val Ala Ser Ser Ser Gln Ala Ala Val Pro Ser Ser Ser Pro Ala
                 20                  25                  30

Thr Arg Gly Arg Val Gly Val Asp Ala Ala Ala Gln Gln Pro Thr Pro
             35                  40                  45

Ala Thr Ser Pro Ala Thr Ala Lys Lys Lys Gly Ala Lys Arg Ala Arg
         50                  55                  60

Phe Gly Arg Pro Gln Gly Ser Gln Lys Lys Lys Pro Tyr Arg Tyr Arg
 65                  70                  75                  80

Pro Gly Thr Val Ala Leu Arg Glu Ile Arg His Tyr Gln Lys Gly Thr
                 85                  90                  95

Ser Leu Leu Ile Pro Ala Ala Ala Phe Ile Arg Gln Val Arg Ser Ile
            100                 105                 110

Thr Asn Ala Val Ala Pro Arg Glu Val Asn Arg Trp Thr Ala Glu Ala
        115                 120                 125

Leu Val Ala Leu Gln Glu Ala Ala Glu Asp Phe Leu Val Gly Leu Phe
    130                 135                 140

Ser Asp Ser Met Leu Cys Ala Ile His Ala Arg Arg Val Thr Leu Met
145                 150                 155                 160

Arg Lys Asp Phe Asp Leu Ala Arg Arg Leu
                165                 170
```

```
<210> SEQ ID NO 38
<211> LENGTH: 178
<212> TYPE: PRT
<213> ORGANISM: Raphanus sativus
<220> FEATURE:
<223> OTHER INFORMATION: radish centromeric histone H3-like protein
      (CENH3)

<400> SEQUENCE: 38
```

```
Met Ala Arg Thr Lys His Phe Ala Ser Arg Ala Arg Asp Arg Asn Gln
 1               5                  10                  15

Pro Asn Ala Ala Ala Ala Ala Ala Gly Pro Ser Ala Thr Pro Thr Arg
```

```
                     20                  25                  30
Arg Gly Ser Ser Gln Gly Glu Glu Ala Gln Gln Thr Thr Pro Thr Thr
                 35                  40                  45

Thr Ser Pro Ala Thr Thr Ala Ser Gly Arg Lys Lys Gly Thr Lys Arg
 50                  55                  60

Thr Thr Gln Ala Met Pro Lys Ser Ser Lys Lys Lys Thr Phe Arg Tyr
 65                  70                  75                  80

Lys Pro Gly Thr Val Ala Leu Arg Glu Ile Arg His Phe Gln Lys Ser
                 85                  90                  95

Thr Lys Leu Leu Ile Pro Ser Ala Pro Phe Ile Arg Glu Val Arg Ser
                100                 105                 110

Ile Thr His Asn Leu Ala Ala Ala Tyr Val Thr Arg Trp Thr Ala Glu
                115                 120                 125

Ala Leu Ile Ala Leu Gln Glu Ala Ala Glu Asp Phe Leu Val Gly Leu
                130                 135                 140

Phe Ser Asp Ala Met Leu Cys Ala Ile His Ala Lys Arg Val Thr Leu
145                 150                 155                 160

Met Arg Lys Asp Phe Glu Leu Ala Arg Arg Leu Gly Gly Lys Gly Arg
                165                 170                 175

Pro Phe

<210> SEQ ID NO 39
<211> LENGTH: 164
<212> TYPE: PRT
<213> ORGANISM: Eruca sativa
<220> FEATURE:
<223> OTHER INFORMATION: arugula centromeric histone H3-like protein
      (CENH3)

<400> SEQUENCE: 39

Met Ala Arg Thr Lys His Phe Ala Ser Arg Ala Arg Asp Arg Asn Arg
 1               5                  10                  15

Asn Asn Ala Thr Ala Ser Ser Ser Ala Ala Ala Ala Ala Ala Gly Pro
                 20                  25                  30

Ser Ala Thr Pro Thr Arg Arg Gly Ser Arg Gln Gly Gly Gly Gly Gly
                 35                  40                  45

Gly Gly Val Glu Ala Gln Gln Gly Ser Asn Lys Lys Lys Lys Ser Phe
 50                  55                  60

Arg Tyr Lys Pro Gly Thr Val Ala Leu Arg Glu Ile Arg His Phe Gln
 65                  70                  75                  80

Lys Thr Thr Lys Leu Leu Ile Pro Ala Ala Thr Phe Ile Arg Leu Val
                 85                  90                  95

Arg Ser Ile Thr Leu Asp Arg Ala Lys Pro Gln Val Thr Arg Trp Thr
                100                 105                 110

Ala Glu Ala Leu Val Ala Leu Gln Glu Ala Ala Glu Asp Tyr Leu Val
                115                 120                 125

Gly Leu Phe Ser Asp Ser Met Leu Cys Ala Ile His Ala Lys Arg Val
                130                 135                 140

Thr Leu Met Arg Lys Asp Phe Glu Leu Ala Arg Arg Leu Gly Gly Lys
145                 150                 155                 160

Gly Arg Pro Trp

<210> SEQ ID NO 40
<211> LENGTH: 173
<212> TYPE: PRT
<213> ORGANISM: Olimarabidopsis pumila
```

<220> FEATURE:
<223> OTHER INFORMATION: dwarf rocket centromeric histone H3-like
    protein 1 (CENH3-1)

<400> SEQUENCE: 40

```
Met Ala Arg Thr Lys His Asn Ala Ile Arg Ser Arg Asp Arg Thr Gly
1               5                   10                  15

Ala Thr Ala Ser Ser Ser Gln Ala Ala Gly Pro Ser Thr Asn Pro Thr
            20                  25                  30

Ala Gly Gly Ser Glu Asp Ala Ala Gln Gln Thr Thr Pro Thr Thr Ser
        35                  40                  45

Pro Ala Thr Gly Ser Lys Lys Arg Ala Lys Arg Ala Arg Gln Ala Met
50                  55                  60

Pro Arg Gly Ser Gln Lys Lys Pro Tyr Arg Tyr Lys Pro Gly Thr Val
65                  70                  75                  80

Ala Leu Arg Glu Ile Arg His Phe Gln Lys Thr Thr Ser Leu Leu Leu
                85                  90                  95

Pro Ala Ala Pro Phe Ile Arg Gln Val Arg Ser Ile Ser Ser Ala Leu
            100                 105                 110

Ala Pro Arg Glu Ile Thr Arg Trp Thr Ala Glu Ala Leu Val Ala Leu
        115                 120                 125

Gln Glu Ala Ala Glu Asp Tyr Leu Val Gly Leu Phe Ser Asp Ser Met
130                 135                 140

Leu Cys Ala Ile His Ala Lys Arg Val Thr Leu Met Arg Lys Asp Phe
145                 150                 155                 160

Glu Leu Ala Arg Arg Leu Gly Gly Lys Gly Arg Pro Trp
                165                 170
```

<210> SEQ ID NO 41
<211> LENGTH: 174
<212> TYPE: PRT
<213> ORGANISM: Olimarabidopsis pumila
<220> FEATURE:
<223> OTHER INFORMATION: dwarf rocket centromeric histone H3-like
    protein 2 (CENH3-2)

<400> SEQUENCE: 41

```
Met Thr Arg Thr Lys His Thr Val Ile Lys Ser Ser Arg Pro Leu Asp
1               5                   10                  15

Arg Thr Asp Ala Ser Ser Ser Gln Ala Ala Gly Pro Ser Thr Asn Pro
            20                  25                  30

Thr Ala Gly Ser Ser Gly Asp Ala Ala Gln Gln Thr Thr Pro Thr Thr
        35                  40                  45

Ser Pro Ala Thr Gly Ser Thr Lys Arg Ala Lys Arg Ala Arg Gln Ala
50                  55                  60

Met Pro Arg Gly Ser Gln Lys Lys Pro Tyr Arg Tyr Lys Pro Gly Thr
65                  70                  75                  80

Val Ala Leu Arg Glu Ile Arg His Phe Gln Lys Thr Thr Ser Phe Leu
                85                  90                  95

Ile Pro Ala Ala Pro Phe Ile Arg Gln Val Arg Ser Ile Ser Ser Ala
            100                 105                 110

Leu Ala Pro Thr Gln Ile Thr Arg Trp Thr Ala Glu Ala Leu Val Ala
        115                 120                 125

Leu Gln Glu Ala Ala Glu Asp Tyr Leu Val Gly Leu Phe Ser Asp Ser
130                 135                 140

Met Leu Cys Ala Ile His Ala Lys Arg Val Thr Leu Met Arg Lys Asp
145                 150                 155                 160
```

Phe Glu Leu Ala Arg Arg Leu Gly Gly Lys Gly Arg Pro Trp
                165                 170

<210> SEQ ID NO 42
<211> LENGTH: 174
<212> TYPE: PRT
<213> ORGANISM: Turritis glabra
<220> FEATURE:
<223> OTHER INFORMATION: tower mustard histone H3 like protein (CENH3)

<400> SEQUENCE: 42

Met Ala Arg Thr Lys His Phe Ala Thr Arg Ser Arg Pro Arg Asn Gln
1               5                   10                  15

Thr Asp Ser Ser Ser Gln Ala Ala Gly Pro Ser Thr Asn Pro Thr Thr
                20                  25                  30

Gly Gly Ser Glu Gly Gly Asp Ala Ala Gln Gln Thr Thr Pro Thr Thr
            35                  40                  45

Ser Pro Ala Thr Gly Arg Lys Lys Arg Ala Lys Arg Ala Lys Gln Ala
    50                  55                  60

Met Pro Gln Gly Ser Gln Lys Lys Pro Tyr Arg Tyr Lys Pro Gly Thr
65                  70                  75                  80

Ile Ala Leu Arg Glu Ile Arg Tyr Phe Gln Lys Asn Thr Asn Leu Leu
                85                  90                  95

Ile Pro Ala Ala Ser Phe Ile Arg Glu Val Arg Ser Ile Thr His Ala
            100                 105                 110

Leu Ala Pro Pro Gln Ile Ser Arg Trp Thr Ala Glu Ala Leu Val Ala
        115                 120                 125

Leu Gln Glu Ala Ala Glu Asp Tyr Leu Val Gly Leu Phe Ser Asp Ser
    130                 135                 140

Met Leu Cys Ala Ile His Ala Arg Arg Val Thr Leu Met Arg Lys Asp
145                 150                 155                 160

Phe Glu Leu Ala Arg Arg Ile Gly Gly Lys Gly Arg Pro Trp
                165                 170

<210> SEQ ID NO 43
<211> LENGTH: 176
<212> TYPE: PRT
<213> ORGANISM: Arabidopsis halleri
<220> FEATURE:
<223> OTHER INFORMATION: histone H3 like protein 1 (CENH3-1)

<400> SEQUENCE: 43

Met Ala Arg Thr Lys His Phe Ala Ile Lys Ser Arg Ser Gly Asn Arg
1               5                   10                  15

Thr Asp Ala Asn Ala Ser Ser Ser Gln Ala Ala Gly Pro Thr Thr Thr
                20                  25                  30

Pro Thr Thr Arg Gly Thr Glu Gly Gly Asp Asn Thr Gln Gln Thr Asn
            35                  40                  45

Pro Thr Thr Ser Pro Ala Thr Gly Gly Arg Arg Pro Arg Arg Ala Arg
        50                  55                  60

Gln Ala Met Pro Arg Gly Ser Gln Lys Lys Pro Tyr Arg Tyr Lys Pro
65                  70                  75                  80

Gly Thr Val Ala Leu Arg Glu Ile Arg His Phe Gln Lys Gln Thr Asn
                85                  90                  95

Leu Leu Ile Pro Ala Ala Ser Phe Ile Arg Gln Val Arg Ser Ile Thr
            100                 105                 110

His Ala Leu Ala Pro Pro Gln Ile Asn Arg Trp Thr Ala Glu Ala Leu

```
                115                 120                 125
Val Ala Leu Gln Glu Ala Ala Glu Asp Tyr Leu Val Gly Leu Phe Ser
        130                 135                 140

Asp Ser Met Leu Cys Ala Ile His Ala Arg Arg Val Thr Leu Met Arg
145                 150                 155                 160

Lys Asp Phe Glu Leu Thr Arg Arg Leu Gly Gly Lys Gly Arg Pro Trp
                165                 170                 175

<210> SEQ ID NO 44
<211> LENGTH: 176
<212> TYPE: PRT
<213> ORGANISM: Arabidopsis halleri
<220> FEATURE:
<223> OTHER INFORMATION: histone H3 like protein 2 (CENH3-2)

<400> SEQUENCE: 44

Met Ala Arg Thr Lys His Phe Val Thr Arg Lys Gly Ser Gly Asn Arg
1               5                   10                  15

Thr Asp Phe Asp Ala Asn Ala Ser Ser Ser Gln Ala Ala Gly Pro Thr
            20                  25                  30

Lys Thr Pro Thr Thr Arg Gly Thr Glu Gly Gly Asp Asn Thr Gln Gln
        35                  40                  45

Thr Thr Ser Pro Ala Thr Gly Gly Arg Arg Gly Pro Arg Arg Ala Arg
    50                  55                  60

Gln Ala Met Pro Arg Gly Ser Gln Lys Lys Pro Tyr Arg Tyr Lys Pro
65                  70                  75                  80

Gly Thr Val Ala Leu Arg Glu Ile Arg His Phe Gln Lys Gln Thr Asn
                85                  90                  95

Leu Leu Ile Pro Ala Ala Ser Phe Ile Arg Gln Val Arg Ser Ile Thr
            100                 105                 110

His Ala Leu Ala Pro Pro Gln Ile Asn Arg Trp Thr Ala Glu Ala Leu
        115                 120                 125

Val Ala Leu Gln Glu Ala Ala Glu Asp Tyr Leu Val Gly Leu Phe Ser
    130                 135                 140

Asp Ser Met Leu Cys Ala Ile His Ala Arg Arg Val Thr Leu Met Arg
145                 150                 155                 160

Lys Asp Phe Glu Leu Ala Arg Arg Leu Gly Gly Lys Gly Arg Pro Trp
                165                 170                 175

<210> SEQ ID NO 45
<211> LENGTH: 175
<212> TYPE: PRT
<213> ORGANISM: Arabidopsis lyrata
<220> FEATURE:
<223> OTHER INFORMATION: lyre-leaved rockcress histone H3 (HTR12A)

<400> SEQUENCE: 45

Met Ala Arg Thr Lys His Phe Ala Thr Arg Thr Gly Ser Gly Asn Arg
1               5                   10                  15

Thr Asp Ala Asn Ala Ser Ser Ser Gln Ala Ala Gly Pro Thr Lys
            20                  25                  30

Thr Pro Thr Thr Arg Gly Thr Glu Gly Gly Asp Asn Thr Gln Gln Thr
        35                  40                  45

Thr Ser Pro Ala Thr Gly Gly Arg Gly Pro Arg Arg Ala Arg Gln
    50                  55                  60

Ala Met Pro Arg Gly Ser Gln Lys Lys Pro Tyr Arg Tyr Lys Pro Gly
65                  70                  75                  80
```

```
Thr Val Ala Leu Arg Glu Ile Arg His Phe Gln Lys Gln Thr Asn Leu
                85                  90                  95

Leu Ile Pro Ala Ala Ser Phe Ile Arg Gln Ala Arg Ser Ile Thr His
            100                 105                 110

Ala Leu Ala Pro Pro Gln Ile Asn Arg Trp Thr Ala Glu Ala Leu Val
        115                 120                 125

Ala Leu Gln Glu Ala Ala Glu Asp Tyr Leu Val Gly Leu Phe Ser Asp
    130                 135                 140

Ser Met Leu Cys Ala Ile His Ala Arg Arg Val Thr Leu Met Arg Lys
145                 150                 155                 160

Asp Phe Glu Leu Ala Arg Arg Leu Gly Gly Lys Gly Arg Pro Trp
                165                 170                 175

<210> SEQ ID NO 46
<211> LENGTH: 172
<212> TYPE: PRT
<213> ORGANISM: Arabidopsis lyrata
<220> FEATURE:
<223> OTHER INFORMATION: lyre-leaved rockcress histone H3 (HTR12B)

<400> SEQUENCE: 46

Met Ala Arg Thr Lys His Phe Ala Thr Lys Ser Arg Thr Asp Ala Asn
1               5                   10                  15

Ala Ser Ser Ser Gln Ala Ala Gly Pro Thr Thr Thr Pro Thr Thr Arg
            20                  25                  30

Gly Thr Glu Gly Gly Asp Asn Thr Gln Gln Thr Asn Pro Thr Thr Ser
        35                  40                  45

Pro Ala Thr Gly Gly Arg Arg Pro Arg Arg Ala Arg Gln Ala Met Pro
    50                  55                  60

Arg Gly Ser Gln Lys Lys Pro Tyr Arg Tyr Lys Pro Gly Thr Val Ala
65                  70                  75                  80

Leu Arg Glu Ile Arg His Phe Gln Lys Gln Thr Asn Leu Leu Ile Pro
                85                  90                  95

Ala Ala Ser Phe Ile Arg Gln Val Arg Ser Ile Thr His Ala Leu Ala
            100                 105                 110

Pro Pro Gln Ile Asn Arg Trp Thr Ala Glu Ala Leu Val Ala Leu Gln
        115                 120                 125

Glu Ala Ala Glu Asp Tyr Leu Val Gly Leu Phe Ser Asp Ser Met Leu
    130                 135                 140

Cys Ala Ile His Ala Arg Arg Val Thr Leu Met Arg Lys Asp Phe Glu
145                 150                 155                 160

Leu Ala Arg Arg Leu Gly Gly Lys Gly Arg Pro Trp
                165                 170

<210> SEQ ID NO 47
<211> LENGTH: 163
<212> TYPE: PRT
<213> ORGANISM: Saccharum officinalis
<220> FEATURE:
<223> OTHER INFORMATION: sugarcane CENH3

<400> SEQUENCE: 47

Met Ala Arg Thr Lys His Gln Ala Val Arg Arg Pro Thr Gln Lys Pro
1               5                   10                  15

Lys Lys Lys Leu Gln Phe Glu Arg Ala Gly Gly Ala Ser Thr Ser Ala
            20                  25                  30

Thr Pro Glu Arg Asn Ala Gly Thr Gly Gly Gly Ala Ala Ala Arg Val
        35                  40                  45
```

Thr Arg Gly Arg Val Glu Lys His Arg Trp Arg Val Gly Thr Val
    50                  55                  60

Ala Leu Arg Glu Ile Arg Lys Tyr Gln Lys Ser Thr Glu Pro Leu Ile
65                  70                  75                  80

Pro Phe Ala Pro Phe Val Arg Val Lys Glu Leu Thr Gly Phe Ile
                85                  90                  95

Thr Asp Trp Arg Ile Gly Arg Tyr Thr Pro Glu Ala Leu Leu Ala Leu
                100                 105                 110

Gln Glu Ala Ala Glu Phe His Leu Ile Glu Leu Phe Gln Val Ala Asn
            115                 120                 125

Leu Cys Ala Ile His Ala Lys Arg Val Thr Val Met Gln Lys Asp Ile
            130                 135                 140

Gln Leu Ala Arg Arg Ile Gly Gly Lys Arg Trp Ala Tyr Pro Phe Phe
145                 150                 155                 160

Leu Pro Tyr

<210> SEQ ID NO 48
<211> LENGTH: 181
<212> TYPE: PRT
<213> ORGANISM: Brassica napa
<220> FEATURE:
<223> OTHER INFORMATION: turnip CENH3

<400> SEQUENCE: 48

Met Ala Arg Thr Lys His Phe Ala Ser Arg Ala Arg Asp Arg Asn Pro
1                   5                   10                  15

Thr Asn Ala Thr Ala Ser Ser Ala Ala Ala Ala Gly Pro Ser
                20                  25                  30

Ala Thr Pro Thr Arg Arg Gly Gly Ser Gln Gly Gly Glu Ala Gln Gln
            35                  40                  45

Thr Thr Pro Pro Ala Thr Thr Thr Ala Gly Arg Lys Lys Gly Gly Thr
    50                  55                  60

Lys Arg Thr Lys Gln Ala Met Pro Lys Ser Ser Asn Lys Lys Lys Thr
65                  70                  75                  80

Phe Arg Tyr Lys Pro Gly Thr Val Ala Leu Arg Glu Ile Arg His Phe
                85                  90                  95

Gln Lys Thr Thr Lys Leu Leu Ile Pro Ala Ala Ser Phe Ile Arg Glu
                100                 105                 110

Val Arg Ser Val Thr Gln Ile Phe Ala Pro Pro Asp Val Thr Arg Trp
            115                 120                 125

Thr Ala Glu Ala Leu Met Ala Ile Gln Glu Ala Ala Glu Asp Phe Leu
            130                 135                 140

Val Gly Leu Phe Ser Asp Ala Met Leu Cys Ala Ile His Ala Arg Arg
145                 150                 155                 160

Val Thr Leu Met Arg Lys Asp Phe Glu Leu Ala Arg Arg Leu Gly Gly
                165                 170                 175

Lys Gly Arg Pro Leu
            180

<210> SEQ ID NO 49
<211> LENGTH: 91
<212> TYPE: PRT
<213> ORGANISM: Artificial Sequence
<220> FEATURE:
<223> OTHER INFORMATION: Physcomitrella patens moss CENH3 histone domain

<400> SEQUENCE: 49

```
Pro Gly Thr Lys Ala Leu Gln Glu Ile Arg His Tyr Gln Lys Thr Cys
1               5                   10                  15

Asp Leu Leu Ile Pro Arg Leu Pro Phe Ala Arg Tyr Val Lys Glu Ile
                20              25                  30

Thr Met Met Tyr Ala Ser Asp Val Ser Arg Trp Thr Glu Ala Leu
            35                  40                  45

Thr Ala Leu Gln Glu Ala Thr Glu Asp Tyr Met Cys His Leu Phe Glu
    50                  55                  60

Asp Thr Asn Leu Cys Ala Ile His Ala Lys Val Thr Ile Met Pro
65                  70                  75                  80

Lys Asp Leu Gln Leu Ala Arg Arg Leu Arg Gly
                85                  90
```

<210> SEQ ID NO 50
<211> LENGTH: 98
<212> TYPE: PRT
<213> ORGANISM: Artificial Sequence
<220> FEATURE:
<223> OTHER INFORMATION: Pinus taeda loblolly pine CENH3 histone domain

<400> SEQUENCE: 50

```
Pro Gly Thr Val Ala Leu Arg Glu Ile Lys Arg Tyr Gln Lys Ser Phe
1               5                   10                  15

Glu Leu Leu Ile Pro Ser Leu Pro Phe Ala Arg Ile Val Arg Glu Leu
                20                  25                  30

Thr Met Tyr Tyr Ser Gln Val Val Ser Arg Trp Ala Ala Glu Ala Leu
            35                  40                  45

Val Ala Leu Gln Glu Ala Ala Glu Asp Tyr Ile Val His Leu Phe Glu
    50                  55                  60

Asp Thr Asn Leu Cys Ala Ile His Ala Lys Arg Val Thr Ile Met Pro
65                  70                  75                  80

Arg Asp Leu Arg Leu Ala Arg Arg Leu Arg Gly Gly Gly Leu Asp Arg
                85                  90                  95

Pro Trp
```

<210> SEQ ID NO 51
<211> LENGTH: 97
<212> TYPE: PRT
<213> ORGANISM: Artificial Sequence
<220> FEATURE:
<223> OTHER INFORMATION: synthetic Boechera holboellii Holboell's
      rockcress CENH3 histone domain

<400> SEQUENCE: 51

```
Pro Gly Thr Val Ala Leu Arg Glu Ile Arg Tyr Phe Gln Lys Ser Ile
1               5                   10                  15

Asn Leu Leu Ile Pro Ala Ala Ser Phe Ile Arg Gln Val Arg Ser Ile
                20                  25                  30

Thr His Ala Leu Ala Pro Pro Gln Ile Thr Arg Trp Thr Ala Glu Ala
            35                  40                  45

Leu Val Ala Leu Gln Glu Ala Ala Glu Asp Tyr Leu Val Gly Leu Phe
    50                  55                  60

Ser Asp Ser Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Trp
```

```
<210> SEQ ID NO 52
<211> LENGTH: 97
<212> TYPE: PRT
<213> ORGANISM: Artificial Sequence
<220> FEATURE:
<223> OTHER INFORMATION: synthetic Boechera stricta Drummond's rockcress
      CENH3 histone domain

<400> SEQUENCE: 52

Pro Gly Thr Val Ala Leu Arg Glu Ile Arg His Phe Gln Lys Ser Ile
1               5                   10                  15

Asn Leu Leu Ile Pro Ala Ala Ser Phe Ile Arg Gln Val Arg Ser Ile
            20                  25                  30

Thr His Ala Leu Ala Pro Pro Gln Ile Thr Arg Trp Thr Ala Glu Ala
        35                  40                  45

Leu Val Ala Leu Gln Glu Ala Ala Glu Asp Tyr Leu Val Gly Leu Phe
    50                  55                  60

Ser Asp Ser Met Leu Cys Ala Ile His Ala Arg Arg Ile Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 53
<211> LENGTH: 97
<212> TYPE: PRT
<213> ORGANISM: Artificial Sequence
<220> FEATURE:
<223> OTHER INFORMATION: synthetic Lepidum virginicum Virginia
      pepperweed CENH3 histone domain

<400> SEQUENCE: 53

Pro Gly Thr Val Ala Leu Arg Glu Ile Arg His Phe Gln Lys Ser Thr
1               5                   10                  15

His Leu Leu Ile Pro Ala Ala Ala Phe Ile Arg Glu Val Arg Cys Ile
            20                  25                  30

Thr Gln Ala Val Ala Pro Pro Gln Ile Ser Arg Trp Thr Ala Glu Ala
        35                  40                  45

Leu Val Ala Leu Gln Glu Ala Ala Glu Asp Tyr Val Val Gly Leu Leu
    50                  55                  60

Ser Asp Ser Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 54
<211> LENGTH: 97
<212> TYPE: PRT
<213> ORGANISM: Artificial Sequence
<220> FEATURE:
<223> OTHER INFORMATION: synthetic Cardamine flexuosa woodland
      bittercress CENH3 histone domain

<400> SEQUENCE: 54

Pro Gly Thr Val Ala Leu Arg Glu Ile Arg His Phe Gln Lys Ser Thr
1               5                   10                  15

Asn Leu Leu Ile Pro Ala Ala Ser Phe Ile Arg Gln Val Arg Ser Ile
            20                  25                  30
```

```
Thr Gln Met Tyr Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
 50                  55                  60

Ser Asp Ser Met Leu Cys Ala Ile His Ala Arg Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 55
<211> LENGTH: 102
<212> TYPE: PRT
<213> ORGANISM: Artificial Sequence
<220> FEATURE:
<223> OTHER INFORMATION: Hordeum vulgare barley CENH3 histone domain

<400> SEQUENCE: 55

Pro Gly Thr Val Ala Leu Arg Glu Ile Arg Lys Tyr Arg Lys Ser Thr
 1               5                  10                  15

Asn Met Leu Ile Pro Phe Ala Pro Phe Val Arg Leu Val Arg Asp Ile
                20                  25                  30

Ala Asp Asn Leu Thr Pro Leu Ser Asn Lys Lys Glu Ser Lys Pro Thr
        35                  40                  45

Pro Trp Thr Pro Leu Ala Leu Leu Ser Leu Gln Glu Ser Ala Glu Tyr
 50                  55                  60

His Leu Val Asp Leu Phe Gly Lys Ala Asn Leu Cys Ala Ile His Ser
 65                  70                  75                  80

His Arg Val Thr Ile Met Leu Lys Asp Met Gln Leu Ala Arg Arg Ile
                 85                  90                  95

Gly Thr Arg Ser Leu Trp
            100

<210> SEQ ID NO 56
<211> LENGTH: 97
<212> TYPE: PRT
<213> ORGANISM: Artificial Sequence
<220> FEATURE:
<223> OTHER INFORMATION: synthetic Arabidopsis thaliana thale cress
      CENH3 histone domain

<400> SEQUENCE: 56

Pro Gly Thr Val Ala Leu Lys Glu Ile Arg His Phe Gln Lys Gln Thr
 1               5                  10                  15

Asn Leu Leu Ile Pro Ala Ala Ser Phe Ile Arg Glu Val Arg Ser Ile
                20                  25                  30

Thr His Met Leu Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
 50                  55                  60

Ser Asp Ser Met Leu Cys Ala Ile His Ala Arg Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 57
```

<211> LENGTH: 96
<212> TYPE: PRT
<213> ORGANISM: Artificial Sequence
<220> FEATURE:
<223> OTHER INFORMATION: synthetic Populus trichocarpa black cottonwood
      CENH3 histone domain

<400> SEQUENCE: 57

Ser Gly Thr Val Ala Leu Arg Glu Ile Arg Gln Tyr Gln Lys Thr Trp
1               5                   10                  15

Arg Pro Leu Ile Pro Ala Ala Ser Phe Ile Arg Cys Val Arg Met Ile
                20                  25                  30

Thr Gln Glu Phe Ser Arg Glu Val Asn Arg Trp Thr Ala Glu Ala Leu
            35                  40                  45

Val Ala Ile Gln Glu Ala Ala Glu Asp Phe Leu Val His Leu Phe Glu
    50                  55                  60

Asp Gly Met Leu Cys Ala Ile His Ala Lys Arg Val Thr Leu Met Lys
65                  70                  75                  80

Lys Asp Phe Glu Leu Ala Arg Arg Leu Gly Gly Lys Gly Arg Pro Trp
                85                  90                  95

<210> SEQ ID NO 58
<211> LENGTH: 95
<212> TYPE: PRT
<213> ORGANISM: Artificial Sequence
<220> FEATURE:
<223> OTHER INFORMATION: synthetic Triticum aestivum wheat CENH3 histone
      domain

<400> SEQUENCE: 58

Pro Gly Thr Val Ala Leu Arg Glu Ile Arg Lys Tyr Gln Lys Ser Val
1               5                   10                  15

Asp Phe Leu Ile Pro Phe Ala Pro Phe Val Arg Leu Ile Lys Glu Val
                20                  25                  30

Thr Asp Phe Phe Cys Pro Glu Ile Ser Arg Trp Thr Pro Gln Ala Leu
            35                  40                  45

Val Ala Ile Gln Glu Ala Ala Glu Tyr His Leu Val Asp Val Phe Glu
    50                  55                  60

Arg Ala Asn His Cys Ala Ile His Ala Lys Arg Val Thr Val Met Gln
65                  70                  75                  80

Lys Asp Ile Gln Leu Ala Arg Arg Ile Gly Gly Arg Arg Leu Trp
                85                  90                  95

<210> SEQ ID NO 59
<211> LENGTH: 101
<212> TYPE: PRT
<213> ORGANISM: Artificial Sequence
<220> FEATURE:
<223> OTHER INFORMATION: synthetic Oryza sativa rice CENH3 histone
      domain

<400> SEQUENCE: 59

Pro Gly Thr Val Ala Leu Arg Glu Ile Arg Lys Phe Gln Lys Thr Thr
1               5                   10                  15

Glu Leu Leu Ile Pro Phe Ala Pro Phe Ser Arg Leu Val Arg Glu Ile
                20                  25                  30

Thr Asp Phe Tyr Ser Lys Asp Val Ser Arg Trp Thr Leu Glu Ala Leu
            35                  40                  45

Leu Ala Leu Gln Glu Ala Ala Glu Tyr His Leu Val Asp Ile Phe Glu
    50                  55                  60

```
Val Ser Asn Leu Cys Ala Ile His Ala Lys Arg Val Thr Ile Met Gln
 65                  70                  75                  80

Lys Asp Met Gln Leu Ala Arg Arg Ile Gly Gly Arg Arg Pro Trp Asn
                 85                  90                  95

Leu Asn Ser Leu Arg
            100
```

<210> SEQ ID NO 60
<211> LENGTH: 91
<212> TYPE: PRT
<213> ORGANISM: Artificial Sequence
<220> FEATURE:
<223> OTHER INFORMATION: synthetic Luzula nivea snowy woodrush CENH3
      histone domain

<400> SEQUENCE: 60

```
Pro Gly Thr Val Ala Leu Arg Glu Ile Arg Lys Leu Gln Lys Thr Thr
 1               5                  10                  15

Asp Leu Leu Val Pro Lys Ala Ser Phe Ala Arg Leu Val Lys Glu Ile
                 20                  25                  30

Thr Phe Gln Ser Ser Lys Glu Val Asn Arg Trp Gln Ala Glu Ala Leu
             35                  40                  45

Ile Ala Leu Gln Glu Ala Ser Glu Cys Phe Leu Val Asn Leu Leu Glu
 50                  55                  60

Ser Ala Asn Met Leu Ala Ile His Ala Arg Arg Val Thr Ile Met Lys
 65                  70                  75                  80

Lys Asp Ile Gln Leu Ala Arg Arg Ile Gly Ala
                 85                  90
```

<210> SEQ ID NO 61
<211> LENGTH: 97
<212> TYPE: PRT
<213> ORGANISM: Artificial Sequence
<220> FEATURE:
<223> OTHER INFORMATION: synthetic Arabidopsis arenosa sand rockcress
      CENH3 histone domain

<400> SEQUENCE: 61

```
Pro Gly Thr Val Ala Leu Arg Glu Ile Arg His Phe Gln Lys Gln Thr
 1               5                  10                  15

Asn Leu Leu Ile Pro Ala Ala Ser Phe Ile Arg Gln Val Arg Ser Ile
                 20                  25                  30

Thr His Ala Leu Ala Pro Pro Gln Ile Asn Arg Trp Thr Ala Glu Ala
             35                  40                  45

Leu Val Ala Leu Gln Glu Ala Ala Glu Asp Tyr Leu Ile Gly Leu Phe
 50                  55                  60

Ser Asp Ser Met Leu Cys Ala Ile His Ala Arg Arg Val Thr Leu Met
 65                  70                  75                  80

Arg Lys Asp Phe Glu Leu Ala Arg Arg Leu Gly Gly Lys Gly Arg Pro
                 85                  90                  95

Trp
```

<210> SEQ ID NO 62
<211> LENGTH: 96
<212> TYPE: PRT
<213> ORGANISM: Artificial Sequence
<220> FEATURE:
<223> OTHER INFORMATION: synthetic Zea mays corn CENH3 histone domain

<400> SEQUENCE: 62

```
Pro Gly Thr Val Ala Leu Arg Glu Ile Arg Lys Tyr Gln Lys Ser Thr
1               5                   10                  15

Glu Pro Leu Ile Pro Phe Ala Pro Phe Val Arg Val Arg Glu Leu
            20                  25                  30

Thr Asn Phe Val Thr Asn Gly Lys Val Glu Arg Tyr Thr Ala Glu Ala
            35                  40                  45

Leu Leu Ala Leu Gln Glu Ala Ala Glu Phe His Leu Ile Glu Leu Phe
        50                  55                  60

Glu Met Ala Asn Leu Cys Ala Ile His Ala Lys Arg Val Thr Ile Met
65                  70                  75                  80

Gln Lys Asp Ile Gln Leu Ala Arg Arg Ile Gly Gly Arg Arg Trp Ala
                85                  90                  95
```

<210> SEQ ID NO 63
<211> LENGTH: 96
<212> TYPE: PRT
<213> ORGANISM: Artificial Sequence
<220> FEATURE:
<223> OTHER INFORMATION: synthetic Sorghum bicolor sorghum CENH3 histone domain

<400> SEQUENCE: 63

```
Ala Gly Thr Val Ala Leu Arg Glu Ile Arg Lys Tyr Gln Lys Ser Thr
1               5                   10                  15

Glu Pro Leu Ile Pro Phe Ala Pro Phe Val Arg Val Val Lys Glu Leu
            20                  25                  30

Thr Ala Phe Ile Thr Asp Trp Arg Ile Gly Arg Tyr Thr Pro Glu Ala
            35                  40                  45

Leu Leu Ala Leu Gln Glu Ala Ala Glu Phe His Leu Ile Glu Leu Phe
        50                  55                  60

Glu Val Ala Asn Leu Cys Ala Ile His Ala Lys Arg Val Thr Val Met
65                  70                  75                  80

Gln Lys Asp Ile Gln Leu Ala Arg Arg Ile Gly Gly Arg Arg Trp Ser
                85                  90                  95
```

<210> SEQ ID NO 64
<211> LENGTH: 96
<212> TYPE: PRT
<213> ORGANISM: Artificial Sequence
<220> FEATURE:
<223> OTHER INFORMATION: synthetic Cichorium intybus chicory CENH3 histone domain

<400> SEQUENCE: 64

```
Pro Gly Ala Gln Ala Leu Arg Glu Ile Arg Arg Leu Gln Lys Thr Val
1               5                   10                  15

Asn Leu Leu Ile Pro Ala Ala Pro Phe Ile Arg Thr Val Lys Glu Ile
            20                  25                  30

Ser Asn Tyr Ile Ala Pro Glu Val Thr Arg Trp Gln Ala Glu Ala Ile
            35                  40                  45

Gln Ala Leu Gln Glu Ala Ala Glu Asp Tyr Leu Val Gln Leu Phe Glu
        50                  55                  60

Asp Ser Met Leu Cys Ser Ile His Ala Lys Arg Val Thr Leu Met Lys
65                  70                  75                  80

Lys Asp Trp Glu Leu Ala Arg Arg Leu Thr Lys Lys Gly Gln Pro Trp
                85                  90                  95
```

<210> SEQ ID NO 65
<211> LENGTH: 87

```
<212> TYPE: PRT
<213> ORGANISM: Artificial Sequence
<220> FEATURE:
<223> OTHER INFORMATION: synthetic Cycas rumphii queen sago CENH3
      histone domain

<400> SEQUENCE: 65

Pro Gly Thr Val Ala Leu Arg Glu Ile Arg Arg Tyr Gln Lys Ser Phe
1               5                   10                  15

Glu Leu Leu Ile Pro Ala Leu Pro Phe Ala Arg Asn Val Arg Glu Leu
            20                  25                  30

Thr Leu His His Ser Arg Glu Val His Arg Trp Thr Ala Glu Ala Leu
        35                  40                  45

Val Ala Leu Gln Glu Ala Ala Glu Asp Tyr Ile Val His Leu Phe Glu
50                  55                  60

Asp Thr Asn Leu Cys Ala Ile His Ala Lys Arg Val Thr Ile Met Pro
65                  70                  75                  80

Lys Asp Met His Leu Ala Arg
                85

<210> SEQ ID NO 66
<211> LENGTH: 96
<212> TYPE: PRT
<213> ORGANISM: Artificial Sequence
<220> FEATURE:
<223> OTHER INFORMATION: synthetic Allium cepa onion CENH3 histone
      domain

<400> SEQUENCE: 66

Pro Gly Thr Val Ala Leu Arg Glu Ile Arg Lys Tyr Gln Lys Thr Ala
1               5                   10                  15

Glu Leu Leu Ile Pro Ala Ala Pro Phe Ile Arg Leu Val Arg Glu Ile
            20                  25                  30

Thr Asn Leu Tyr Ser Lys Glu Val Thr Arg Trp Thr Pro Glu Ala Leu
        35                  40                  45

Leu Ala Ile Gln Glu Ala Ala Glu Phe Phe Ile Ile Asn Leu Leu Glu
50                  55                  60

Glu Ala Asn Leu Cys Ala Ile His Ala Lys Arg Val Thr Leu Met Gln
65                  70                  75                  80

Lys Asp Ile Gln Leu Ala Arg Arg Ile Gly Gly Ala Arg His Phe Ser
                85                  90                  95

<210> SEQ ID NO 67
<211> LENGTH: 89
<212> TYPE: PRT
<213> ORGANISM: Artificial Sequence
<220> FEATURE:
<223> OTHER INFORMATION: synthetic Malus domestica apple CENH3 histone
      domain

<400> SEQUENCE: 67

Pro Gly Thr Val Ala Leu Arg Glu Ile Arg Tyr Tyr Gln Lys Thr Trp
1               5                   10                  15

Asn Leu Ile Ile Pro Ala Ala Pro Phe Ile Arg Thr Val Arg Glu Ile
            20                  25                  30

Ser Ile Asn Met Ser Lys Asp Pro Val Arg Trp Thr Pro Glu Ala Leu
        35                  40                  45

Gln Ala Ile Gln Glu Ala Ala Glu Asp Phe Leu Val Arg Leu Phe Glu
50                  55                  60

Asp Ser Met Leu Cys Ala Ile His Ala Arg Arg Val Thr Leu Met Lys
```

65                  70                  75                  80

Lys Asp Leu Glu Leu Ala Arg Arg Ile
                85

<210> SEQ ID NO 68
<211> LENGTH: 96
<212> TYPE: PRT
<213> ORGANISM: Artificial Sequence
<220> FEATURE:
<223> OTHER INFORMATION: synthetic Lactuca sativa lettuce CENH3 histone
      domain

<400> SEQUENCE: 68

Pro Gly Thr Gln Ala Leu Arg Glu Ile Arg Arg Leu Gln Lys Thr Val
1               5                   10                  15

Asn Leu Leu Ile Pro Ala Ala Pro Phe Ile Arg Thr Val Lys Glu Ile
                20                  25                  30

Ser Asn Tyr Ile Ala Pro Glu Val Thr Arg Trp Gln Ala Glu Ala Leu
            35                  40                  45

Gln Ala Leu Gln Glu Ala Ala Glu Asp Tyr Ile Val Gln Leu Phe Glu
        50                  55                  60

Asp Ser Met Leu Cys Ser Ile His Ala Lys Arg Val Thr Leu Met Lys
65                  70                  75                  80

Lys Asp Met Glu Leu Ala Arg Arg Leu Thr Lys Lys Gly Gln Pro Trp
                85                  90                  95

<210> SEQ ID NO 69
<211> LENGTH: 96
<212> TYPE: PRT
<213> ORGANISM: Artificial Sequence
<220> FEATURE:
<223> OTHER INFORMATION: synthetic Carthamus tinctorius safflower CENH3
      histone domain

<400> SEQUENCE: 69

Pro Gly Thr Gln Ala Leu Arg Glu Ile Arg Arg Leu Gln Lys Thr Val
1               5                   10                  15

Asn Leu Leu Ile Pro Ala Ala Pro Phe Ile Arg Thr Val Lys Glu Ile
                20                  25                  30

Ser Asn Tyr Ile Ala Pro Glu Val Thr Arg Trp Gln Ala Glu Ala Leu
            35                  40                  45

Gln Ala Leu Gln Glu Ala Ala Glu Asp Tyr Leu Ile Gln Leu Phe Glu
        50                  55                  60

Asp Ser Met Leu Cys Ala Ile His Ala Lys Arg Val Thr Leu Met Lys
65                  70                  75                  80

Lys Asp Trp Glu Leu Ala Arg Arg Leu Gly Lys Lys Gly Gln Pro Trp
                85                  90                  95

<210> SEQ ID NO 70
<211> LENGTH: 96
<212> TYPE: PRT
<213> ORGANISM: Artificial Sequence
<220> FEATURE:
<223> OTHER INFORMATION: synthetic Helianthus exilis serpentine
      sunflower CENH3 histone domain

<400> SEQUENCE: 70

Pro Gly Thr Gln Ala Leu Arg Glu Ile Arg Arg Leu Gln Lys Thr Val
1               5                   10                  15

Glu Leu Ile Ile Pro Ala Ala Pro Phe Ile Arg Thr Val Lys Glu Ile
                20                  25                  30

```
Ser Asn Tyr Met Ala Pro Glu Ile Thr Arg Trp Gln Ala Glu Ala Leu
        35                  40                  45

Gln Ala Leu Gln Glu Ala Ala Glu Asp Tyr Leu Ile Gln Leu Phe Glu
    50                  55                  60

Asp Ser Met Leu Cys Ala Ile His Ala Lys Arg Val Thr Leu Met Lys
65                  70                  75                  80

Lys Asp Trp Glu Leu Ala Arg Arg Ile Gly Lys Lys Gly Gln Pro Trp
                85                  90                  95

<210> SEQ ID NO 71
<211> LENGTH: 95
<212> TYPE: PRT
<213> ORGANISM: Artificial Sequence
<220> FEATURE:
<223> OTHER INFORMATION: synthetic Gossypium hirsutum upland cotton
      CENH3 histone domain

<400> SEQUENCE: 71

Ala Gly Thr Arg Ala Leu Gln Glu Ile Arg Lys Tyr Gln Lys Thr Ser
1               5                   10                  15

Asn Leu Leu Val Pro Ala Ala Ser Phe Ile Arg Glu Val Arg Ala Ile
                20                  25                  30

Ser Tyr Arg Phe Ala Pro Asp Ile Asn Arg Trp Gln Ala Glu Ala Leu
        35                  40                  45

Val Ala Ile Gln Glu Ala Ala Glu Asp Tyr Leu Ile Gln Leu Phe Gly Asp
    50                  55                  60

Ala Met Leu Cys Ala Ile His Ala Lys Arg Val Thr Leu Met Lys Lys
65                  70                  75                  80

Asp Ile Gln Leu Ala Arg Arg Leu Gly Gly Met Gly Gln Pro Trp
                85                  90                  95

<210> SEQ ID NO 72
<211> LENGTH: 93
<212> TYPE: PRT
<213> ORGANISM: Artificial Sequence
<220> FEATURE:
<223> OTHER INFORMATION: Glycine max soybean CENH3 histone domain

<400> SEQUENCE: 72

Ser Gly Thr Val Ala Leu Arg Glu Ile Arg His Phe Gln Arg Ser Cys
1               5                   10                  15

Glu Leu Leu Ile Pro Ala Ala Pro Phe Ile Arg Cys Val Lys Gln Ile
                20                  25                  30

Thr Asn Gln Phe Ser Thr Glu Val Ser Arg Trp Thr Pro Glu Ala Val
        35                  40                  45

Val Ala Leu Gln Glu Ala Ala Glu Glu Tyr Leu Val His Leu Phe Glu
    50                  55                  60

Asp Gly Met Leu Cys Ala Ile His Ala Arg Arg Ile Thr Leu Met Lys
65                  70                  75                  80

Lys Asp Ile Glu Leu Ala Arg Arg Leu Gly Gly Ile Gly
                85                  90

<210> SEQ ID NO 73
<211> LENGTH: 96
<212> TYPE: PRT
<213> ORGANISM: Artificial Sequence
<220> FEATURE:
<223> OTHER INFORMATION: Cucumis melo cantaloupe CENH3 histone domain

<400> SEQUENCE: 73
```

Pro Gly Thr Val Ala Leu Arg Glu Ile Arg Asn Leu Gln Lys Ser Trp
1               5                   10                  15

Asn Leu Leu Ile Pro Ala Ser Cys Phe Ile Arg Ala Val Lys Glu Val
            20                  25                  30

Ser Asn Gln Leu Ala Pro Gln Ile Thr Arg Trp Gln Ala Glu Ala Leu
        35                  40                  45

Val Ala Leu Gln Glu Ala Ala Glu Asp Phe Leu Val His Leu Phe Glu
    50                  55                  60

Asp Thr Met Leu Cys Ala Ile His Ala Lys Arg Val Thr Ile Met Lys
65                  70                  75                  80

Lys Asp Phe Glu Leu Ala Arg Arg Leu Gly Gly Lys Gly Arg Pro Trp
                85                  90                  95

<210> SEQ ID NO 74
<211> LENGTH: 96
<212> TYPE: PRT
<213> ORGANISM: Artificial Sequence
<220> FEATURE:
<223> OTHER INFORMATION: Solanum chacoense Chaco potato CENH3 histone
      domain

<400> SEQUENCE: 74

Pro Gly Ser Val Ala Leu Arg Glu Ile Arg His Phe Gln Lys Thr Trp
1               5                   10                  15

Asn Leu Val Ile Pro Ala Ala Pro Phe Ile Arg Leu Val Arg Glu Ile
            20                  25                  30

Ser His Phe Phe Ala Pro Gly Val Thr Arg Trp Gln Ala Glu Ala Leu
        35                  40                  45

Ile Ala Ile Gln Glu Ala Ala Glu Asp Phe Leu Val His Leu Phe Glu
    50                  55                  60

Asp Ala Met Leu Cys Ala Ile His Ala Lys Arg Val Thr Leu Met Lys
65                  70                  75                  80

Lys Asp Phe Glu Leu Ala Arg Arg Leu Gly Gly Lys Gly Gln Pro Trp
                85                  90                  95

<210> SEQ ID NO 75
<211> LENGTH: 96
<212> TYPE: PRT
<213> ORGANISM: Artificial Sequence
<220> FEATURE:
<223> OTHER INFORMATION: synthetic Solanum lycopersicum tomato CENH3
      histone domain

<400> SEQUENCE: 75

Pro Gly Thr Val Ala Leu Arg Glu Ile Arg His Phe Gln Lys Thr Trp
1               5                   10                  15

Asp Leu Leu Ile Pro Ala Ala Pro Phe Ile Arg Leu Val Arg Glu Ile
            20                  25                  30

Ser His Phe Tyr Ala Pro Gly Val Thr Arg Trp Gln Ala Glu Ala Leu
        35                  40                  45

Ile Ala Ile Gln Glu Ala Ala Glu Asp Phe Leu Val His Leu Phe Glu
    50                  55                  60

Asp Ala Met Leu Cys Ala Ile His Ala Lys Arg Val Thr Leu Met Lys
65                  70                  75                  80

Lys Asp Phe Glu Leu Ala Arg Arg Leu Gly Gly Lys Gly Gln Pro Trp
                85                  90                  95

<210> SEQ ID NO 76

<211> LENGTH: 96
<212> TYPE: PRT
<213> ORGANISM: Artificial Sequence
<220> FEATURE:
<223> OTHER INFORMATION: synthetic Nicotiana tabacum allotetraploid
      tobacco CENH3-1 histone domain

<400> SEQUENCE: 76

Pro Gly Thr Val Ala Leu Arg Glu Ile Arg Arg Phe Gln Lys Thr Trp
1               5                   10                  15

Asp Leu Leu Ile Pro Ala Ala Pro Phe Ile Arg Leu Val Lys Glu Ile
            20                  25                  30

Ser His Phe Phe Ala Pro Glu Val Thr Arg Trp Gln Ala Glu Ala Leu
        35                  40                  45

Ile Ala Leu Gln Glu Ala Ala Glu Asp Phe Leu Val His Leu Phe Asp
    50                  55                  60

Asp Ser Met Leu Cys Ala Ile His Ala Lys Arg Val Thr Leu Met Lys
65                  70                  75                  80

Lys Asp Phe Glu Leu Ala Arg Arg Leu Gly Gly Lys Ala Arg Pro Trp
                85                  90                  95

<210> SEQ ID NO 77
<211> LENGTH: 96
<212> TYPE: PRT
<213> ORGANISM: Artificial Sequence
<220> FEATURE:
<223> OTHER INFORMATION: synthetic Nicotiana tabacum allotetraploid
      tobacco CENH3-2 histone domain

<400> SEQUENCE: 77

Pro Gly Thr Val Ala Leu Arg Glu Ile Arg Arg Phe Gln Lys Thr Trp
1               5                   10                  15

Asn Leu Leu Ile Pro Ala Ala Pro Phe Ile Arg Leu Val Lys Glu Ile
            20                  25                  30

Ser Tyr Phe Phe Ala Pro Glu Val Thr Arg Trp Gln Ala Glu Ala Leu
        35                  40                  45

Ile Ala Leu Gln Glu Ala Ala Glu Asp Phe Leu Val His Leu Phe Asp
    50                  55                  60

Asp Ser Met Leu Cys Ala Ile His Ala Lys Arg Val Thr Leu Met Lys
65                  70                  75                  80

Lys Asp Phe Glu Leu Ala Arg Arg Leu Gly Gly Lys Ala Arg Pro Trp
                85                  90                  95

<210> SEQ ID NO 78
<211> LENGTH: 96
<212> TYPE: PRT
<213> ORGANISM: Artificial Sequence
<220> FEATURE:
<223> OTHER INFORMATION: synthetic Nicotiana tomentosiformis diploid
      tobacco CENH3 histone domain

<400> SEQUENCE: 78

Pro Gly Thr Val Ala Leu Arg Glu Ile Arg Arg Phe Gln Lys Thr Trp
1               5                   10                  15

Asp Leu Leu Ile Pro Ala Ala Pro Phe Ile Arg Leu Val Lys Glu Ile
            20                  25                  30

Ser His Phe Phe Ala Pro Glu Val Thr Arg Trp Gln Ala Glu Ala Leu
        35                  40                  45

Ile Ala Leu Gln Glu Ala Ala Glu Asp Phe Leu Val His Leu Phe Asp
    50                  55                  60

-continued

Asp Ser Met Leu Cys Ala Ile His Ala Lys Arg Val Thr Leu Met Lys
65                  70                  75                  80

Lys Asp Phe Glu Leu Ala Arg Arg Leu Gly Gly Lys Ala Arg Pro Trp
            85                  90                  95

<210> SEQ ID NO 79
<211> LENGTH: 96
<212> TYPE: PRT
<213> ORGANISM: Artificial Sequence
<220> FEATURE:
<223> OTHER INFORMATION: synthetic Vitis vinifera European wine grape
      CENH3 histone domain

<400> SEQUENCE: 79

Pro Gly Thr Val Ala Leu Arg Glu Ile Arg Arg Phe Gln Lys Thr Thr
1               5                   10                  15

His Leu Leu Ile Pro Ala Ala Pro Phe Ile Arg Thr Val Arg Glu Ile
            20                  25                  30

Ser Tyr Phe Phe Ala Pro Glu Ile Ser Arg Trp Thr Ala Glu Ala Leu
        35                  40                  45

Val Ala Leu Gln Glu Ala Ala Glu Asp Tyr Leu Val His Leu Phe Glu
    50                  55                  60

Asp Ala Met Leu Cys Ala Ile His Ala Lys Arg Val Thr Leu Met Lys
65                  70                  75                  80

Lys Asp Trp Glu Leu Ala Arg Arg Ile Gly Gly Lys Gly Gln Pro Trp
            85                  90                  95

<210> SEQ ID NO 80
<211> LENGTH: 96
<212> TYPE: PRT
<213> ORGANISM: Artificial Sequence
<220> FEATURE:
<223> OTHER INFORMATION: synthetic Nicotiana sylvestris woodland tobacco
      CENH3 histone domain

<400> SEQUENCE: 80

Pro Gly Thr Val Ala Leu Arg Glu Ile Arg Arg Phe Gln Lys Thr Trp
1               5                   10                  15

Asn Leu Leu Ile Pro Ala Ala Pro Phe Ile Arg Leu Val Lys Glu Ile
            20                  25                  30

Ser Tyr Phe Phe Ala Pro Glu Val Thr Arg Trp Gln Ala Glu Ala Leu
        35                  40                  45

Ile Ala Leu Gln Glu Ala Ala Glu Asp Phe Leu Val His Leu Phe Asp
    50                  55                  60

Asp Ser Met Leu Cys Ala Ile His Ala Lys Arg Val Thr Leu Met Lys
65                  70                  75                  80

Lys Asp Phe Glu Leu Ala Arg Arg Leu Gly Gly Lys Ala Arg Pro Trp
            85                  90                  95

<210> SEQ ID NO 81
<211> LENGTH: 97
<212> TYPE: PRT
<213> ORGANISM: Artificial Sequence
<220> FEATURE:
<223> OTHER INFORMATION: synthetic Crucihimalaya himalaica Himalayan
      rockcress CENH3 histone domain

<400> SEQUENCE: 81

Ala Gly Thr Val Ala Leu Arg Glu Ile Arg His Phe Gln Lys Asn Thr
1               5                   10                  15

Asn Leu Leu Ile Pro Ala Ala Ser Phe Ile Arg Gln Val Lys Ser Ile

```
                    20                  25                  30

Thr Tyr Ala Val Ala Pro Pro Gln Ile Thr Arg Trp Thr Ala Glu Ala
            35                  40                  45

Leu Val Ala Leu Gln Glu Ala Ala Glu Asp Tyr Leu Val Gly Leu Phe
        50                  55                  60

Ser Asp Ser Met Leu Cys Ala Ile His Ala Arg Val Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 82
<211> LENGTH: 97
<212> TYPE: PRT
<213> ORGANISM: Artificial Sequence
<220> FEATURE:
<223> OTHER INFORMATION: synthetic Arabidopsis lyrata lyre-leaved
      rockcress CENH3 histone domain

<400> SEQUENCE: 82

Pro Gly Thr Val Ala Leu Arg Glu Ile Arg His Phe Gln Lys Gln Thr
1               5                   10                  15

Asn Leu Leu Ile Pro Ala Ala Ser Phe Ile Arg Gln Val Arg Ser Ile
                20                  25                  30

Thr His Ala Leu Ala Pro Pro Gln Ile Asn Arg Trp Thr Ala Glu Ala
            35                  40                  45

Leu Val Ala Leu Gln Glu Ala Ala Glu Asp Tyr Leu Val Gly Leu Phe
        50                  55                  60

Ser Asp Ser Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 83
<211> LENGTH: 90
<212> TYPE: PRT
<213> ORGANISM: Artificial Sequence
<220> FEATURE:
<223> OTHER INFORMATION: synthetic Capsella bursapastoris shepherd's
      purse CENH3 histone domain

<400> SEQUENCE: 83

Pro Gly Thr Val Ala Leu Arg Glu Ile Arg His Tyr Gln Lys Gly Thr
1               5                   10                  15

Ser Leu Leu Ile Pro Ala Ala Ala Phe Ile Arg Gln Val Arg Ser Ile
                20                  25                  30

Thr Asn Ala Val Ala Pro Arg Glu Val Asn Arg Trp Thr Ala Glu Ala
            35                  40                  45

Leu Val Ala Leu Gln Glu Ala Ala Glu Asp Phe Leu Val Gly Leu Phe
        50                  55                  60

Ser Asp Ser Met Leu Cys Ala Ile His Ala Arg Arg Val Thr Leu Met
65                  70                  75                  80

Arg Lys Asp Phe Asp Leu Ala Arg Arg Leu
                85                  90

<210> SEQ ID NO 84
<211> LENGTH: 97
```

```
<212> TYPE: PRT
<213> ORGANISM: Artificial Sequence
<220> FEATURE:
<223> OTHER INFORMATION: synthetic Raphanus sativus radish CENH3 histone
      domain

<400> SEQUENCE: 84

Pro Gly Thr Val Ala Leu Arg Glu Ile Arg His Phe Gln Lys Ser Thr
1               5                   10                  15

Lys Leu Leu Ile Pro Ser Ala Pro Phe Ile Arg Glu Val Arg Ser Ile
            20                  25                  30

Thr His Asn Leu Ala Ala Ala Tyr Val Thr Arg Trp Thr Ala Glu Ala
        35                  40                  45

Leu Ile Ala Leu Gln Glu Ala Ala Glu Asp Phe Leu Val Gly Leu Phe
    50                  55                  60

Ser Asp Ala Met Leu Cys Ala Ile His Ala Lys Arg Val Thr Leu Met
65                  70                  75                  80

Arg Lys Asp Phe Glu Leu Ala Arg Arg Leu Gly Gly Lys Gly Arg Pro
                85                  90                  95

Phe

<210> SEQ ID NO 85
<211> LENGTH: 97
<212> TYPE: PRT
<213> ORGANISM: Artificial Sequence
<220> FEATURE:
<223> OTHER INFORMATION: synthetic Eruca sativa arugula CENH3 histone
      domain

<400> SEQUENCE: 85

Pro Gly Thr Val Ala Leu Arg Glu Ile Arg His Phe Gln Lys Thr Thr
1               5                   10                  15

Lys Leu Leu Ile Pro Ala Ala Thr Phe Ile Arg Leu Val Arg Ser Ile
            20                  25                  30

Thr Leu Asp Arg Ala Lys Pro Gln Val Thr Arg Trp Thr Ala Glu Ala
        35                  40                  45

Leu Val Ala Leu Gln Glu Ala Ala Glu Asp Tyr Leu Val Gly Leu Phe
    50                  55                  60

Ser Asp Ser Met Leu Cys Ala Ile His Ala Lys Arg Val Thr Leu Met
65                  70                  75                  80

Arg Lys Asp Phe Glu Leu Ala Arg Arg Leu Gly Lys Gly Arg Pro
                85                  90                  95

Trp

<210> SEQ ID NO 86
<211> LENGTH: 97
<212> TYPE: PRT
<213> ORGANISM: Artificial Sequence
<220> FEATURE:
<223> OTHER INFORMATION: synthetic Olimarabidopsis pumila dwarf rocket
      CENH3-1 histone domain

<400> SEQUENCE: 86

Pro Gly Thr Val Ala Leu Arg Glu Ile Arg His Phe Gln Lys Thr Thr
1               5                   10                  15

Ser Leu Leu Leu Pro Ala Ala Pro Phe Ile Arg Gln Val Arg Ser Ile
            20                  25                  30

Ser Ser Ala Leu Ala Pro Arg Glu Ile Thr Arg Trp Thr Ala Glu Ala
        35                  40                  45
```

Leu Val Ala Leu Gln Glu Ala Ala Glu Asp Tyr Leu Val Gly Leu Phe
                50                  55                  60

Ser Asp Ser Met Leu Cys Ala Ile His Ala Lys Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 87
<211> LENGTH: 97
<212> TYPE: PRT
<213> ORGANISM: Artificial Sequence
<220> FEATURE:
<223> OTHER INFORMATION: synthetic Olimarabidopsis pumila dwarf rocket
      CENH3-2 histone domain

<400> SEQUENCE: 87

Pro Gly Thr Val Ala Leu Arg Glu Ile Arg His Phe Gln Lys Thr Thr
 1               5                  10                  15

Ser Phe Leu Ile Pro Ala Ala Pro Phe Ile Arg Gln Val Arg Ser Ile
                20                  25                  30

Ser Ser Ala Leu Ala Pro Thr Gln Ile Thr Arg Trp Thr Ala Glu Ala
                35                  40                  45

Leu Val Ala Leu Gln Glu Ala Ala Glu Asp Tyr Leu Val Gly Leu Phe
                50                  55                  60

Ser Asp Ser Met Leu Cys Ala Ile His Ala Lys Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 88
<211> LENGTH: 97
<212> TYPE: PRT
<213> ORGANISM: Artificial Sequence
<220> FEATURE:
<223> OTHER INFORMATION: synthetic Turritis glabra tower mustard CENH3
      histone domain

<400> SEQUENCE: 88

Pro Gly Thr Ile Ala Leu Arg Glu Ile Arg Tyr Phe Gln Lys Asn Thr
 1               5                  10                  15

Asn Leu Leu Ile Pro Ala Ala Ser Phe Ile Arg Glu Val Arg Ser Ile
                20                  25                  30

Thr His Ala Leu Ala Pro Pro Gln Ile Ser Arg Trp Thr Ala Glu Ala
                35                  40                  45

Leu Val Ala Leu Gln Glu Ala Ala Glu Asp Tyr Leu Val Gly Leu Phe
                50                  55                  60

Ser Asp Ser Met Leu Cys Ala Ile His Ala Arg Arg Val Thr Leu Met
 65                  70                  75                  80

Arg Lys Asp Phe Glu Leu Ala Arg Arg Ile Gly Gly Lys Gly Arg Pro
                 85                  90                  95

Trp

<210> SEQ ID NO 89
<211> LENGTH: 97
<212> TYPE: PRT
<213> ORGANISM: Artificial Sequence
<220> FEATURE:

<223> OTHER INFORMATION: synthetic Arabidopsis halleri CENH3-1 histone
domain

<400> SEQUENCE: 89

Pro Gly Thr Val Ala Leu Arg Glu Ile Arg His Phe Gln Lys Gln Thr
1               5                   10                  15

Asn Leu Leu Ile Pro Ala Ala Ser Phe Ile Arg Gln Val Arg Ser Ile
            20                  25                  30

Thr His Ala Leu Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
50                  55                  60

Ser Asp Ser Met Leu Cys Ala Ile His Ala Arg Arg Val Thr Leu Met
65                  70                  75                  80

Arg Lys Asp Phe Glu Leu Thr Arg Arg Leu Gly Gly Lys Gly Arg Pro
                85                  90                  95

Trp

<210> SEQ ID NO 90
<211> LENGTH: 97
<212> TYPE: PRT
<213> ORGANISM: Artificial Sequence
<220> FEATURE:
<223> OTHER INFORMATION: synthetic Arabidopsis halleri CENH3-2 histone
domain

<400> SEQUENCE: 90

Pro Gly Thr Val Ala Leu Arg Glu Ile Arg His Phe Gln Lys Gln Thr
1               5                   10                  15

Asn Leu Leu Ile Pro Ala Ala Ser Phe Ile Arg Gln Val Arg Ser Ile
            20                  25                  30

Thr His Ala Leu Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
50                  55                  60

Ser Asp Ser Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 91
<211> LENGTH: 97
<212> TYPE: PRT
<213> ORGANISM: Artificial Sequence
<220> FEATURE:
<223> OTHER INFORMATION: synthetic Arabidopsis lyrata CENH3 HTR12A
histone domain

<400> SEQUENCE: 91

Pro Gly Thr Val Ala Leu Arg Glu Ile Arg His Phe Gln Lys Gln Thr
1               5                   10                  15

Asn Leu Leu Ile Pro Ala Ala Ser Phe Ile Arg Gln Ala Arg Ser Ile
            20                  25                  30

Thr His Ala Leu Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
50                  55                  60

```
Ser Asp Ser Met Leu Cys Ala Ile His Ala Arg Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 92
<211> LENGTH: 97
<212> TYPE: PRT
<213> ORGANISM: Artificial Sequence
<220> FEATURE:
<223> OTHER INFORMATION: synthetic Arabidopsis lyrata CENH3 HTR12B
      histone domain

<400> SEQUENCE: 92

Pro Gly Thr Val Ala Leu Arg Glu Ile Arg His Phe Gln Lys Gln Thr
1               5                  10                  15

Asn Leu Leu Ile Pro Ala Ala Ser Phe Ile Arg Gln Val Arg Ser Ile
                20                  25                  30

Thr His Ala Leu Ala Pro Pro Gln Ile Asn Arg Trp Thr Ala Glu Ala
                35                  40                  45

Leu Val Ala Leu Gln Glu Ala Ala Glu Asp Tyr Leu Val Gly Leu Phe
        50                  55                  60

Ser Asp Ser Met Leu Cys Ala Ile His Ala Arg Arg Val Thr Leu Met
 65                  70                  75                  80

Arg Lys Asp Phe Glu Leu Ala Arg Arg Leu Gly Gly Lys Gly Arg Pro
                 85                  90                  95

Trp

<210> SEQ ID NO 93
<211> LENGTH: 103
<212> TYPE: PRT
<213> ORGANISM: Artificial Sequence
<220> FEATURE:
<223> OTHER INFORMATION: synthetic Saccharum officinalis sugarcane CENH3
      histone domain

<400> SEQUENCE: 93

Val Gly Thr Val Ala Leu Arg Glu Ile Arg Lys Tyr Gln Lys Ser Thr
1               5                  10                  15

Glu Pro Leu Ile Pro Phe Ala Pro Phe Val Arg Val Val Lys Glu Leu
                20                  25                  30

Thr Gly Phe Ile Thr Asp Trp Arg Ile Gly Arg Tyr Thr Pro Glu Ala
                35                  40                  45

Leu Leu Ala Leu Gln Glu Ala Ala Glu Phe His Leu Ile Glu Leu Phe
        50                  55                  60

Gln Val Ala Asn Leu Cys Ala Ile His Ala Lys Arg Val Thr Val Met
 65                  70                  75                  80

Gln Lys Asp Ile Gln Leu Ala Arg Arg Ile Gly Gly Lys Arg Trp Ala
                 85                  90                  95

Tyr Pro Phe Phe Leu Pro Tyr
                100

<210> SEQ ID NO 94
<211> LENGTH: 97
<212> TYPE: PRT
<213> ORGANISM: Artificial Sequence
<220> FEATURE:
<223> OTHER INFORMATION: synthetic Brassica napa turnip CENH3 histone
      domain
```

<400> SEQUENCE: 94

```
Pro Gly Thr Val Ala Leu Arg Glu Ile Arg His Phe Gln Lys Thr Thr
1               5                   10                  15

Lys Leu Leu Ile Pro Ala Ala Ser Phe Ile Arg Glu Val Arg Ser Val
                20                  25                  30

Thr Gln Ile Phe Ala Pro Pro Asp Val Thr Arg Trp Thr Ala Glu Ala
            35                  40                  45

Leu Met Ala Ile Gln Glu Ala Ala Glu Asp Phe Leu Val Gly Leu Phe
    50                  55                  60

Ser Asp Ala Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Leu
```

<210> SEQ ID NO 95
<211> LENGTH: 43
<212> TYPE: PRT
<213> ORGANISM: Artificial Sequence
<220> FEATURE:
<223> OTHER INFORMATION: synthetic conserved plant tail domain of H3 histone protein, N-terminal tail of H3, H3 tail

<400> SEQUENCE: 95

```
Met Ala Arg Thr Lys Gln Ser Ala Arg Lys Ser His Gly Gly Lys Ala
1               5                   10                  15

Pro Thr Lys Gln Leu Ala Thr Lys Ala Ala Arg Lys Ser Ala Pro Thr
                20                  25                  30

Thr Gly Gly Val Lys Lys Pro His Arg Phe Arg
            35                  40
```

<210> SEQ ID NO 96
<211> LENGTH: 705
<212> TYPE: PRT
<213> ORGANISM: Arabidopsis thaliana
<220> FEATURE:
<223> OTHER INFORMATION: thale cress centromere protein C (CENPC)

<400> SEQUENCE: 96

```
Met Ala Asp Val Ser Arg Ser Ser Ser Leu Tyr Thr Glu Glu Asp Pro
1               5                   10                  15

Leu Gln Ala Tyr Ser Gly Leu Ser Leu Phe Pro Arg Thr Leu Lys Ser
                20                  25                  30

Leu Ser Asn Pro Leu Pro Pro Ser Tyr Gln Ser Glu Asp Leu Gln Gln
            35                  40                  45

Thr His Thr Leu Leu Gln Ser Met Pro Phe Glu Ile Gln Ser Glu His
    50                  55                  60

Gln Glu Gln Ala Lys Ala Ile Leu Glu Asp Val Asp Val Asp Val Gln
65                  70                  75                  80

Leu Asn Pro Ile Pro Asn Lys Arg Glu Arg Arg Pro Gly Leu Asp Arg
                85                  90                  95

Lys Arg Lys Ser Phe Ser Leu His Leu Thr Thr Ser Gln Pro Pro Pro
                100                 105                 110

Val Ala Pro Ser Phe Asp Pro Ser Lys Tyr Pro Arg Ser Glu Asp Phe
            115                 120                 125

Phe Ala Ala Tyr Asp Lys Phe Glu Leu Ala Asn Arg Glu Trp Gln Lys
    130                 135                 140
```

```
Gln Thr Gly Ser Ser Val Ile Asp Ile Gln Glu Asn Pro Pro Ser Arg
145                 150                 155                 160

Arg Pro Arg Arg Pro Gly Ile Pro Gly Arg Lys Arg Pro Phe Lys
            165                 170                 175

Glu Ser Phe Thr Asp Ser Tyr Phe Thr Asp Val Ile Asn Leu Glu Ala
                180                 185                 190

Ser Glu Lys Glu Ile Pro Ile Ala Ser Glu Gln Ser Leu Glu Ser Ala
            195                 200                 205

Thr Ala Ala His Val Thr Thr Val Asp Arg Glu Val Asp Asp Ser Thr
        210                 215                 220

Val Asp Thr Asp Lys Asp Leu Asn Asn Val Leu Lys Asp Leu Leu Ala
225                 230                 235                 240

Cys Ser Arg Glu Glu Leu Glu Gly Asp Gly Ala Ile Lys Leu Leu Glu
                245                 250                 255

Glu Arg Leu Gln Ile Lys Ser Phe Asn Ile Glu Lys Phe Ser Ile Pro
            260                 265                 270

Glu Phe Gln Asp Val Arg Lys Met Asn Leu Lys Ala Ser Gly Ser Asn
        275                 280                 285

Pro Pro Asn Arg Lys Ser Leu Ser Asp Ile Gln Asn Ile Leu Lys Gly
        290                 295                 300

Thr Asn Arg Val Ala Val Arg Lys Asn Ser His Ser Pro Ser Pro Gln
305                 310                 315                 320

Thr Ile Lys His Phe Ser Ser Pro Asn Pro Pro Val Asp Gln Phe Ser
                325                 330                 335

Phe Pro Asp Ile His Asn Leu Leu Pro Gly Asp Gln Gln Pro Ser Glu
            340                 345                 350

Val Asn Val Gln Pro Ile Ala Lys Asp Ile Pro Asn Thr Ser Pro Thr
        355                 360                 365

Asn Val Gly Thr Val Asp Val Ala Ser Pro Phe Asn Asp Ser Val Val
370                 375                 380

Lys Arg Ser Gly Glu Asp Ser His Ile His Ser Gly Ile His Arg
385                 390                 395                 400

Ser His Leu Ser Arg Asp Gly Asn Pro Asp Ile Cys Val Met Asp Ser
                405                 410                 415

Ile Ser Asn Arg Ser Ser Ala Met Leu Gln Lys Asn Val Asp Met Arg
            420                 425                 430

Thr Lys Gly Lys Glu Val Asp Val Pro Met Ser Glu Ser Gly Ala Asn
        435                 440                 445

Arg Asn Thr Gly Asp Arg Glu Asn Asp Ala Glu Ile Asn Glu Glu Thr
        450                 455                 460

Asp Asn Leu Glu Arg Leu Ala Glu Cys Ala Ser Lys Glu Val Thr Arg
465                 470                 475                 480

Pro Phe Thr Val Glu Glu Asp Ser Ile Pro Tyr Gln Gln Gly Ala Ser
                485                 490                 495

Ser Lys Ser Pro Asn Arg Ala Pro Glu Gln Tyr Asn Thr Met Gly Gly
            500                 505                 510

Ser Leu Glu His Ala Glu His Asn Gln Gly Leu His Glu Glu Asn
        515                 520                 525

Val Asn Thr Gly Ser Ala Ser Gly Leu Gln Val Glu Asn Ala Pro Glu
        530                 535                 540

Val His Lys Tyr Ser His Lys Gln Thr Asn Lys Arg Arg Lys Arg Gly
545                 550                 555                 560
```

```
Ser Ser Asp Ser Asn Val Lys Arg Ser Lys Thr Val His Gly Glu
            565                 570                 575

Thr Gly Gly Asp Lys Gln Met Lys Thr Leu Pro His Glu Ser Arg Ala
            580                 585                 590

Lys Lys Gln Thr Lys Gly Lys Ser Asn Glu Arg Glu Lys Lys Pro
        595                 600                 605

Lys Lys Thr Leu Thr His Glu Gly Lys Leu Phe Ser Cys Arg Lys Ser
        610                 615                 620

Leu Ala Ala Ala Gly Thr Lys Ile Glu Gly Val Arg Arg Ser Thr
625                 630                 635                 640

Arg Ile Lys Ser Arg Pro Leu Glu Tyr Trp Arg Gly Glu Arg Phe Leu
                    645                 650                 655

Tyr Gly Arg Ile His Glu Ser Leu Thr Thr Val Ile Gly Ile Lys Tyr
                    660                 665                 670

Ala Ser Pro Gly Glu Gly Lys Arg Asp Ser Arg Ala Ser Lys Val Lys
                675                 680                 685

Ser Phe Val Ser Asp Glu Tyr Lys Lys Leu Val Asp Phe Ala Ala Leu
        690                 695                 700

His
705

<210> SEQ ID NO 97
<211> LENGTH: 312
<212> TYPE: PRT
<213> ORGANISM: Arabidopsis thaliana
<220> FEATURE:
<223> OTHER INFORMATION: thale cress MCM21

<400> SEQUENCE: 97

Met Gly Glu Met Ile Val Ser Met Asp Gln Asp Ile Arg Leu Asp Thr
1               5                   10                  15

Thr Arg Ala Arg Leu Ser Asn Leu Leu Lys Arg His Arg Glu Leu Ser
            20                  25                  30

Asp Arg Leu Thr Arg Asp Ser Asp Lys Thr Met Leu Asp Arg Leu Asn
        35                  40                  45

Lys Glu Phe Glu Ala Ala Arg Arg Ser Gln Ser Gln Glu Val Phe Leu
    50                  55                  60

Asp Gly Glu Glu Trp Asn Asp Gly Leu Leu Ala Thr Leu Arg Glu Arg
65                  70                  75                  80

Val His Met Glu Ala Asp Arg Lys Ala Asp Asn Gly Asn Ala Gly Phe
                85                  90                  95

Ser Leu Val Cys His Pro Glu Glu Arg Ile Thr Tyr Arg Val Gly Asn
            100                 105                 110

Lys Val Ile Cys Cys Leu Asp Gly Ser Arg Ile Gly Ile Gln Phe Glu
        115                 120                 125

Thr Ser Thr Ala Gly Glu Thr Tyr Glu Val Tyr His Cys Val Leu Glu
130                 135                 140

Ser Lys Ser Phe Leu Glu Lys Met Ile Val Leu Glu His Thr Ile Pro
145                 150                 155                 160

Phe Phe Leu Pro Leu Ser Asp Leu Glu Asn Asp Leu Leu Phe Ser Asn
                165                 170                 175

Ala Lys Lys Phe Ile Asp Asn Val Gly Asp Leu Leu Gln Ala Tyr Val
            180                 185                 190

Asp Arg Lys Glu Gln Val Arg Leu Ile Lys Glu Leu Phe Gly His Gln
        195                 200                 205
```

```
Ile Ser Glu Ile Tyr His Ser Leu Pro Tyr His Met Ile Glu Phe Ser
    210                 215                 220

Met Asp Asp Cys Asp Cys Lys Phe Val Val Ser Leu Arg Tyr Gly Asp
225                 230                 235                 240

Leu Leu Cys Glu Leu Pro Thr Lys Val Arg Ile Leu Val Trp Pro Met
                245                 250                 255

His His Leu Ser Lys Lys Gln Cys Thr Ser Pro Gly Ser Pro Ala Ile
                260                 265                 270

Pro Val Arg Leu Pro Phe Ala Glu Asp Ala Phe Arg Ile Gln Ser Leu
            275                 280                 285

Pro Glu Ala Tyr Ala Glu Ile Met Pro Asn Met Pro Asn Glu Ile Arg
290                 295                 300

Gln Leu Phe Gln Thr Ser Pro Ser
305                 310

<210> SEQ ID NO 98
<211> LENGTH: 285
<212> TYPE: PRT
<213> ORGANISM: Arabidopsis thaliana
<220> FEATURE:
<223> OTHER INFORMATION: thale cress minichromosome instability 12
      (MIS12)

<400> SEQUENCE: 98

Met Glu Gly Ser Lys Ser Glu Ala Val Phe Asp Ser Met Asn Leu Asn
1               5                   10                  15

Pro Gln Ile Phe Ile Asn Glu Ala Ile Asn Ser Val Glu Asp Tyr Val
            20                  25                  30

Asp Gln Ala Phe Asp Phe Tyr Ala Arg Asp Ala Ser Lys Ser Leu Lys
        35                  40                  45

Ile Lys Gly Ser Asp Lys Gln Lys Ser Gln Ala Leu Ser Asn Gly Ile
    50                  55                  60

Ala Arg Val Arg Gly Leu Leu Ser Val Ile Asp Asn Arg Leu Lys
65                  70                  75                  80

Leu Trp Glu Ser Tyr Ser Leu Arg Phe Cys Phe Ala Val Pro Asp Gly
                85                  90                  95

Phe Val Leu Pro Lys Ser Glu Ser Ser Ser Val His Gln Asp Gly
            100                 105                 110

Leu Tyr Asp Leu Glu Leu Asp Ala Glu Leu Asp Ser Leu Arg Asp Lys
        115                 120                 125

Leu Asn Val Val Gly Lys Arg Ser Val Glu Leu Asp Ser Glu Leu Gln
    130                 135                 140

Ala Leu Glu Arg Ser Ser Val Ser Arg Glu Arg Ser Leu Arg Leu Val
145                 150                 155                 160

Asn Glu Ala Leu Glu Leu Tyr Asp Glu Ser Ser Met Asp Glu Ile Phe
                165                 170                 175

Lys Glu Met Thr Lys Met Ala Ser Glu Leu Arg Ala Ser Val Glu Arg
            180                 185                 190

Leu Lys Thr Arg Arg Met Lys Ala Ser Glu Ser Ala Lys Val Lys Arg
        195                 200                 205

Leu Lys Asn His Gly Lys Glu Phe Ser Ala Met Thr Phe Asp Tyr Val
    210                 215                 220

Val Ser Gly Leu Pro Asn Gly Gly Ser Arg Gln Lys Pro Val Ile Pro
225                 230                 235                 240

Pro Asp Gln Lys Pro Gln His Ile Ile Leu Val Ser Ser Gln Val Ser
                245                 250                 255
```

```
Leu Glu Leu Ala Thr Ser Lys Leu Arg Leu Gly Ser Leu Pro Ile Glu
            260                 265                 270

Leu Thr Thr Leu Asp Tyr Phe Cys Met Cys Phe Ile Met
        275                 280                 285

<210> SEQ ID NO 99
<211> LENGTH: 568
<212> TYPE: PRT
<213> ORGANISM: Arabidopsis thaliana
<220> FEATURE:
<223> OTHER INFORMATION: thale cress NDC80

<400> SEQUENCE: 99

Met Arg Gly Gly Ala Ala Gly Lys Arg Arg Thr Thr Val Gly Phe Gly
1               5                   10                  15

Gly Ala Pro Pro Pro Pro Pro Ser Ile Glu Gln Gln Arg His Leu
            20                  25                  30

Phe Asn Ser Arg Asp Ser Asp Ala Ser Phe Ala Ser Ser Arg Pro Ser
        35                  40                  45

Ser Ile Gly Leu Gly Gly Arg Gly Ala Ser Asp Asp Arg Ser Ser Met
    50                  55                  60

Ile Arg Phe Ile Asn Ala Phe Leu Ser Thr His Asn Phe Pro Ile Ser
65                  70                  75                  80

Ile Arg Gly Asn Pro Val Pro Ser Val Lys Asp Ile Ser Glu Thr Leu
                85                  90                  95

Lys Phe Leu Leu Ser Ala Leu Asp Tyr Pro Cys Asp Ser Ile Lys Trp
            100                 105                 110

Asp Glu Asp Leu Val Phe Phe Leu Lys Ser Gln Lys Cys Pro Phe Lys
        115                 120                 125

Ile Thr Lys Ser Ser Leu Lys Ala Pro Asn Thr Pro His Asn Trp Pro
    130                 135                 140

Thr Val Leu Ala Val Val His Trp Leu Ala Glu Leu Ala Arg Phe His
145                 150                 155                 160

Gln His Leu Val Ser Asn Ser Thr Ser Val Pro Glu Asp Asn Ser Met
                165                 170                 175

Asn Phe Phe Ala Ile Gln Ser Phe Gly His Phe Ile Arg Gly Glu Asp
            180                 185                 190

Asp Lys Val Asn Asp Leu Asp Ser Gln Phe Leu Gly Lys Leu Glu Ala
        195                 200                 205

Glu Lys Thr Ser Val Ala Glu Thr Ile Ser Gly Cys Glu Lys Ile Ser
    210                 215                 220

Gly Glu Leu Glu Ala Lys Leu Glu Ser Leu Arg Lys Gly Pro Ser Lys
225                 230                 235                 240

Lys Glu Ser Leu Glu Lys Val Lys Ala Asp Leu Glu Asn Asp Val Asn
                245                 250                 255

Lys Phe Arg Thr Ile Val Val Glu Tyr Thr Asp Arg Asn Pro Ala Met
            260                 265                 270

Glu Lys Val Val Glu Glu Lys Ala Lys Glu Leu Lys Ala Lys Glu Glu
        275                 280                 285

Glu Arg Glu Arg Ile Ser Val Glu Asn Lys Glu Leu Lys Lys Ser Val
    290                 295                 300

Glu Leu Gln Asn Phe Ser Ala Ala Asp Val Asn Arg Met Arg Arg Glu
305                 310                 315                 320

Leu Gln Ala Val Glu Arg Asp Val Ala Asp Ala Glu Val Ala Arg Asp
                325                 330                 335
```

```
Gly Trp Asp Gln Lys Ala Trp Glu Leu Asn Ser Gln Ile Arg Asn Gln
            340                 345                 350

Phe His Gln Ile Gln Thr Leu Ala Ile Asp Cys Asn Gln Ala Leu Arg
            355                 360                 365

Arg Leu Lys Leu Asp Ile Gln Phe Ala Val Asn Glu Arg Gly Glu Thr
370                 375                 380

Pro Ala Ala Val Met Gly Val Asp Tyr Lys Ser Val Val Lys Pro Ala
385                 390                 395                 400

Leu Cys Ser Leu Cys Asp Gly Ile Lys Gly Ser Ser Ala Glu Lys Val
            405                 410                 415

Glu Glu Leu Val Thr Leu Gln His His Lys Ser Glu Met Ala Ser Lys
            420                 425                 430

Ile Glu Ser Lys Arg Ser Leu Leu Gly Ser Ile Gln Leu Gln Ile Asn
            435                 440                 445

Asp Leu Glu Glu Lys Met Lys Leu Val Lys Lys Glu Thr Gln Glu Leu
            450                 455                 460

Ser Thr Lys Cys Asp Leu Glu Ala Lys Thr Leu Val Glu Ser Val Lys
465                 470                 475                 480

Ala Glu Ala Leu Asn Leu Glu Val Val Glu Lys Glu Ala Ala Glu Phe
            485                 490                 495

Val Lys Ala Ser Glu Leu Arg Leu Gln Glu Ala Val Lys Glu Ser Glu
            500                 505                 510

Glu Glu Val Gln Ala Cys Ala Ala Gln Leu Phe Ala Leu Ile Asp Ser
            515                 520                 525

Ile Ser Lys Gln Lys Glu Tyr Met Asp Ser Lys Ile Ser Glu Ile Lys
            530                 535                 540

Thr Gly Val Ala Asp Thr Ala Ser Ala Val Ser Glu Ile Tyr Lys Ala
545                 550                 555                 560

Asn Phe Lys Lys Asn Leu Gly Ile
                565

<210> SEQ ID NO 100
<211> LENGTH: 440
<212> TYPE: PRT
<213> ORGANISM: Arabidopsis thaliana
<220> FEATURE:
<223> OTHER INFORMATION: thale cress NUF2

<400> SEQUENCE: 100

Met Ser Ala Tyr Glu Tyr Pro Arg Leu Ser Arg Ser Asp Ile Ile Thr
1               5                   10                  15

Ala Leu Lys Asp Ala Gln Ile Ala Ser Val Thr Glu Thr Asp Leu Lys
            20                  25                  30

Thr Pro Thr Ser Asp Phe Val Ser Glu Leu Tyr Thr Arg Ile Leu Ile
            35                  40                  45

Tyr Leu Asp Ala Leu Asp Glu Glu Lys Gly Gln Val Asp Phe Glu
            50              55                  60

Ala Leu Glu Gln Leu Glu Asn Pro Asp His His Ala Thr Ser Met Gln
65                  70                  75                  80

Ala Met Lys Leu Tyr Cys Lys Val Lys Asp Met Leu Glu Met Leu Asp
            85                  90                  95

Cys Pro Leu Pro Ile Ser Phe Lys Asp Leu Leu Arg Pro Glu Ser Ser
            100                 105                 110

Arg Thr Glu Phe Phe Ile Ser Ala Leu Leu Asn Tyr Gly Leu Tyr Lys
            115                 120                 125
```

```
Asp Ser Lys Met Asp Leu Ile Arg Pro Lys Ala Glu Glu Leu Gly Leu
        130                 135                 140

Leu Asp Glu Gln Arg Lys Gln Cys Glu Ala Lys Val Ala Gln Leu Asn
145                 150                 155                 160

Ala Glu Ile Gly Glu Phe Asp Glu Ala Val Glu Arg Asp Leu Pro Phe
                165                 170                 175

Val Gln Glu Leu Glu Ala Asn Ile Glu Gln Leu Asn Lys Lys Ile Leu
                180                 185                 190

Glu Leu Asn Asn Gln Gln Met Ser Leu Arg Ala Thr Phe Gln Lys Met
            195                 200                 205

Arg Glu Lys Ser Thr Gln Met Asp Asn Glu Ile Ser Lys Ala Glu Phe
210                 215                 220

Asp Leu Val Glu Thr Val Gln Glu Asn Ala Asn Leu Arg Ser Gln Ile
225                 230                 235                 240

Val Gln Ser Pro Asp Lys Leu Gln Gly Ala Leu Glu Glu Lys Lys Leu
                245                 250                 255

Val Leu Gly Glu Thr Lys Lys Ala Glu Gln Ser Ala Met Val Thr Phe
                260                 265                 270

Gln Glu Lys Ala Ala Ile Leu Glu Val Phe Lys Ala Leu Lys Lys
            275                 280                 285

Ile Leu Lys Ser Ser Ser Gln Leu Gln Leu Ile Asn Glu Gln Val Thr
290                 295                 300

Asn Ala Lys Thr Val Glu Lys Glu Phe Lys Ala Leu Lys Asp Lys Leu
305                 310                 315                 320

Ser Glu Asp Gly Val Ala Tyr Lys Ser Leu Glu Ala Lys Val Val Glu
                325                 330                 335

Arg Glu Arg Ile Val Glu Gln Leu Asn Glu Ser Leu Lys Gln Leu Glu
            340                 345                 350

Lys Glu Lys Ala Val Met Phe Asp Asp Trp Thr Lys Gln Leu Asn Glu
            355                 360                 365

Leu Lys Val Glu Val Glu Ser Arg Arg Arg Glu Leu Glu Thr Arg Gln
370                 375                 380

Thr Asn Val Glu Ser Val Val Ala Met Val Asp Asp Asn Thr Ala Lys
385                 390                 395                 400

Thr Asn Gln Val Arg Gln Ser Gly Glu Ala Lys Val Lys Lys Leu Ala
                405                 410                 415

Ala Lys Tyr Glu Glu Ile Val Lys Gln Phe His Glu Tyr Thr Val Ser
            420                 425                 430

Phe Asp Ala Phe Leu Pro Ser Leu
            435                 440

<210> SEQ ID NO 101
<211> LENGTH: 1109
<212> TYPE: DNA
<213> ORGANISM: Artificial Sequence
<220> FEATURE:
<223> OTHER INFORMATION: synthetic maize CENH3 tail, Arabidopsis
      histone-fold domain

<400> SEQUENCE: 101
atggctcgaa ccaagcacca ggccgtgagg aagacggcgg agaagcccaa gaagaagctc      60
cagttcgagc gctcaggtgg tgcgagtacc tcggcgacgc cggaaagggc tgctgggacc     120
gggggaagag cggcgtctgg aggtgactca gttaagaaga cgaaaccacg ccaccgctgg     180
aggccaggaa ccgttgctct aaaagagatt cgccatttcc agaagcagac aaaccttctt     240
```

```
attccggctg ccagtttcat aagagaagtt agttactctt tttcttacca gccataataa    300
gtttcacagc ttaacaatat tcatatatac taacagaggc acaagccttt tggtgtttaa    360
tgtggctagt tttaggattt gcacacccca cacatatctg agcatcaatg cagtgtacat    420
agtgagtgat atagcaattt aactaaaatt cagagtaatc gtgaggccaa ccctccttgt    480
ttaaggagtg tgtaatctag tttgtctttg aggttatgag ctcatagatt cagaaccata    540
tgattcctgt agctacaaaa ctcaacatga atcgtcagtg atgtggaaat gctgatttgt    600
gttacaaaca aactatttta cattgttttt ccaggtgaga agtataaccc atatgttggc    660
ccctccccaa atcaatcgtt ggacagctga agctcttgtt gctcttcaag aggtaccaat    720
ccttcaactt tttctttata cgaatgtatg aatatagata tagagatagt cacacatttc    780
aactaatgtc attcccttg atgaccaatc aacctaatca cacaaattct ttgtggtagg    840
cggcagaaga ttacttggtt ggtttgttct cagattcaat gctctgtgct atccatgcaa    900
gacgtgttac tctaagtaag tactctaaaa gaagacattt ttcagtctca acttaggaat    960
cacaagcata cattttatat ccctttgaat cattagttac ttgaatatca tatataaaaa   1020
tgcttatcta tatctgtttt ttgttcatat cagtgagaaa agactttgaa cttgcacgcc   1080
ggcttggagg aaaaggcaga ccatggtga                                     1109
```

<210> SEQ ID NO 102
<211> LENGTH: 477
<212> TYPE: DNA
<213> ORGANISM: Artificial Sequence
<220> FEATURE:
<223> OTHER INFORMATION: synthetic maize CENH3 tail cDNA

<400> SEQUENCE: 102

```
atggctcgaa ccaagcacca ggccgtgagg aagacggcgg agaagcccaa gaagaagctc     60
cagttcgagc gctcaggtgg tgcgagtacc tcggcgacgc cggaaagggc tgctgggacc    120
gggggaagag cggcgtctgg aggtgactca gttaagaaga cgaaaccacg ccaccgctgg    180
aggccaggaa ccgttgctct aaaagagatt cgccatttcc agaagcagac aaaccttctt    240
attccggctg ccagtttcat aagagaagtg agaagtataa cccatatgtt ggcccctccc    300
caaatcaatc gttggacagc tgaagctctt gttgctcttc aagaggcggc agaagattac    360
ttggttggtt tgttctcaga ttcaatgctc tgtgctatcc atgcaagacg tgttactcta    420
atgagaaaag actttgaact tgcacgccgg cttggaggaa aaggcagacc atggtga      477
```

<210> SEQ ID NO 103
<211> LENGTH: 158
<212> TYPE: PRT
<213> ORGANISM: Artificial Sequence
<220> FEATURE:
<223> OTHER INFORMATION: synthetic maize tailswap protein

<400> SEQUENCE: 103

```
Met Ala Arg Thr Lys His Gln Ala Val Arg Lys Thr Ala Glu Lys Pro
 1               5                  10                  15

Lys Lys Lys Leu Gln Phe Glu Arg Ser Gly Gly Ala Ser Thr Ser Ala
            20                  25                  30

Thr Pro Glu Arg Ala Ala Gly Thr Gly Gly Arg Ala Ala Ser Gly Gly
        35                  40                  45

Asp Ser Val Lys Lys Thr Lys Pro Arg His Arg Trp Arg Pro Gly Thr
    50                  55                  60
```

-continued

```
Val Ala Leu Lys Glu Ile Arg His Phe Gln Lys Gln Thr Asn Leu Leu
 65                 70                  75                  80

Ile Pro Ala Ala Ser Phe Ile Arg Glu Val Arg Ser Ile Thr His Met
                 85                  90                  95

Leu Ala Pro Pro Gln Ile Asn Arg Trp Thr Ala Glu Ala Leu Val Ala
            100                 105                 110

Leu Gln Glu Ala Ala Glu Asp Tyr Leu Val Gly Leu Phe Ser Asp Ser
        115                 120                 125

Met Leu Cys Ala Ile His Ala Arg Arg Val Thr Leu Met Arg Lys Asp
130                 135                 140

Phe Glu Leu Ala Arg Arg Leu Gly Gly Lys Gly Arg Pro Trp
145                 150                 155

<210> SEQ ID NO 104
<211> LENGTH: 708
<212> TYPE: DNA
<213> ORGANISM: Artificial Sequence
<220> FEATURE:
<223> OTHER INFORMATION: synthetic mCherry red fluorescent protein DsRed
      variant

<400> SEQUENCE: 104
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420 atgcagaaga gaccatgggc tgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaag                  708

<210> SEQ ID NO 105
<211> LENGTH: 236
<212> TYPE: PRT
<213> ORGANISM: Artificial Sequence
<220> FEATURE:
<223> OTHER INFORMATION: synthetic mCherry red fluorescent protein DsRed
      variant

<400> SEQUENCE: 105

Met Val Ser Lys Gly Glu Glu Asp Asn Met Ala Ile Ile Lys Glu Phe
  1               5                  10                  15

Met Arg Phe Lys Val His Met Glu Gly Ser Val Asn Gly His Glu Phe
                 20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
 65                 70                  75                  80
```

```
Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
            130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys
225                 230                 235

<210> SEQ ID NO 106
<211> LENGTH: 211
<212> TYPE: PRT
<213> ORGANISM: Candida albicans
<220> FEATURE:
<223> OTHER INFORMATION: yeast CENH3

<400> SEQUENCE: 106

Met Ala Arg Leu Ser Gly Gln Ser Ser Gly Arg Gln Thr Gly Gln Gly
1               5                   10                  15

Thr Ser Ala Glu Ala Ile Arg Gln Gln Arg Glu Glu Leu Arg Arg Gln
            20                  25                  30

Arg Glu Leu Arg Leu Gln Gln Gln Gln Ala Glu Arg Gln Gln Gln
        35                  40                  45

Arg Gln Gln Tyr Arg Thr Glu Gln Ser Pro Ile Val Pro Ala Ala Thr
    50                  55                  60

Ser Ser Ser Arg Tyr Ser Gln Phe Gly Ile Tyr Arg Asn Gln Pro Gly
65                  70                  75                  80

Asp Val Val Asp Thr Leu Ala Ser Ser Leu Pro Arg Arg Thr Thr Thr
                85                  90                  95

Thr Arg Pro Glu Val Asn Arg Thr Val Pro Arg Val Lys Lys Arg Tyr
            100                 105                 110

Arg Pro Gly Thr Lys Ala Leu Arg Glu Ile Arg Gln Tyr Gln Lys Ser
            115                 120                 125

Thr Asp Leu Leu Ile Arg Lys Leu Pro Phe Ala Arg Leu Val Arg Glu
            130                 135                 140

Ile Ser Leu Asp Phe Val Gly Pro Ser Tyr Gly Leu Arg Trp Gln Ser
145                 150                 155                 160

Asn Ala Ile Leu Ala Leu Gln Glu Ala Ser Glu Ser Phe Leu Ile His
                165                 170                 175

Leu Leu Glu Asp Thr Asn Leu Cys Ala Ile His Ala Lys Arg Val Thr
            180                 185                 190

Ile Met Gln Lys Asp Ile Gln Leu Ala Arg Arg Ile Arg Gly Gln Ser
            195                 200                 205
```

Trp Ile Leu
    210

<210> SEQ ID NO 107
<211> LENGTH: 140
<212> TYPE: PRT
<213> ORGANISM: Homo sapiens
<220> FEATURE:
<223> OTHER INFORMATION: human CENH3

<400> SEQUENCE: 107

Met Gly Pro Arg Arg Ser Arg Lys Pro Glu Ala Pro Arg Arg Arg
1               5                   10                  15

Ser Pro Ser Pro Thr Pro Thr Pro Gly Pro Ser Arg Arg Gly Pro Ser
                20                  25                  30

Leu Gly Ala Ser Ser His Gln His Ser Arg Arg Arg Gln Gly Trp Leu
            35                  40                  45

Lys Glu Ile Arg Lys Leu Gln Lys Ser Thr His Leu Leu Ile Arg Lys
50                  55                  60

Leu Pro Phe Ser Arg Leu Ala Arg Glu Ile Cys Val Lys Phe Thr Arg
65                  70                  75                  80

Gly Val Asp Phe Asn Trp Gln Ala Gln Ala Leu Leu Ala Leu Gln Glu
                85                  90                  95

Ala Ala Glu Ala Phe Leu Val His Leu Phe Glu Asp Ala Tyr Leu Leu
            100                 105                 110

Thr Leu His Ala Gly Arg Val Thr Leu Phe Pro Lys Asp Val Gln Leu
        115                 120                 125

Ala Arg Arg Ile Arg Gly Leu Glu Glu Gly Leu Gly
    130                 135                 140

<210> SEQ ID NO 108
<211> LENGTH: 164
<212> TYPE: PRT
<213> ORGANISM: Oryza sativa
<220> FEATURE:
<223> OTHER INFORMATION: rice centromeric histone 3 (CENH3)

<400> SEQUENCE: 108

Met Ala Arg Thr Lys His Pro Ala Val Arg Lys Ser Lys Ala Glu Pro
1               5                   10                  15

Lys Lys Lys Leu Gln Phe Glu Arg Ser Pro Arg Pro Ser Lys Ala Gln
                20                  25                  30

Arg Ala Gly Gly Gly Thr Gly Thr Ser Ala Thr Thr Arg Ser Ala Ala
            35                  40                  45

Gly Thr Ser Ala Ser Gly Thr Pro Arg Gln Gln Thr Lys Gln Arg Lys
50                  55                  60

Pro His Arg Phe Arg Pro Gly Thr Val Ala Leu Arg Glu Ile Arg Lys
65                  70                  75                  80

Phe Gln Lys Thr Thr Glu Leu Leu Ile Pro Phe Ala Pro Phe Ser Arg
                85                  90                  95

Leu Val Arg Glu Ile Thr Asp Phe Tyr Ser Lys Asp Val Ser Arg Trp
            100                 105                 110

Thr Leu Glu Ala Leu Leu Ala Leu Gln Glu Ala Ala Glu Tyr His Leu
        115                 120                 125

Val Asp Ile Phe Glu Val Ser Asn Leu Cys Ala Ile His Ala Lys Arg
    130                 135                 140

Val Thr Ile Met Gln Lys Asp Met Gln Leu Ala Arg Arg Ile Gly Gly
145                 150                 155                 160

<210> SEQ ID NO 109
<211> LENGTH: 97
<212> TYPE: PRT
<213> ORGANISM: Artificial Sequence
<220> FEATURE:
<223> OTHER INFORMATION: synthetic CENH3 histone-fold domain

<400> SEQUENCE: 109

Pro Gly Thr Val Ala Leu Lys Glu Ile Arg His Phe Gln Lys Gln Thr
1               5                   10                  15

Asn Leu Leu Ile Pro Ala Ala Ser Phe Ile Arg Glu Val Arg Ser Ile
            20                  25                  30

Thr His Met Leu Ala Pro Pro Gln Ile Asn Arg Trp Thr Ala Glu Ala
        35                  40                  45

Leu Val Ala Leu Gln Glu Ala Ala Glu Asp Tyr Leu Val Gly Leu Phe
    50                  55                  60

Ser Asp Ser Met Leu Cys Ala Ile His Ala Arg Arg Val Thr Leu Met
65                  70                  75                  80

Arg Lys Asp Phe Glu Leu Ala Arg Arg Leu Gly Gly Lys Gly Arg Pro
                85                  90                  95

Trp

<210> SEQ ID NO 110
<211> LENGTH: 30
<212> TYPE: DNA
<213> ORGANISM: Artificial Sequence
<220> FEATURE:
<223> OTHER INFORMATION: synthetic PCR amplification primer CP 384
<220> FEATURE:
<221> NAME/KEY: modified_base
<222> LOCATION: (1)...(4)
<223> OTHER INFORMATION: n = g, a, c or t

<400> SEQUENCE: 110
nnnngtcgac atggctcgaa ccaagcacca                                    30

<210> SEQ ID NO 111
<211> LENGTH: 27
<212> TYPE: DNA
<213> ORGANISM: Artificial Sequence
<220> FEATURE:
<223> OTHER INFORMATION: synthetic PCR amplification primer CP 572

<400> SEQUENCE: 111
caacggttcc tggcctccag cggtggc                                       27

<210> SEQ ID NO 112
<211> LENGTH: 27
<212> TYPE: DNA
<213> ORGANISM: Artificial Sequence
<220> FEATURE:
<223> OTHER INFORMATION: synthetic PCR amplification primer CP 571

<400> SEQUENCE: 112
gccaccgctg gaggccagga accgttg                                       27

<210> SEQ ID NO 113
<211> LENGTH: 34
<212> TYPE: DNA
<213> ORGANISM: Artificial Sequence
<220> FEATURE:

```
<223> OTHER INFORMATION: synthetic PCR amplification primer CP 375
<220> FEATURE:
<221> NAME/KEY: modified_base
<222> LOCATION: (1)...(4)
<223> OTHER INFORMATION: n = g, a, c or t

<400> SEQUENCE: 113
nnnntctaga tcaccatggt ctgccttttc ctcc                               34

<210> SEQ ID NO 114
<211> LENGTH: 6
<212> TYPE: PRT
<213> ORGANISM: Artificial Sequence
<220> FEATURE:
<223> OTHER INFORMATION: synthetic conserved sequence at border between
      tail domain and histone-fold domain of CENH3
      proteins

<400> SEQUENCE: 114

Pro Gly Thr Val Ala Leu
1               5
```